(12) United States Patent
Kostrzewski et al.

(10) Patent No.: US 8,899,462 B2
(45) Date of Patent: Dec. 2, 2014

(54) APPARATUS FOR ENDOSCOPIC PROCEDURES

(75) Inventors: Stanislaw Kostrzewski, Newton, CT (US); Paul A. Scirica, Huntington, CT (US); Ernest Aranyi, Easton, CT (US); David Racenet, Middletown, CT (US); Frank Marini, Monroe, CT (US); Dwight Bronson, Cheshire, CT (US); William Powers, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 600 days.

(21) Appl. No.: 13/280,898

(22) Filed: Oct. 25, 2011

(65) Prior Publication Data

US 2013/0098966 A1    Apr. 25, 2013

(51) Int. Cl.
| | |
|---|---|
| *A61B 17/068* | (2006.01) |
| *A61B 17/072* | (2006.01) |
| *A61B 17/00* | (2006.01) |
| *A61B 17/29* | (2006.01) |

(52) U.S. Cl.
CPC ......... *A61B 17/07207* (2013.01); *A61B 17/068* (2013.01); *A61B 2017/00314* (2013.01); *A61B 2017/0046* (2013.01); *A61B 2017/00734* (2013.01); *A61B 2017/07271* (2013.01); *A61B 2017/07278* (2013.01); *A61B 2017/2905* (2013.01); *A61B 2017/2923* (2013.01); *A61B 2017/2943* (2013.01); *A61B 17/07292* (2013.01); *A61B 2017/07285* (2013.01)
USPC .................. 227/175.1; 227/176.1; 227/180.1; 227/175.2

(58) Field of Classification Search
CPC ........... A61B 17/068; A61B 17/07207; A61B 2017/00398; A61B 2017/00734; A61B 2018/1455; A61B 2017/07278

USPC ..................... 227/175.1, 176.1, 180.1, 175.2
See application file for complete search history.

(56) References Cited

U.S. PATENT DOCUMENTS

| | | |
|---|---|---|
| 2,777,340 A | 1/1957 | Hettwer et al. |
| 2,957,353 A | 10/1960 | Babacz |
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |

(Continued)

FOREIGN PATENT DOCUMENTS

| | | |
|---|---|---|
| CA | 2451558 A1 | 1/2003 |
| CN | 102247182 A | 11/2011 |

(Continued)

OTHER PUBLICATIONS

European search Report from Appl. No. 13177163.6 dated Nov. 15, 2013. (8 pp).

(Continued)

*Primary Examiner* — Michelle Lopez

(57) ABSTRACT

An electromechanical surgical system comprises a hand-held surgical instrument including an instrument housing defining a connecting portion for selectively connecting with a shaft assembly, the surgical instrument having at least one rotatable drive member, and an end effector configured to perform at least one function. The shaft assembly selectively interconnects the end effector and the surgical device. The shaft assembly includes a transmission housing and a force transmitting assembly for interconnecting the rotatable drive member and a rotation receiving member supported in the end effector.

23 Claims, 36 Drawing Sheets

(56) References Cited

U.S. PATENT DOCUMENTS

| | | |
|---|---|---|
| 4,606,343 A | 8/1986 | Conta et al. |
| 4,705,038 A | 11/1987 | Sjostrom et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,413,267 A | 5/1995 | Solyntjes et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,542,594 A | 8/1996 | McKean et al. |
| 5,562,239 A | 10/1996 | Boiarski et al. |
| 5,653,374 A | 8/1997 | Young et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,779,130 A | 7/1998 | Alesi et al. |
| 5,782,397 A | 7/1998 | Koukline |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,017,354 A | 1/2000 | Culp et al. |
| 6,045,560 A | 4/2000 | McKean et al. |
| 6,090,123 A | 7/2000 | Culp et al. |
| 6,129,547 A | 10/2000 | Cise et al. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,698,643 B2 | 3/2004 | Whitman |
| 6,699,177 B1 | 3/2004 | Wang et al. |
| 6,716,233 B1 | 4/2004 | Whitman |
| 6,792,390 B1 | 9/2004 | Burnside et al. |
| 6,817,508 B1 | 11/2004 | Racenet et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 7,032,798 B2 | 4/2006 | Whitman et al. |
| 7,055,731 B2 | 6/2006 | Shelton, IV et al. |
| 7,077,856 B2 | 7/2006 | Whitman |
| 7,111,769 B2 | 9/2006 | Wales et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton et al. |
| 7,481,347 B2 | 1/2009 | Roy |
| 7,487,899 B2 | 2/2009 | Shelton, IV et al. |
| 7,549,564 B2 | 6/2009 | Boudreaux |
| 7,568,603 B2 | 8/2009 | Shelton, IV et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,721,931 B2 | 5/2010 | Shelton, IV et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,799,039 B2 | 9/2010 | Shelton, IV et al. |
| 7,802,712 B2 | 9/2010 | Milliman et al. |
| 7,823,592 B2 | 11/2010 | Bettuchi et al. |
| 7,845,537 B2 | 12/2010 | Shelton, IV et al. |
| 7,905,897 B2 | 3/2011 | Whitman et al. |
| 7,918,230 B2 | 4/2011 | Whitman et al. |
| 7,938,307 B2 | 5/2011 | Bettuchi |
| 7,947,034 B2 | 5/2011 | Whitman |
| 7,951,071 B2 | 5/2011 | Whitman et al. |
| 7,963,433 B2 | 6/2011 | Whitman et al. |
| 7,967,178 B2 | 6/2011 | Scirica et al. |
| 7,992,758 B2 | 8/2011 | Whitman et al. |
| 8,016,855 B2 | 9/2011 | Whitman et al. |
| 8,020,743 B2 | 9/2011 | Shelton, IV |
| 8,114,118 B2 | 2/2012 | Knodel et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,220,367 B2 | 7/2012 | Hsu |
| 8,241,322 B2 | 8/2012 | Whitman et al. |
| 8,292,888 B2 | 10/2012 | Whitman |
| 8,357,144 B2 | 1/2013 | Whitman et al. |
| 8,365,972 B2 | 2/2013 | Aranyi et al. |
| 8,372,057 B2 | 2/2013 | Cude et al. |
| 8,391,957 B2 | 3/2013 | Carlson et al. |
| 2004/0111012 A1 | 6/2004 | Whitman |
| 2006/0025816 A1 | 2/2006 | Shelton |
| 2006/0142656 A1 | 6/2006 | Malackowski et al. |
| 2006/0278680 A1 | 12/2006 | Viola et al. |
| 2007/0023477 A1 | 2/2007 | Whitman et al. |
| 2007/0029363 A1 | 2/2007 | Popov |
| 2007/0084897 A1 | 4/2007 | Shelton, IV et al. |
| 2007/0102472 A1 | 5/2007 | Shelton, IV |
| 2007/0152014 A1 | 7/2007 | Gillum et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1* | 8/2007 | Shelton et al. ............ 227/176.1 |
| 2007/0175955 A1 | 8/2007 | Shelton, IV et al. |
| 2007/0175961 A1 | 8/2007 | Shelton et al. |
| 2008/0029570 A1 | 2/2008 | Shelton, IV et al. |
| 2008/0029573 A1 | 2/2008 | Shelton, IV et al. |

(56) References Cited

U.S. PATENT DOCUMENTS

| | | |
|---|---|---|
| 2008/0029574 A1 | 2/2008 | Shelton, IV et al. |
| 2008/0029575 A1 | 2/2008 | Shelton, IV et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0185419 A1 | 8/2008 | Smith et al. |
| 2008/0208195 A1 | 8/2008 | Shores et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2009/0090763 A1 | 4/2009 | Zemlok et al. |
| 2009/0099876 A1 | 4/2009 | Whitman |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0072254 A1* | 3/2010 | Aranyi et al. .............. 227/176.1 |
| 2010/0225073 A1 | 9/2010 | Porter et al. |
| 2011/0040308 A1 | 2/2011 | Cabrera et al. |
| 2011/0077673 A1 | 3/2011 | Grubac et al. |
| 2011/0082476 A1 | 4/2011 | Furnish et al. |
| 2011/0089220 A1 | 4/2011 | Ingmanson et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0174099 A1 | 7/2011 | Ross et al. |
| 2011/0204119 A1 | 8/2011 | McCuen |
| 2011/0215132 A1 | 9/2011 | Aranyi et al. |
| 2011/0218522 A1 | 9/2011 | Whitman |
| 2011/0253765 A1 | 10/2011 | Nicholas et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0089131 A1 | 4/2012 | Zemlok et al. |
| 2012/0143002 A1 | 6/2012 | Aranyi et al. |
| 2012/0223121 A1 | 9/2012 | Viola et al. |
| 2012/0310220 A1 | 12/2012 | Malkowski et al. |
| 2013/0282052 A1 | 10/2013 | Aranyi et al. |

FOREIGN PATENT DOCUMENTS

| | | |
|---|---|---|
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 1690502 | 8/2006 |
| EP | 1736112 | 12/2006 |
| EP | 1769754 | 4/2007 |
| EP | 1813199 A1 | 8/2007 |
| EP | 1813203 | 8/2007 |
| EP | 1813211 A2 | 8/2007 |
| EP | 1943958 | 7/2008 |
| EP | 1943976 | 7/2008 |
| EP | 2027819 | 2/2009 |
| EP | 2055243 A2 | 5/2009 |
| EP | 2098170 A2 | 9/2009 |
| EP | 2100561 | 9/2009 |
| EP | 2165664 A2 | 3/2010 |
| EP | 2 236 098 | 10/2010 |
| EP | 2236098 A2 | 10/2010 |
| EP | 2 263 568 | 12/2010 |
| EP | 2263568 A2 | 12/2010 |
| EP | 2329773 A1 | 6/2011 |
| EP | 2333509 A1 | 6/2011 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2676615 A2 | 12/2013 |
| WO | WO 00/72760 | 12/2000 |
| WO | WO 00/72765 | 12/2000 |
| WO | 03/000138 A2 | 1/2003 |
| WO | WO 03/026511 | 4/2003 |
| WO | WO 03/077769 | 9/2003 |
| WO | WO 2004/107989 | 12/2004 |
| WO | WO 2006/042210 | 4/2006 |
| WO | WO 2007/014355 A2 | 2/2007 |
| WO | WO 2007/026354 | 3/2007 |
| WO | WO 2008/131362 | 10/2008 |
| WO | WO 2008/133956 | 11/2008 |
| WO | WO 2009/039506 A1 | 3/2009 |
| WO | WO 2009/132359 | 10/2009 |
| WO | 2011/108840 A2 | 9/2011 |

OTHER PUBLICATIONS

Extended European Search Report from Application No. EP 13171742.3 dated Jan. 3, 2014.
International Search Report corresponding to PCT/US2005/027266, completed May 30, 2008 and mailed Jun. 18, 2008; (2 pp.).
Extended European Search Report corresponding to EP 08 25 3184.9, completed Feb. 12, 2009 and mailed Feb. 27, 2009; (3 pp.).
Extended European Search Report corresponding to EP 10 25 0228.3, completed May 20, 2010 and mailed Jun. 1, 2010; (6 pp.).
Extended European Search Report corresponding to EP 10 25 1968.3, completed on Jul. 4, 2011 and mailed Jul. 14, 2011; (12 pp.).
Extended European Search Report corresponding to EP 11 15 2266.0, completed Jul. 15, 2011 and mailed Jul. 28, 2011; (3 pp.).
Extended European Search Report corresponding to EP 11 25 0462.6, completed Jul. 20, 2011 and mailed Jul. 28, 2011; (6 pp.).
Extended European Search Report corresponding to EP 11 25 0771.0, completed Feb. 7, 2012 and mailed Feb. 17, 2012; (3 pp.).
Extended European Search Report corresponding to EP 06 78 8914.7, completed May 3, 2012 and mailed May 11, 2012; (8 pp.).
Extended European Search Report corresponding to EP 13 16 3033.7, completed Jun. 27, 2013, and dated Jul. 15, 2013; (8 pp).
European Search Report for EP 10252037.6 date of completion is Mar. 1, 2011 (3 pages).
European Search Report for EP 12186177.7 date of completion is Jan. 30, 2013 (6 pages).
Extended European Search Report corresponding to EP No. 11 17 8021.9, mailed Jun. 4, 2013; (3 pp).
Extended European Search Report corresponding to EP No. 13 16 3033.7, completed Jun. 27, 2013 and mailed Jul. 15, 2013; (8 pp).
Extended European Search Report corresponding to EP No. 12 18 6177.7, completed Aug. 14, 2013 and mailed Aug. 23, 2013; (8 pp).
Partial European Search Report corresponding to EP No. 13 17 1742.3, completed Sep. 17, 2013 and mailed Sep. 25, 2013; (8 pp).
Partial European Search Report corresponding to EP No. 13 17 2400.7, completed Sep. 18, 2013 and mailed Oct. 1, 2013; (7 pp).
Extended European Search Report corresponding to EP No. 13 17 5475.6, completed Sep. 23, 2013 and mailed Oct. 1, 2013; (8 pp).
Extended European Search Report corresponding to EP No. 13 17 5478.0, completed Sep. 24, 2013 and mailed Oct. 2, 2013; (6 pp).
Extended European Search Report corresponding to EP No. 13 17 5479.8, completed Sep. 27, 2013 and mailed Oct. 10, 2013; (7 pp).
Partial Extended European Search Report corresponding to EP 13 17 5477.2, completed Oct. 7, 2013 and mailed Oct. 15, 2013; (7 pp).
Extended European Search Report corresponding to EP No. 08 25 2703.7, completed Oct. 23, 2008 and mailed Oct. 31, 2008; (7 pp).
Extended European Search Report from EP Application No. 13172400.7 dated Jan. 21, 2014.
Extended European Search Report from EP Application No. 13189026.1 dated Jan. 31, 2014.
Extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.

* cited by examiner

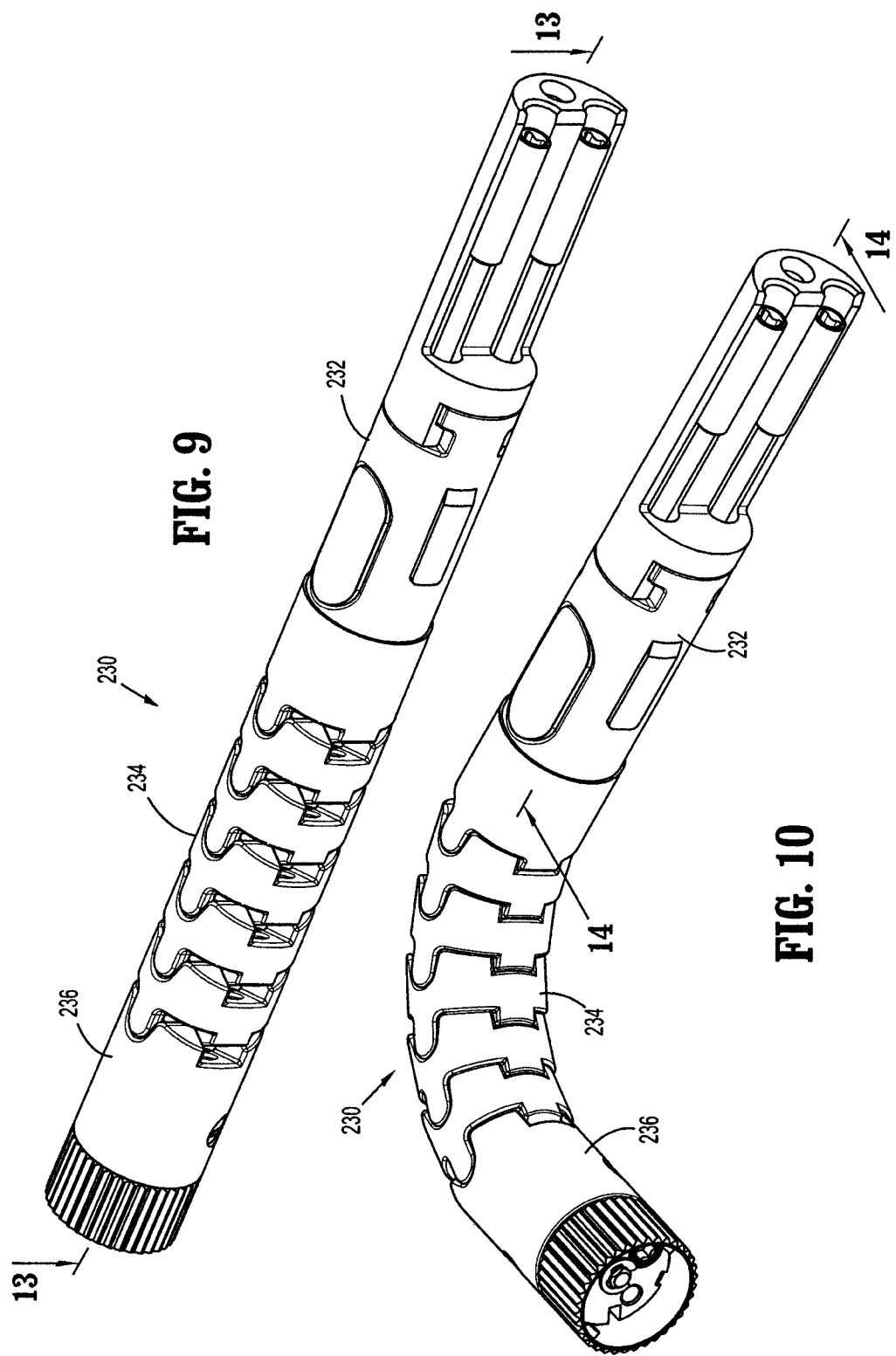

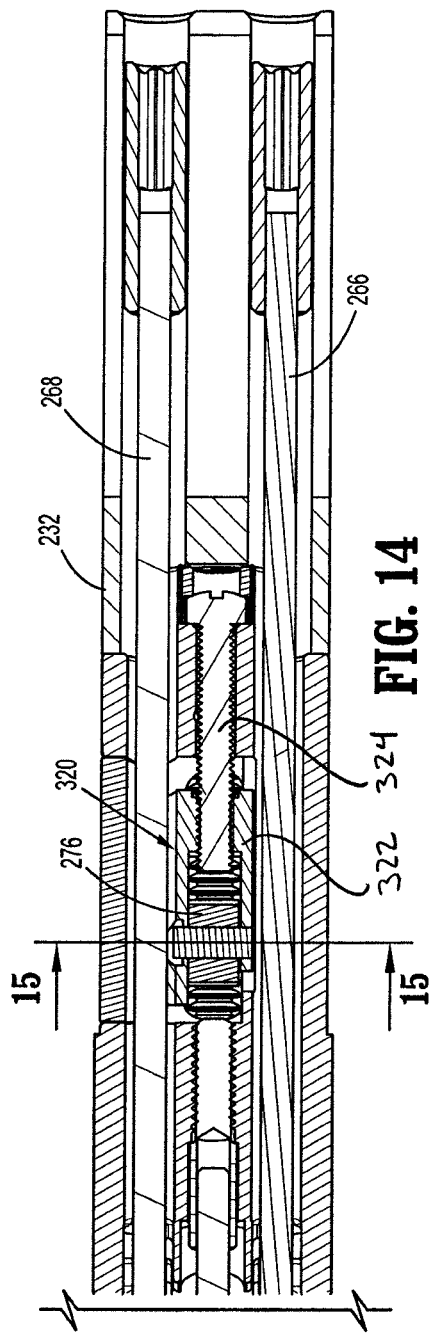
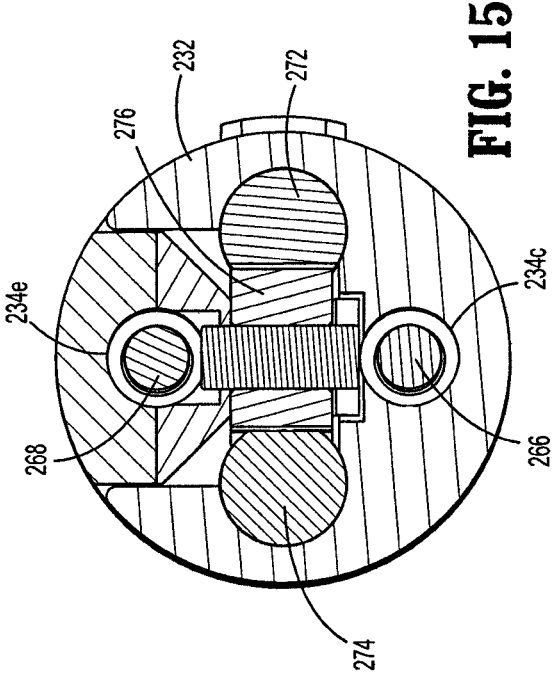

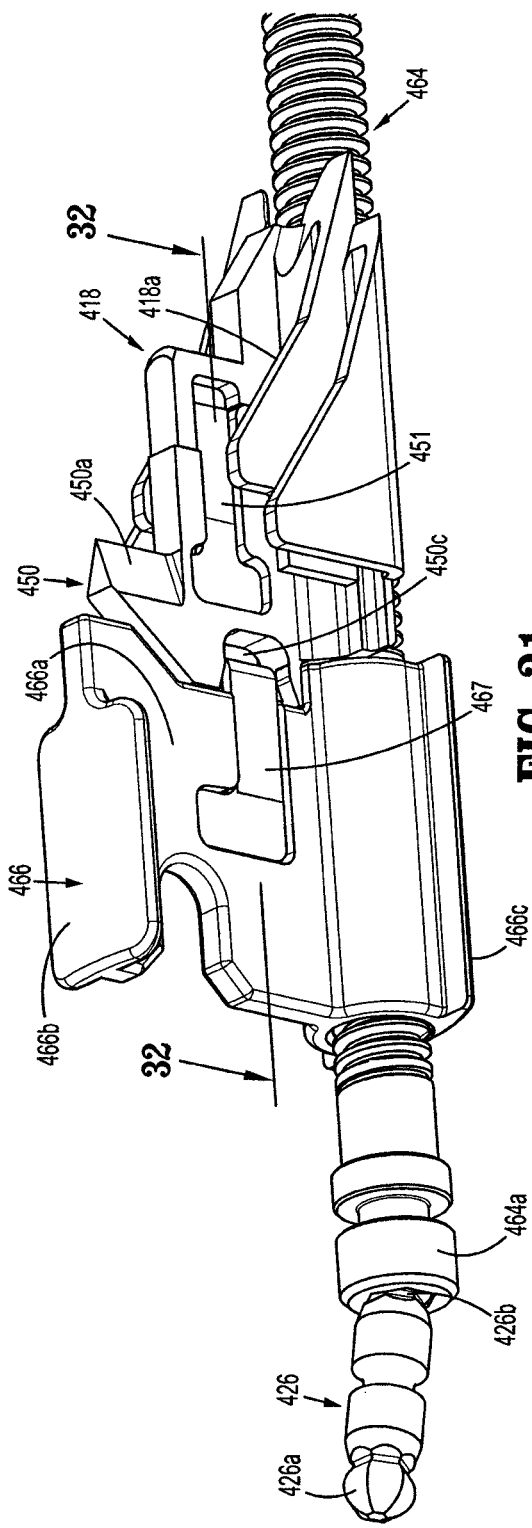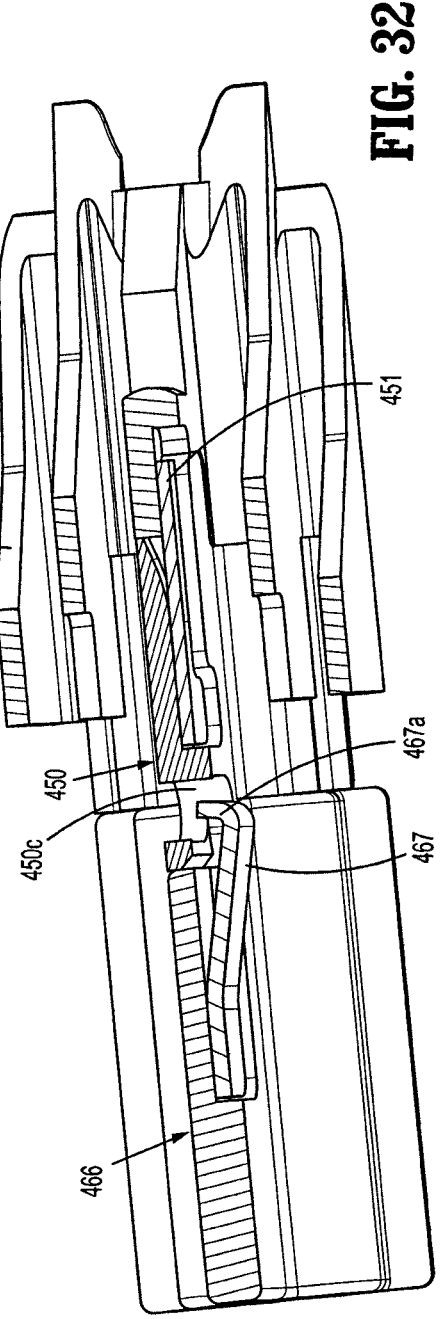

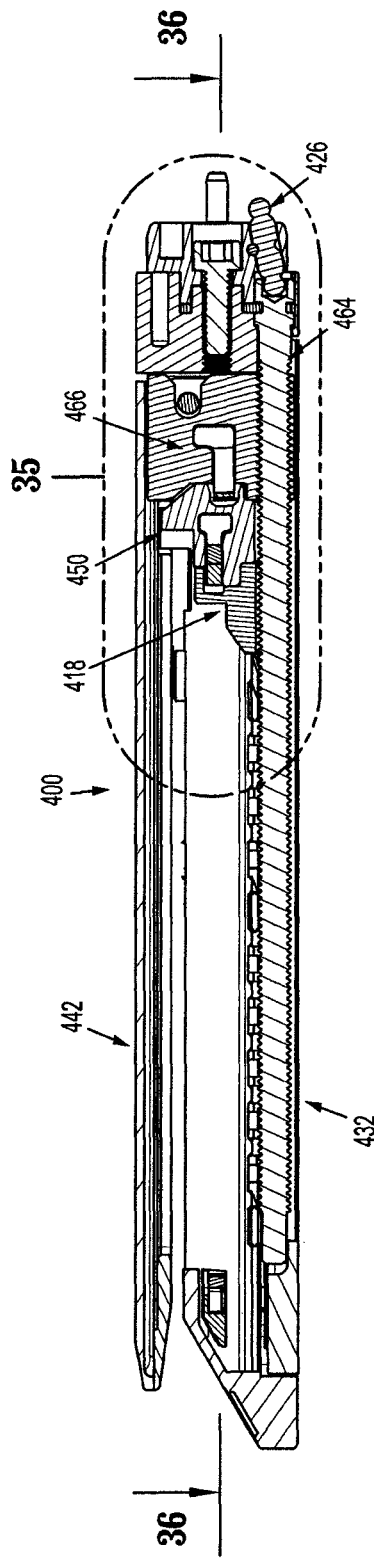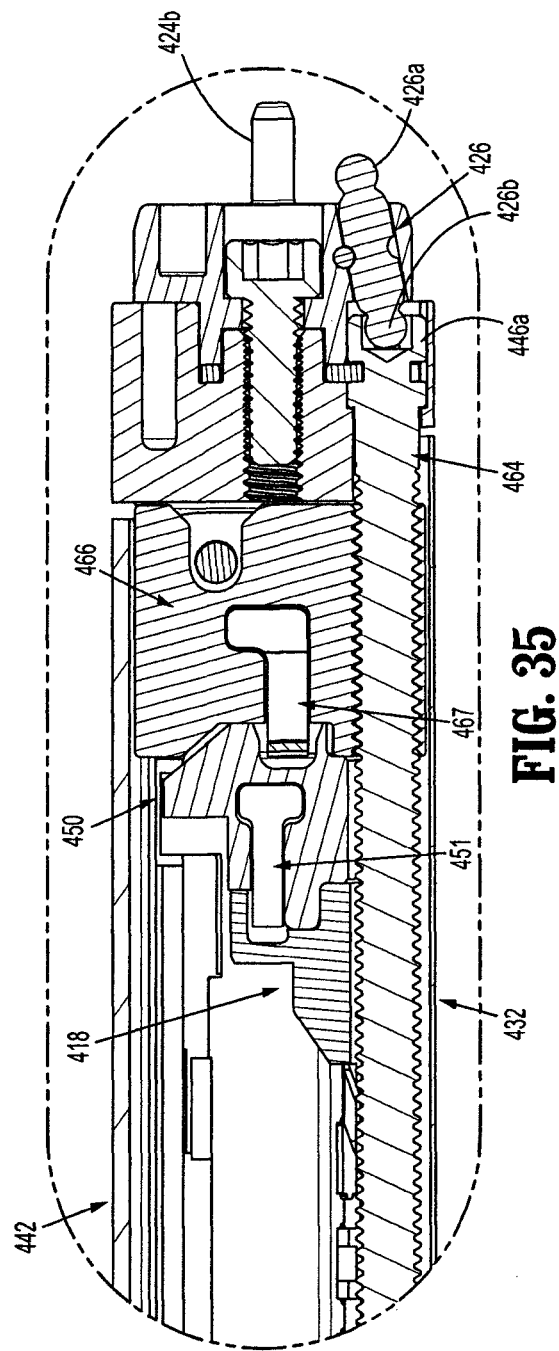
FIG. 34
FIG. 35

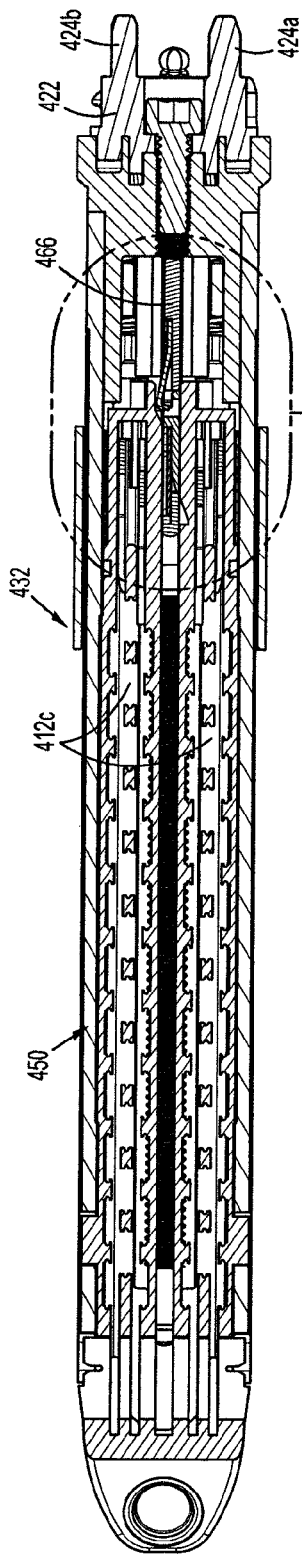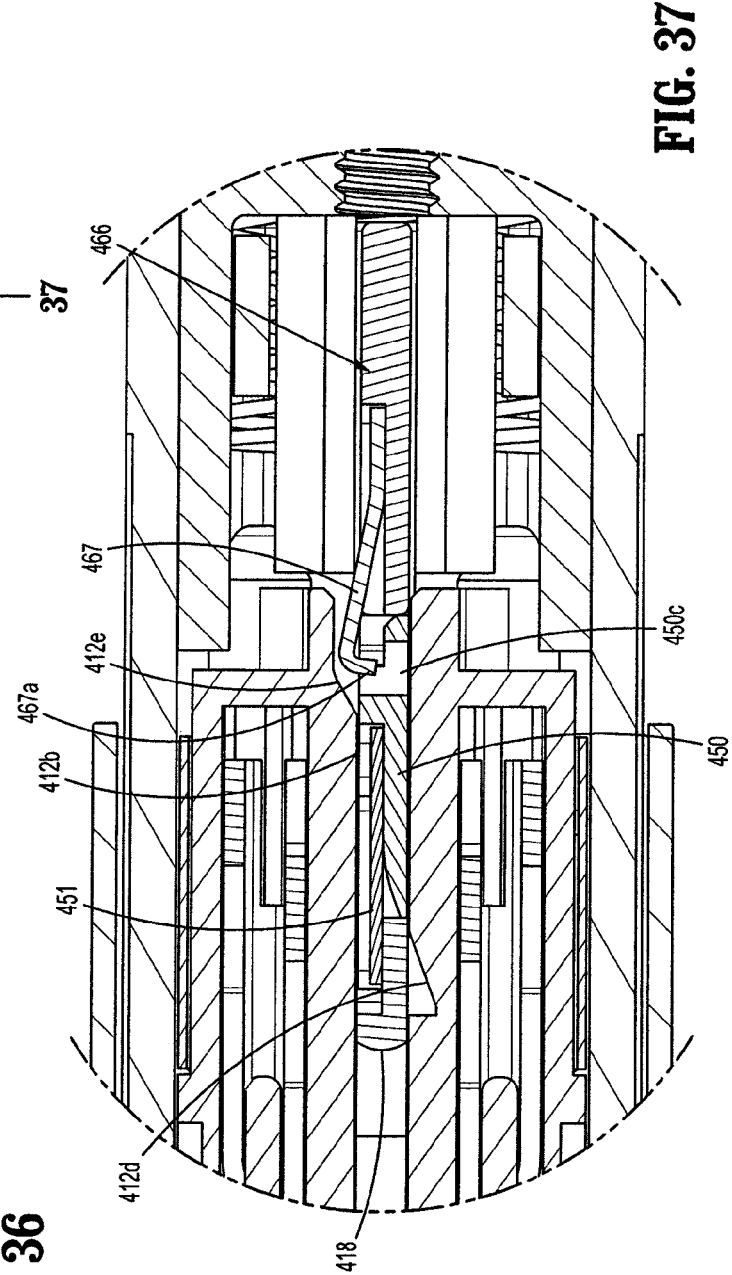
FIG. 36
FIG. 37

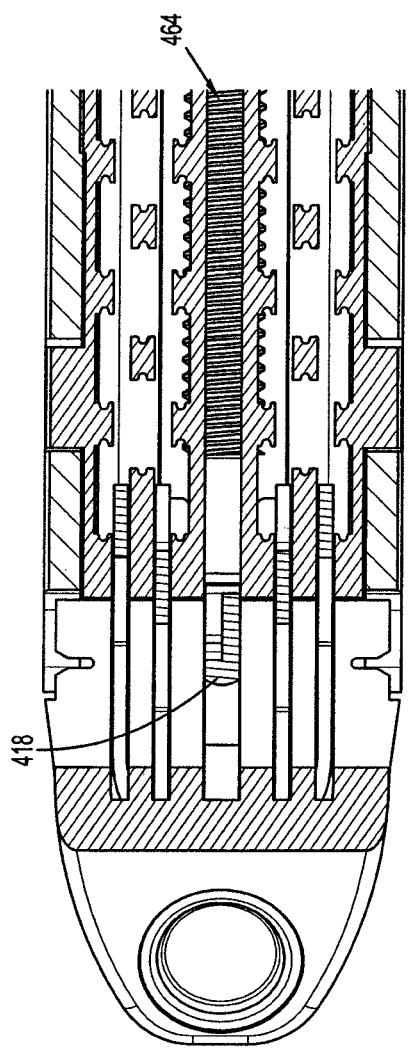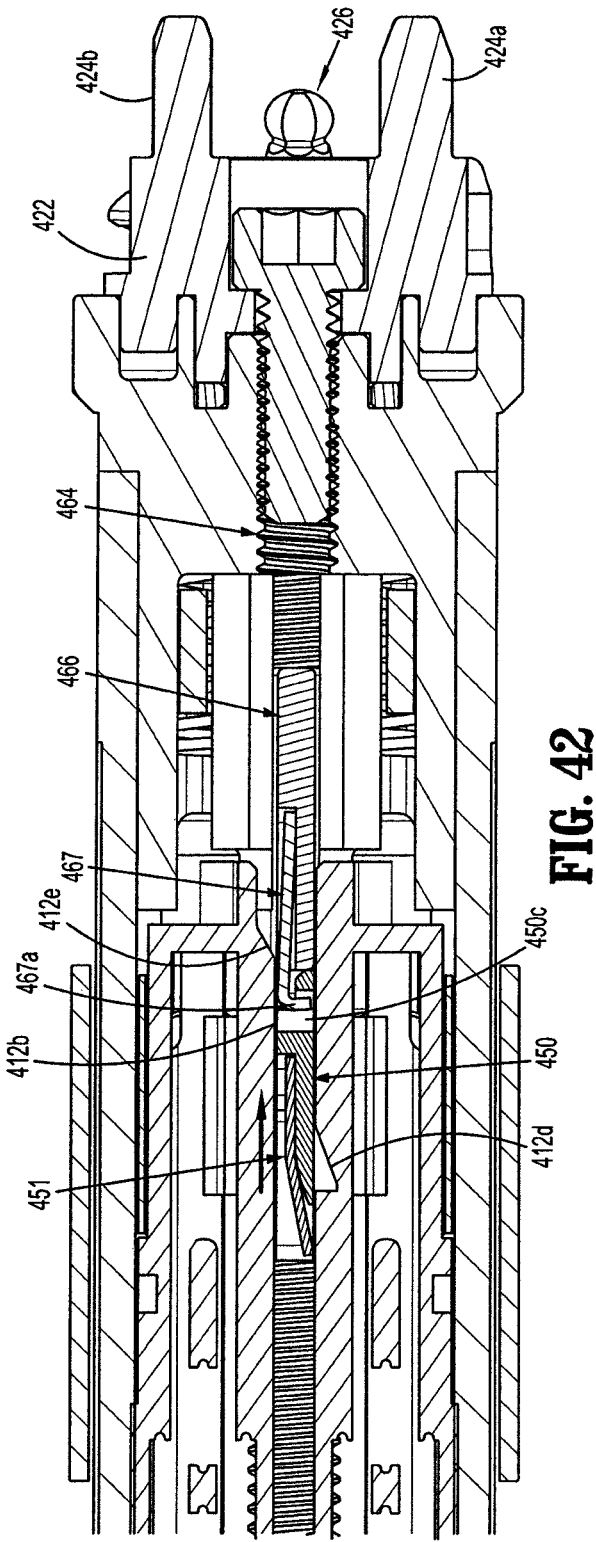
FIG. 41
FIG. 42

APPARATUS FOR ENDOSCOPIC PROCEDURES

BACKGROUND

1. Technical Field

The present disclosure relates to surgical apparatus, devices and/or systems for performing endoscopic surgical procedures and methods of use thereof. More specifically, the present disclosure relates to electromechanical, hand-held surgical apparatus, devices and/or systems configured for use with removable disposable loading units and/or single use loading units for clamping, cutting and/or stapling tissue.

2. Background of Related Art

A number of surgical device manufacturers have developed product lines with proprietary drive systems for operating and/or manipulating electromechanical surgical devices. Some electromechanical surgical devices include a handle assembly, which is reusable, and replaceable loading units and/or single use loading units or the like that are selectively connected to the handle assembly prior to use and then disconnected from the handle assembly following use, in order to be disposed of or in some instances sterilized for re-use.

Many of these electromechanical surgical devices are relatively expensive to manufacture, purchase and/or operate. There is a desire by manufactures and end users to develop electromechanical surgical devices that are relatively inexpensive to manufacture, purchase and/or operate.

Accordingly, a need exists for electromechanical surgical apparatus, devices and/or systems that are relatively economical to develop and manufacture, to store and ship, as well as economical and convenient to purchase and use from the end user's perspective.

SUMMARY

In an aspect of the present disclosure, an electromechanical surgical system comprises a hand-held surgical instrument including an instrument housing defining a connecting portion for selectively connecting with a shaft assembly, the surgical instrument having at least one rotatable drive member, and an end effector configured to perform at least one function. The shaft assembly is arranged for selectively interconnecting the end effector and the surgical device, the shaft assembly including: a transmission housing configured and adapted for selective connection to the connecting portion of the surgical device and to be in operative communication with each of the at least one rotatable drive member of the surgical device; an outer tubular body having a proximal end supported by the transmission housing and a distal end configured and adapted for operative connection with the end effector; and a force transmitting assembly for interconnecting a respective one of the at least one rotatable drive member of the surgical instrument and at least one rotation receiving member supported in the end effector, wherein the force transmitting assembly includes a first end that is connectable to the at least one rotatable drive member of the surgical instrument and a second end that is connectable to the at least one rotation receiving member of the end effector, wherein the force transmitting assembly transmits a rotation of the at least one rotatable drive member of the surgical instrument to the at least one rotation receiving member of the end effector.

The electromechanical surgical system can include a hand-held surgical instrument further including: at least one drive motor supported in the instrument housing and being configured to rotate the at least one rotatable drive member; a battery disposed within the instrument housing for powering the at least one drive motor; and a circuit board disposed within the instrument housing for controlling power delivered from the battery to the motor.

The end effector may includes an upper jaw and a lower jaw, at least one of the upper jaw and the lower jaw being movable in relation to the other of the upper jaw and the lower jaw.

The electromechanical surgical system may further comprise at least one surgical buttress releasably secured to a tissue contacting surface of at least one of the upper jaw and the lower jaw.

The electromechanical surgical system may further comprise a drive beam translatable through at least one of the upper jaw and the lower jaw to move the lower jaw relative to the upper jaw.

The end effector may include: an upper jaw and a lower jaw, at least one of the upper jaw and the lower jaw being movable in relation to the other of the upper jaw and the lower jaw; a cartridge assembly supported in the lower jaw, the cartridge assembly including a plurality of staples therein; and at least one surgical buttress releasably secured to a tissue contacting surface of at least one of the upper jaw and the lower jaw, the at least one surgical buttress secured to the at least one of the upper jaw and the lower jaw by at least one suture, the at least one of the upper jaw and the lower jaw being configured to receive a portion of the at least one suture.

The lower jaw of the end effector may be configured to selectively receive a cartridge assembly, wherein the cartridge assembly includes: a cartridge body defining a longitudinally extending knife slot; a plurality of staples disposed in individual staple retaining slots formed in the cartridge body, wherein the staple retaining slots are arranged in multiple longitudinally extending rows disposed on opposed lateral sides of the knife slot; an actuation sled slidably supported in the cartridge body and being configured to expel at least a portion of the plurality of staples from the cartridge body upon a distal movement of the actuation sled from a proximal-most position; and a knife sled slidably supported in the cartridge body at a location proximal of the actuation sled, wherein the knife sled includes a knife blade extending into the knife slot; wherein the drive beam engages the knife sled and the actuation sled when the cartridge assembly is disposed in the lower jaw and when the drive beam is advanced.

The actuation sled of the cartridge assembly may, in certain embodiments, remain in a distally advanced position following any retraction of the drive beam.

The knife sled of the cartridge assembly may include a lock-out spring extending therefrom, wherein the lock-out spring of the knife sled engages a lock-out notch defined in the cartridge body to inhibit advancement of the knife sled. When the actuation sled and the knife sled are in a proximal-most position, the actuation sled, in certain embodiments, blocks engagement of the lock-out spring of the knife sled with the lock-out notch of the cartridge body.

The knife sled of the cartridge assembly may be retracted upon any retraction of the drive beam. The drive beam may include a lock clip extending therefrom, wherein the lock clip of the drive beam engages the knife sled upon any distal advancement of the drive beam such that the knife sled retracts upon a retraction of the drive beam.

The at least one rotation receiving member of the end effector may include a drive screw rotatably supported in the lower jaw, wherein the drive beam is threadably supported on the drive screw, whereby rotation of the drive screw results in axial translation of the drive beam.

The at least one force transmitting assembly of the shaft assembly may include a first gear train system interconnecting the at least one rotatable drive member of the surgical instrument and the at least one rotation receiving member of the end effector, wherein the first gear train system varies at least one of: a rate of rotation between the at least one rotatable drive member of the surgical instrument and the at least one rotation receiving member of the end effector; and an axis of rotation between the at least one rotatable drive member of the surgical instrument and the at least one rotation receiving member of the end effector.

The shaft assembly may include an articulating neck assembly, and wherein the first gear train system is disposed proximal of the articulating neck assembly. The shaft assembly may include a neck housing disposed distal of the articulating neck assembly, wherein the distal neck housing supports a neck first gear train of the at least one force transmitting assembly, wherein the neck first gear train interconnects an output of the first gear train system with the at least one rotation receiving member of the end effector, wherein the neck first gear train varies at least one of: a rate of rotation between the output of the first gear train system and the at least one rotation receiving member of the end effector; and an axis of rotation between the output of the first gear train system and the at least one rotation receiving member of the end effector.

In any of the aforementioned embodiments, the at least one rotation receiving member of the end effector can include a drive screw rotatably supported in the lower jaw, wherein the drive beam is threadably supported on the drive screw, whereby rotation of the drive screw results in axial translation of the drive beam.

The at least one force transmitting assembly of the shaft assembly may include a second gear train system interconnecting another of the at least one rotatable drive member of the surgical instrument and a rotation hub rotatably supported at a distal end of the neck housing, wherein the second gear train system varies at least one of: a rate of rotation between the another at least one rotatable drive member of the surgical instrument and the rotation hub of the shaft assembly; and an axis of rotation between the another at least one rotatable drive member of the surgical instrument and the rotation hub of the shaft assembly.

The shaft assembly can further include: an articulating neck assembly supported at a distal end of the outer tube; a distal neck housing supported at a distal end of the articulating neck assembly, and first and second diametrically opposed articulation cables extending at least partially along the neck assembly, wherein each articulation cable includes a distal end anchored to the distal neck housing, and a proximal end extending into the outer tube, the proximal end of each articulation cable being secured to a respective first and second rack, each rack being operatively connected to one another by a spur gear, wherein axial displacement of the first rack in a first direction results in: axial displacement of the respective first articulation cable in the first direction; articulation of the neck assembly in a first off-axis direction; and axial displacement of the second articulation cable in a direction opposite to the first direction.

The shaft assembly further includes, in certain embodiments: a threaded rod extending proximally from the first rack; and a threaded shaft threadably connected to the threaded rod extending from the first rack, the threaded shaft being connected to another at least one drive member of the surgical instrument, wherein rotation of the another at least one drive member of the surgical instrument imparts rotation to the threaded shaft and, in turn, axial displacement of the threaded rod and first rack.

In any of the embodiments mentioned above, the shaft assembly further includes: an articulating neck assembly supported at a distal end of the outer tube, the neck assembly defining a central axis and being articulatable in a first plane; a distal neck housing supported at a distal end of the articulating neck assembly, first and second diametrically opposed articulation cables extending at least partially along the neck assembly; a first drive cable extending at least partially along the neck assembly and defining a first drive axis spaced a radial distance from the central axis, the first drive axis being defined by a first drive plane extending orthogonal to the first plane; and a second drive cable extending at least partially along the neck assembly and defining a second drive axis spaced a radial distance from the central axis, the second drive axis being defined by a second drive plane extending orthogonal to the first plane; wherein the first drive cable and the second drive cable are diametrically opposed to one another.

Further details and aspects of exemplary embodiments of the present invention are described in more detail below with reference to the appended figures.

BRIEF DESCRIPTION OF THE DRAWINGS

Embodiments of the present disclosure are described herein with reference to the accompanying drawings, wherein:

FIG. 9 is a perspective view of a neck assembly of the shaft assembly, shown in a straight orientation;

FIG. 10 is a perspective view of the neck assembly of FIG. 9, shown in an articulated condition;

FIG. 14 is a cross-sectional view of the neck assembly of FIGS. 9-12, as taken through 14-14 of FIG. 10;

FIG. 15 is a cross-sectional view of the neck assembly of FIGS. 9-12, as taken through 15-15 of FIG. 14;

FIG. 31 is a further perspective view of the drive beam, the knife sled and the actuation sled of the end effector of FIGS. 27-29;

FIG. 32 is a cross-sectional view as taken through 32-32 of FIG. 31;

FIG. 34 is a cross-sectional view of the end effector of FIG. 27, as taken through 34-34 of FIG. 27, illustrating the drive beam, the knife sled and the actuation sled in a proximal-most position;

FIG. 35 is an enlarged view of the indicated area of detail of FIG. 34;

FIG. 36 is a cross-sectional view of the end effector of FIG. 27, as taken through 36-36 of FIG. 34;

FIG. 37 is an enlarged view of the indicated area of detail of FIG. 36;

FIG. 41 is a cross-sectional view of a distal end of the end effector of FIG. 27, as taken through 34-34 of FIG. 27, illustrating the actuation sled in a distal-most position;

FIG. 42 is a cross-sectional view of a proximal end of the end effector of FIG. 27, as taken through 34-34 of FIG. 27, illustrating the drive beam and the knife sled in a proximal position;

DETAILED DESCRIPTION OF EMBODIMENTS

Figure 1:
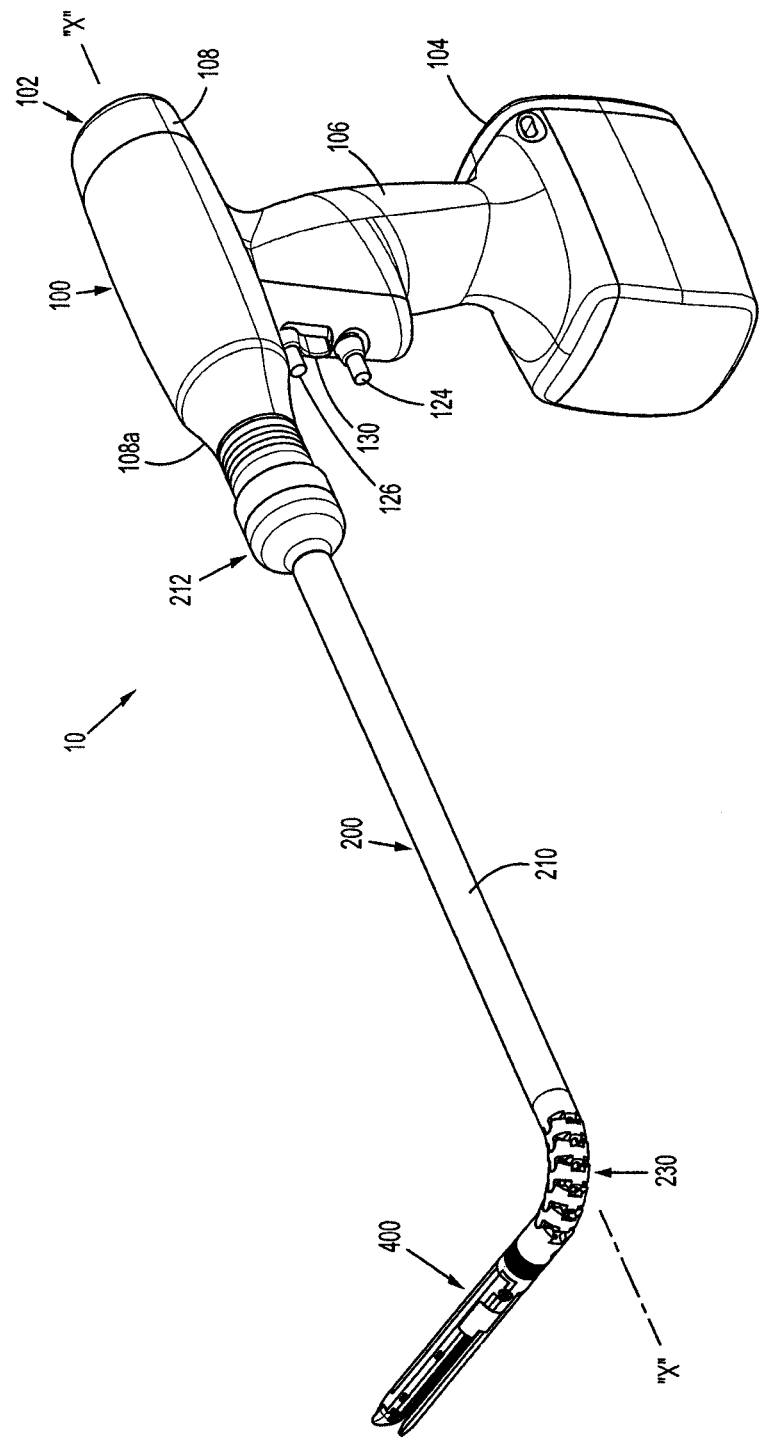
FIG. 1 is a perspective view of an electromechanical surgical system according to an embodiment of the present disclosure.

Embodiments of the presently disclosed electromechanical surgical system, apparatus and/or device are described in detail with reference to the drawings, in which like reference numerals designate identical or corresponding elements in each of the several views. As used herein the term "distal" refers to that portion of the electromechanical surgical system, apparatus and/or device, or component thereof, that are farther from the user, while the term "proximal" refers to that portion of the electromechanical surgical system, apparatus and/or device, or component thereof, that are closer to the user.

Figure 2:
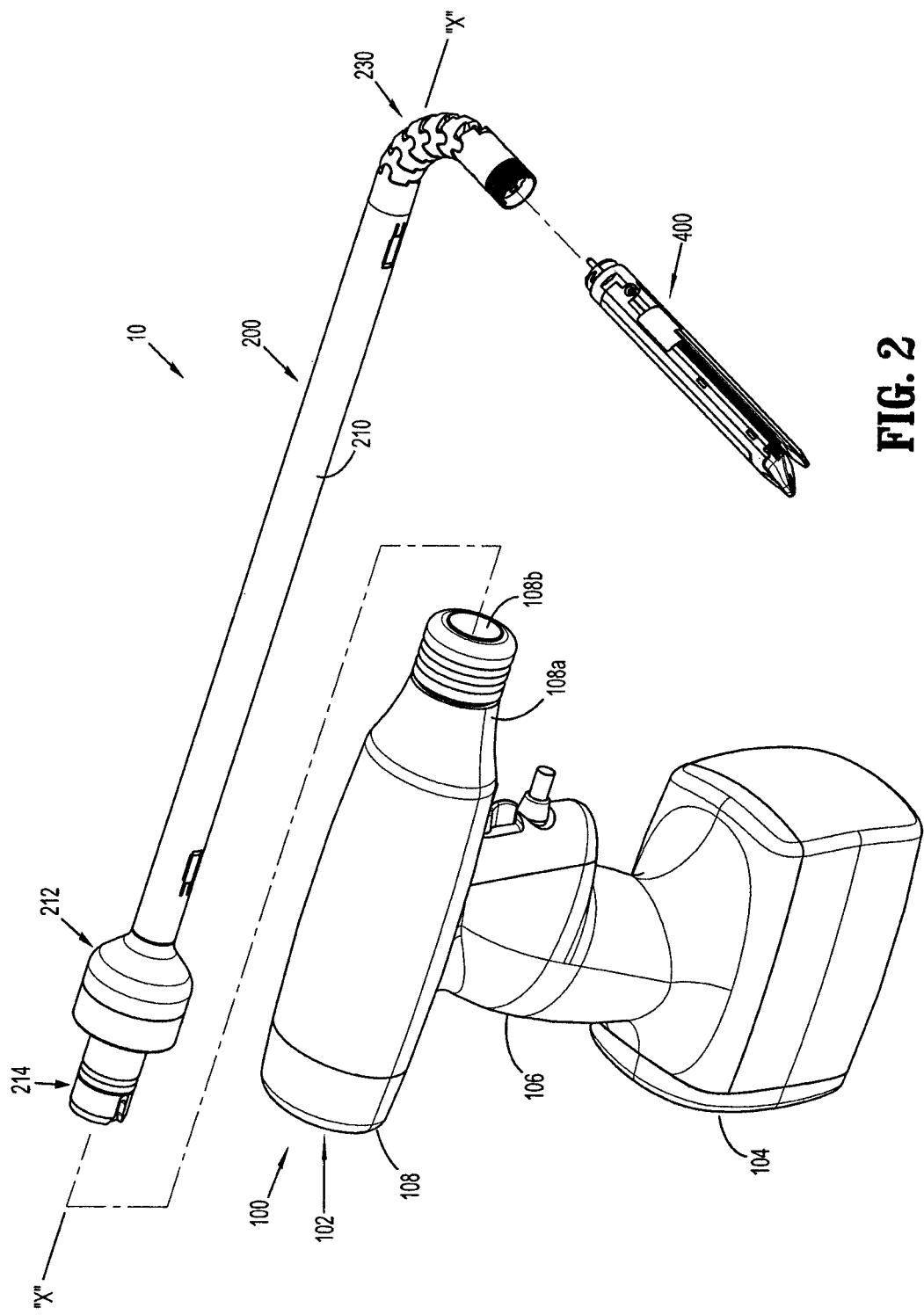
FIG. 2 is a perspective view, with parts separated, of the electromechanical surgical system of FIG. 1.
Figure 3:
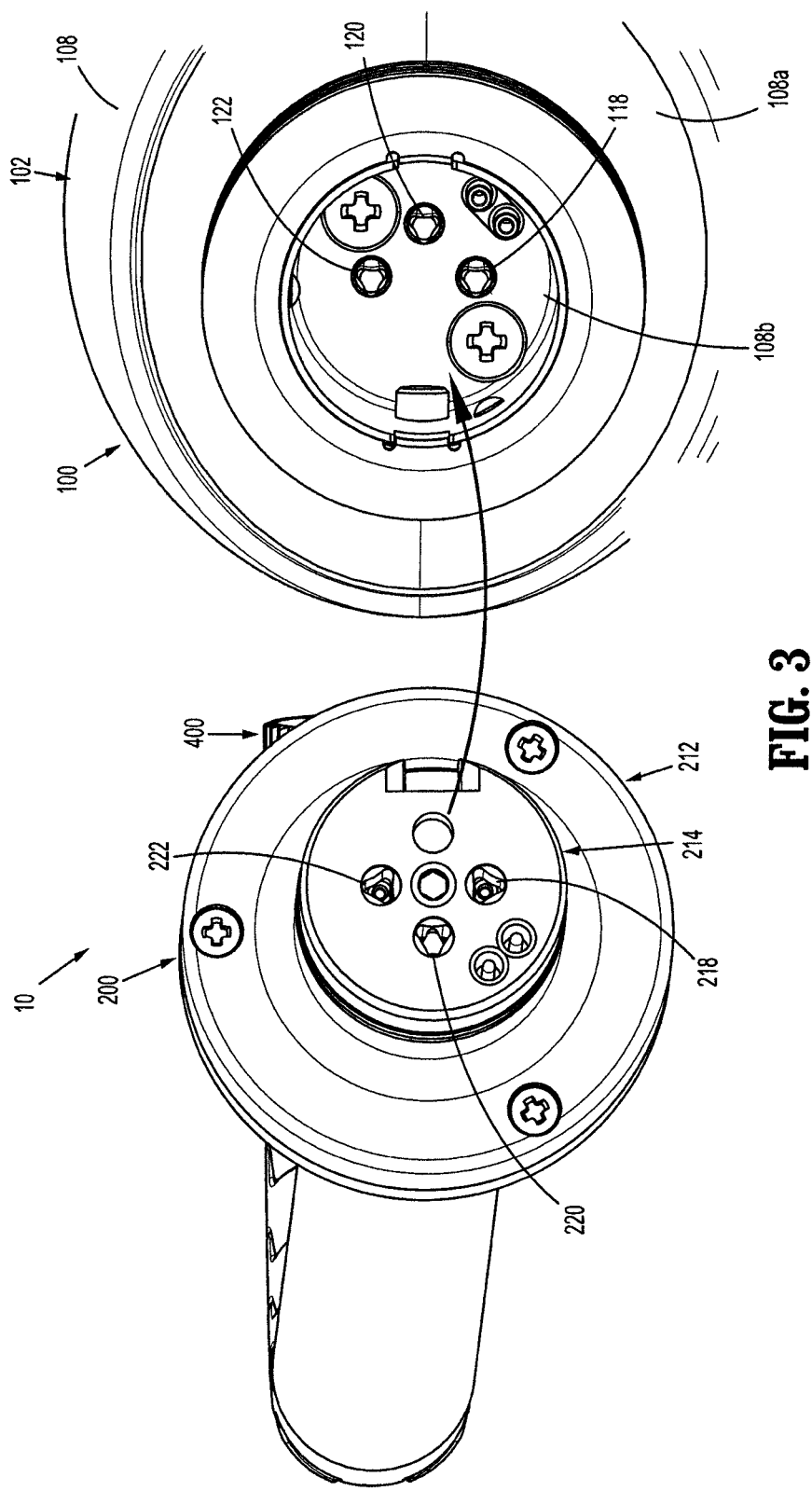
FIG. 3 is a rear, perspective view of a shaft assembly and a powered surgical instrument, of the electromechanical surgical system of FIGS. 1 and 2, illustrating a connection therebetween.

Referring initially to FIGS. 1-3, an electromechanical, hand-held, powered surgical system, in accordance with an embodiment of the present disclosure is shown and generally designated 10. Electromechanical surgical system 10 includes a surgical apparatus or device in the form of an electromechanical, hand-held, powered surgical instrument 100 that is configured for selective attachment thereto of a plurality of different end effectors 400, via a shaft assembly 200, that are each configured for actuation and manipulation by the electromechanical, hand-held, powered surgical instrument 100. In particular, surgical instrument 100 is configured for selective connection with shaft assembly 200, and, in turn, shaft assembly 200 is configured for selective connection with any one of a plurality of different end effectors 400.

Reference may be made to International Application No. PCT/US2008/077249, filed Sep. 22, 2008 (Inter. Pub. No. WO 2009/039506) and U.S. patent application Ser. No. 12/622,827, filed on Nov. 20, 2009, the entire content of each of which are hereby incorporated herein by reference, for a detailed description of the construction and operation of exemplary electromechanical, hand-held, powered surgical instrument 100

Generally, as illustrated in FIGS. 1-3, surgical instrument 100 includes an instrument housing 102 having a lower housing portion 104, an intermediate housing portion 106 extending from and/or supported on lower housing portion 104, and an upper housing portion 108 extending from and/or supported on intermediate housing portion 106. The surgical instrument 100 has a controller for controlling certain functions of the surgical system, collecting data, and performing other functions. Instrument housing 102 defines a cavity therein in which a circuit board (not shown) and a drive mechanism (not shown) are situated.

The circuit board is configured to control the various operations of surgical instrument 100, as will be set forth in additional detail below. In accordance with the present disclosure, instrument housing 102 provides a housing in which a rechargeable battery (not shown), is removably situated. The battery is configured to supply power to any of the electrical components of surgical instrument 100.

Upper housing portion 108 of instrument housing 102 defines a nose or connecting portion 108a configured to accept a corresponding shaft coupling assembly 214 of transmission housing 212 of shaft assembly 200. As seen in FIG. 3, connecting portion 108a of upper housing portion 108 of surgical instrument 100 has a cylindrical recess 108b that receives shaft coupling assembly 214 of transmission housing 212 of shaft assembly 200 when shaft assembly 200 is mated to surgical instrument 100. The connecting portion 108a of the surgical instrument 100 has at least one rotatable drive member. In particular, connecting portion 108a houses three rotatable drive members or connectors 118, 120, 122, each independently actuatable and rotatable by the drive mechanism (not shown) housed within instrument housing 102.

Upper housing portion 108 of instrument housing 102 provides a housing in which the drive mechanism (not shown) is situated. The drive mechanism is configured to drive shafts and/or gear components in order to perform the various operations of surgical instrument 100. In particular, the drive mechanism is configured to drive shafts and/or gear components in order to selectively move end effector 400 relative to shaft assembly 200; to rotate anvil assembly 200 and/or end effector 400, about a longitudinal axis "X" (see FIGS. 1 and 2), relative to instrument housing 102; to move an upper jaw or anvil assembly 442 of end effector 400 relative to a lower jaw or cartridge assembly 432 of end effector 400; to articulate and/or rotate the shaft assembly; and/or to fire a stapling and cutting cartridge within cartridge assembly 432 of end effector 400.

The shaft assembly 200 has a force transmitting assembly for interconnecting the at least one drive member of the surgical instrument to at least one rotation receiving member of the end effector. The force transmitting assembly has a first end that is connectable to the at least one rotatable drive member and a second end that is connectable to the at least one rotation receiving member of the end effector. When shaft assembly 200 is mated to surgical instrument 100, each of rotatable drive members or connectors 118, 120, 122 of surgical instrument 100 couples with a corresponding rotatable connector sleeve 218, 220, 222 of shaft assembly 200 (see FIGS. 3 and 5). In this regard, the interface between corresponding first drive member or connector 118 and first connector sleeve 218, the interface between corresponding second drive member or connector 120 and second connector sleeve 220, and the interface between corresponding third drive member or connector 122 and third connector sleeve 222 are keyed such that rotation of each of drive members or connectors 118, 120, 122 of surgical instrument 100 causes a corresponding rotation of the corresponding connector sleeve 218, 220, 222 of shaft assembly 200.

The mating of drive members or connectors 118, 120, 122 of surgical instrument 100 with connector sleeves 218, 220, 222 of shaft assembly 200 allows rotational forces to be independently transmitted via each of the three respective connector interfaces. The drive members or connectors 118, 120, 122 of surgical instrument 100 are configured to be independently rotated by the drive mechanism. In this regard, the controller has a function selection module (not shown) of the drive mechanism selects which drive member or connector 118, 120, 122 of surgical instrument 100 is to be driven by an input drive component (not shown) of the drive mechanism.

Since each of drive members or connectors 118, 120, 122 of surgical instrument 100 has a keyed and/or substantially non-rotatable interface with respective connector sleeves 218, 220, 222 of shaft assembly 200, when shaft assembly 200 is coupled to surgical instrument 100, rotational force(s) are selectively transferred from the drive mechanism of surgical instrument 100 to shaft assembly 200, and on to end effector 400, as will be discussed in greater detail below.

The selective rotation of drive member(s) or connector(s) 118, 120 and/or 122 of surgical instrument 100 allows surgical instrument 100 to selectively actuate different functions of end effector 400. As will be discussed in greater detail below, selective and independent rotation of first drive member or connector 118 of surgical instrument 100 corresponds to the selective and independent opening and closing of end effector 400, and driving of a stapling/cutting component of end effector 400. Also, the selective and independent rotation of second drive member or connector 120 of surgical instrument 100 corresponds to the selective and independent articulation of end effector 400 transverse to longitudinal axis "X" (see FIG. 1). Additionally, the selective and independent rotation of third drive member or connector 122 of surgical instrument 100 corresponds to the selective and independent rotation of end effector 400 about longitudinal axis "X" (see FIG. 1) relative to instrument housing 102 of surgical instrument 100.

In accordance with the present disclosure, the drive mechanism may include a selector gearbox assembly (not shown); a function selection module (not shown), located proximal to the selector gearbox assembly, that functions to selectively move gear elements within the selector gearbox assembly into engagement with a second motor (not shown). The drive mechanism may be configured to selectively drive one of drive members or connectors 118, 120, 122 of surgical instrument 100, at a given time.

As illustrated in FIGS. 1 and 2, instrument housing 102 supports a pair of finger-actuated control buttons 124, 126 and/or rocker device(s) 130 (only one rocker device being shown). Each one of the control buttons 124, 126 and rocker device(s) 130 includes a respective magnet (not shown) that is moved by the actuation of an operator. In addition, the circuit board (not shown) housed in instrument housing 102 includes, for each one of the control buttons 124, 126 and rocker device(s) 130, respective Hall-effect switches (not shown) that are actuated by the movement of the magnets in the control buttons 124, 126 and rocker device(s) 130. In particular, located immediately proximal to the control button 124 is a respective Hall-effect switch (not shown) that is actuated upon the movement of a magnet within the control button 124 upon the operator actuating control button 124. The actuation of Hall-effect switch (not shown), corresponding to control button 124, causes the circuit board to provide appropriate signals to the function selection module and the input drive component of the drive mechanism to close end effector 400 and/or to fire a stapling/cutting cartridge within end effector 400.

Also, located immediately proximal to control button 126 is a respective Hall-effect switch (not shown) that is actuated upon the movement of a magnet (not shown) within control button 126 upon the operator actuating control button 126. The actuation of the Hall-effect switch, corresponding to control button 126, causes the circuit board to provide appropriate signals to the function selection module and the input drive component of the drive mechanism to open/close end effector 400.

In addition, located immediately proximal to rocker device 130 is a respective Hall-effect switch (not shown) that is actuated upon the movement of a magnet (not shown) within rocker device 130 upon the operator actuating rocker device 130. The actuation of the Hall-effect switch, corresponding to rocker device 130, causes the circuit board to provide appropriate signals to the function selection module and the input drive component of the drive mechanism to rotate end effector 400 relative to shaft assembly 200 or rotate end effector 400 and shaft assembly 200 relative to instrument housing 102 of surgical instrument 100. Specifically, movement of rocker device 130 in a first direction causes end effector 400 and/or shaft assembly 200 to rotate relative to instrument housing 102 in a first direction, while movement of rocker device 130 in an opposite, e.g., second, direction causes end effector 400 and/or shaft assembly 200 to rotate relative to instrument housing 102 in an opposite, e.g., second, direction.

Turning now to FIGS. 1-26, shaft assembly 200 will be shown in detail and described. Shaft assembly 200 is configured to communicate the rotational forces of first, second and third rotatable drive members or connectors 118, 120, and 122 of surgical instrument 100 to end effector 400. As mentioned above, shaft assembly 200 is configured for selective connection to surgical instrument 100.

Figure 4:
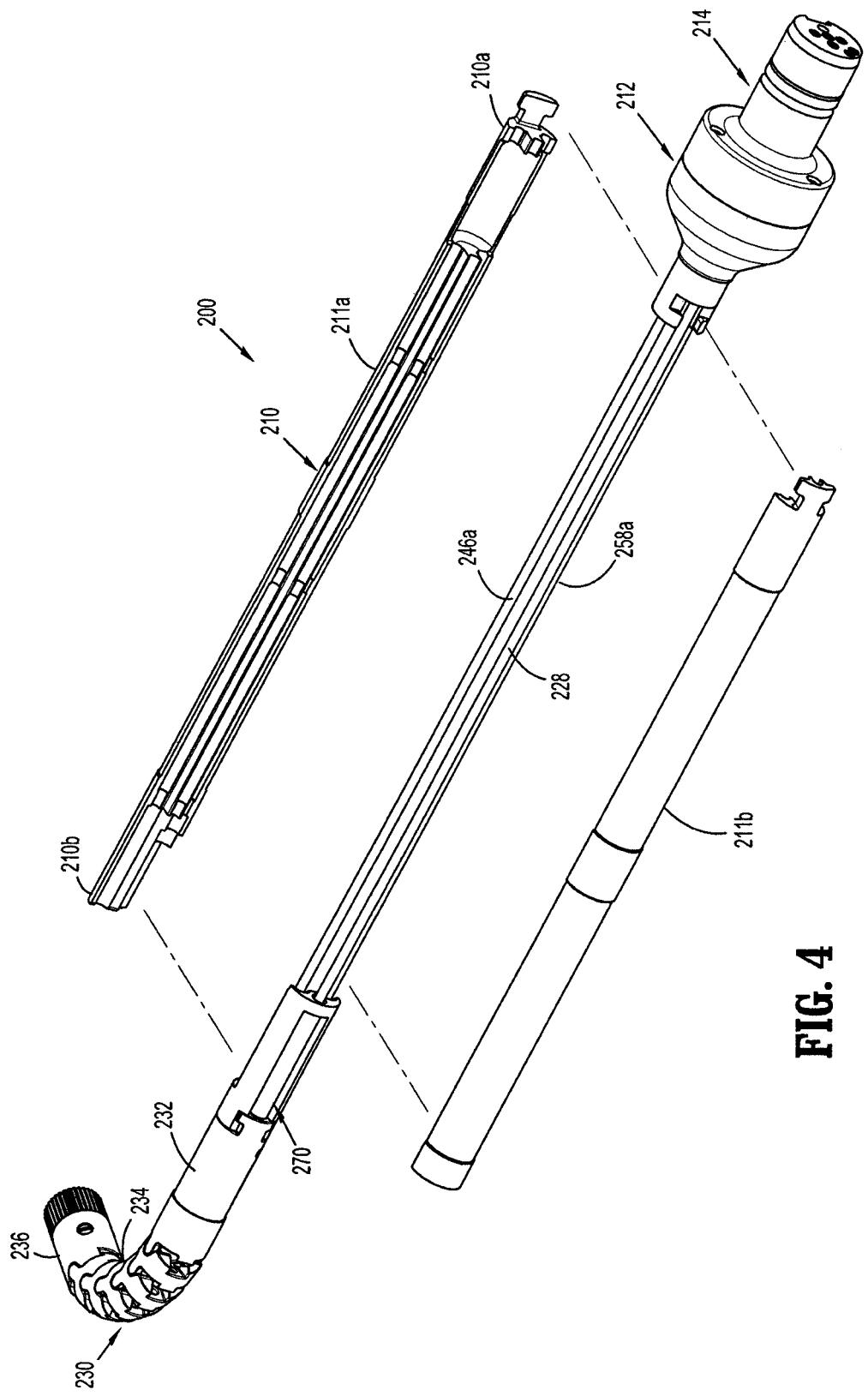
FIG. 4 is a perspective view, with parts separated, of the shaft assembly of FIGS. 1-3.

As seen in FIGS. 1, 2 and 4, shaft assembly 200 includes an elongate, substantially rigid, outer tubular body 210 having a proximal end 210a and a distal end 210b; a transmission housing 212 connected to proximal end 210a of tubular body 210 and being configured for selective connection to surgical instrument 100; and an articulating neck assembly 230 connected to distal end 210b of elongate body portion 210.

Transmission housing 212 is configured to house a pair of gear train systems therein for varying a speed/force of rotation (e.g., increase or decrease) of first, second and/or third rotatable drive members or connectors 118, 120, and/or 122 of surgical instrument 100 before transmission of such rotational speed/force to end effector 400.

Figure 5:
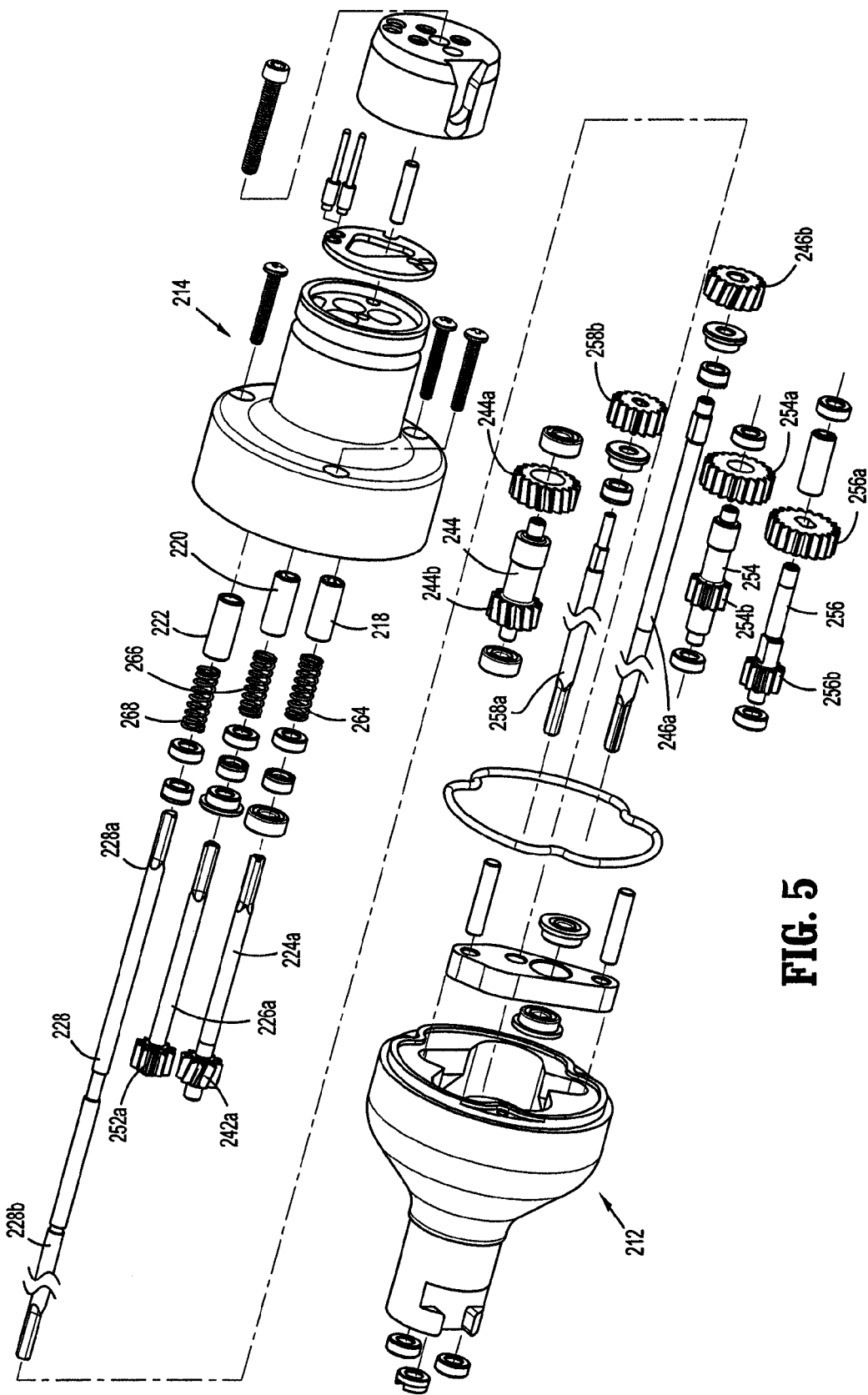
FIG. 5 is a perspective view, with parts separated of a transmission housing of the shaft assembly.

Transmission housing 212 of shaft assembly 200 is configured and adapted to connect to connecting portion 108a of upper housing portion 108 of surgical instrument 100. As seen in FIGS. 3-5, transmission housing 212 of shaft assembly 200 includes a shaft coupling assembly 214 supported at a proximal end thereof.

As seen in FIGS. 5 and 20-25, transmission housing 212 and shaft coupling assembly 214 rotatably support a first proximal or input drive shaft 224a, a second proximal or input drive shaft 226a, and a third drive shaft 228.

Shaft coupling assembly 214 is configured to rotatably support first, second and third connector sleeves 218, 220 and 222, respectively. Each of connector sleeves 218, 220, 222 is configured to mate with respective first, second and third drive members or connectors 118, 120, 122 of surgical instrument 100, as described above. Each of connector sleeves 218, 220, 222 is further configured to mate with a proximal end of respective first input drive shaft 224a, second input drive shaft 226a, and third drive shaft 228.

Shaft drive coupling assembly 214 includes a first, a second and a third biasing member 264, 266 and 268 disposed distally of respective first, second and third connector sleeves 218, 220, 222. Each of biasing members 264, 266 and 268 is disposed about respective first proximal drive shaft 224a, second proximal drive shaft 226a, and third drive shaft 228. Biasing members 264, 266 and 268 act on respective connector sleeves 218, 220 and 222 to help maintain connector sleeves 218, 220 and 222 engaged with the distal end of respective drive rotatable drive members or connectors 118, 120, 122 of surgical instrument 100 when shaft assembly 200 is connected to surgical instrument 100.

In particular, first, second and third biasing members 264, 266 and 268 function to bias respective connector sleeves 218, 220 and 222 in a proximal direction. In this manner, during connection of shaft assembly 200 to surgical instrument 100, if first, second and or third connector sleeves 218, 220 and/or 222 is/are misaligned with the drive members or connectors 118, 120, 122 of surgical instrument 100, first, second and/or third biasing member(s) 264, 266 and/or 268 are compressed. Thus, when the drive mechanism of surgical instrument 100 is engaged, drive members or connectors 118, 120, 122 of surgical instrument 100 will rotate and first, second and/or third biasing member(s) 264, 266 and/or 268 will cause respective first, second and/or third connector sleeve(s) 218, 220 and/or 222 to slide back proximally, effectively coupling drive members or connectors 118, 120, 122 of surgical instrument 100 to respective first input drive shaft 224a, second input drive shaft 226a, and third drive shaft 228.

In use, during a calibration of surgical instrument 100, each of drive connectors 118, 120, 122 of surgical instrument 100 is rotated and the bias on connector sleeve(s) 218, 220 and 222 properly seats connector sleeve(s) 218, 220 and 222 over the respective drive connectors 118, 120, 122 of surgical instrument 100 when the proper alignment is reached.

Shaft assembly 200 includes a first and a second gear train system 240, 250, respectively, disposed within transmission housing 212 and tubular body 210, and adjacent coupling assembly 214. As mentioned above, each gear train system 240, 250 is configured and adapted to vary a speed/force of rotation (e.g., increase or decrease) of first and second rotatable drive connectors 118 and 120 of surgical instrument 100 before transmission of such rotational speed/force to end effector 400.

Figure 6:
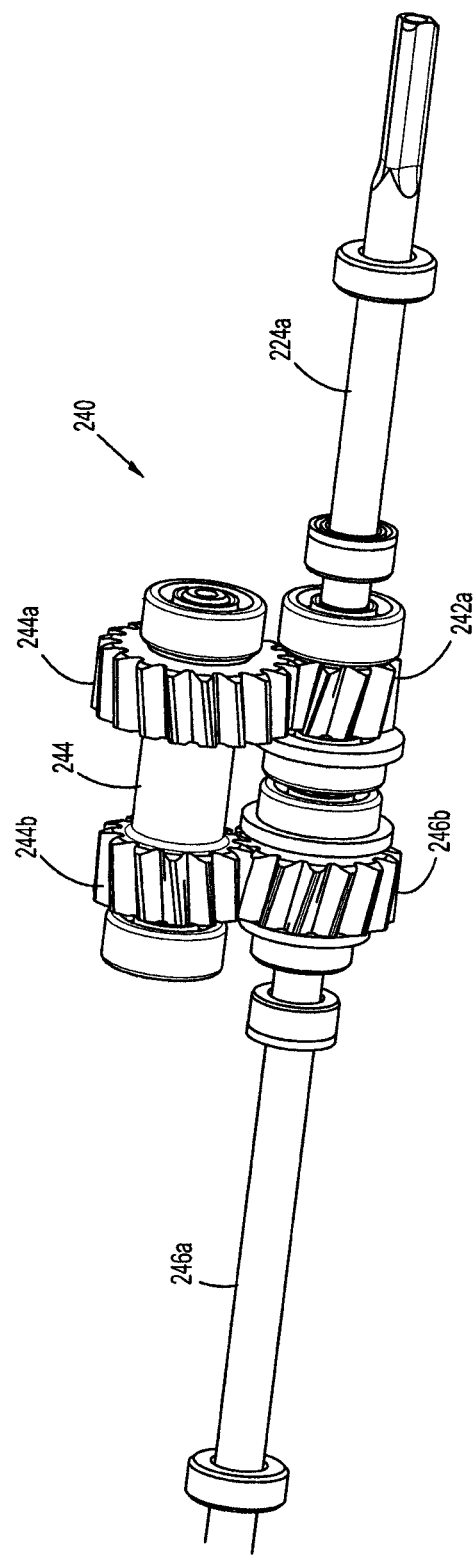
FIG. 6 is a perspective view of a first gear train system that is supported in the transmission housing.

As seen in FIGS. 5 and 6, first gear train system 240 includes first input drive shaft 224a, and a first input drive shaft spur gear 242a keyed to first input drive shaft 224a. First gear train system 240 also includes a first transmission shaft 244 rotatably supported in transmission housing 212, a first input transmission spur gear 244a keyed to first transmission shaft 244 and engaged with first input drive shaft spur gear 242a, and a first output transmission spur gear 244b keyed to first transmission shaft 244. First gear train system 240 further includes a first output drive shaft 246a rotatably supported in transmission housing 212 and tubular body 110, and a first output drive shaft spur gear 246b keyed to first output drive shaft 246a and engaged with first output transmission spur gear 244b.

In accordance with the present disclosure, first input drive shaft spur gear 242a includes 10 teeth; first input transmission spur gear 244a includes 18 teeth; first output transmission spur gear 244b includes 13 teeth; and first output drive shaft spur gear 246b includes 15 teeth. As so configured, an input rotation of first input drive shaft 224a is converted to an output rotation of first output drive shaft 246a by a ratio of 1:2.08.

As mentioned above, a proximal end of first input drive shaft 224a is configured to support first connector sleeve 218.

In operation, as first input drive shaft spur gear 242a is rotated, due to a rotation of first connector sleeve 258 and first input drive shaft 224a, as a result of the rotation of the first respective drive connector 118 of surgical instrument 100, first input drive shaft spur gear 242a engages first input transmission spur gear 244a causing first input transmission spur gear 244a to rotate. As first input transmission spur gear 244a rotates, first transmission shaft 244 is rotated and thus causes first output drive shaft spur gear 246b, that is keyed to first transmission shaft 244, to rotate. As first output drive shaft spur gear 246b rotates, since first output drive shaft spur gear 246b is engaged therewith, first output drive shaft spur gear 246b is also rotated. As first output drive shaft spur gear 246b rotates, since first output drive shaft spur gear 246b is keyed to first output drive shaft 246a, first output drive shaft 246a is rotated.

As will be discussed in greater detail below, shaft assembly 200, including first gear system 240, functions to transmit operative forces from surgical instrument 100 to end effector 400 in order to operate, actuate and/or fire end effector 400.

Figure 7:
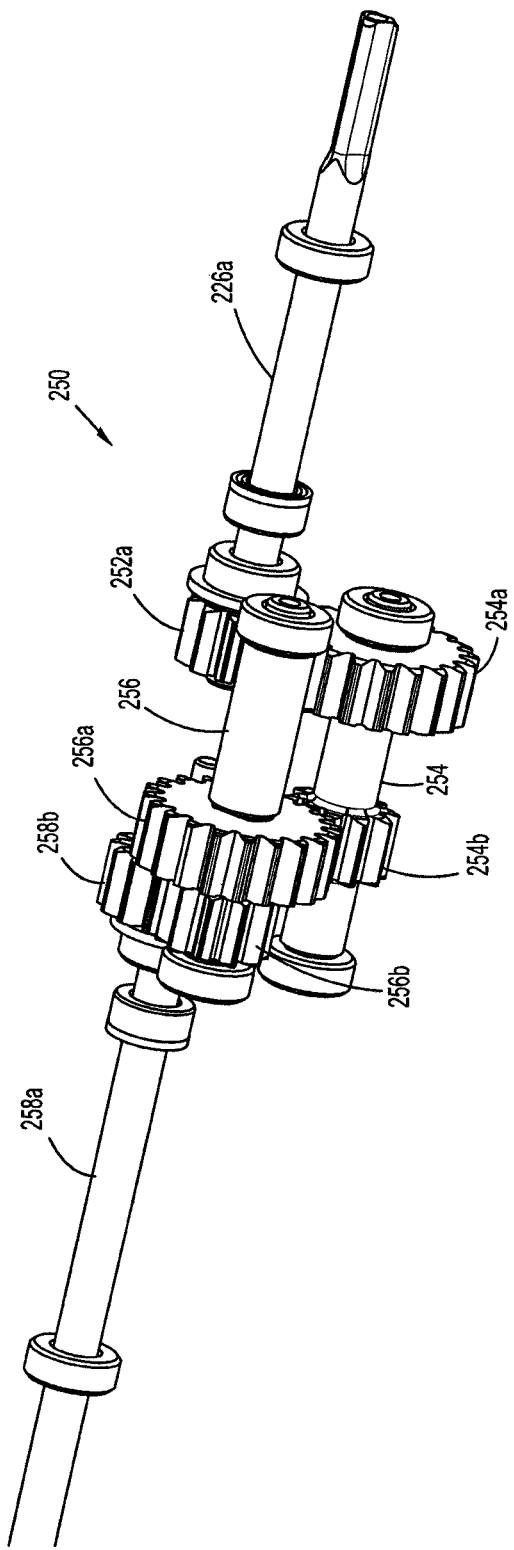
FIG. 7 is a perspective view of a second gear train system that is supported in the transmission housing.
Figure 8:
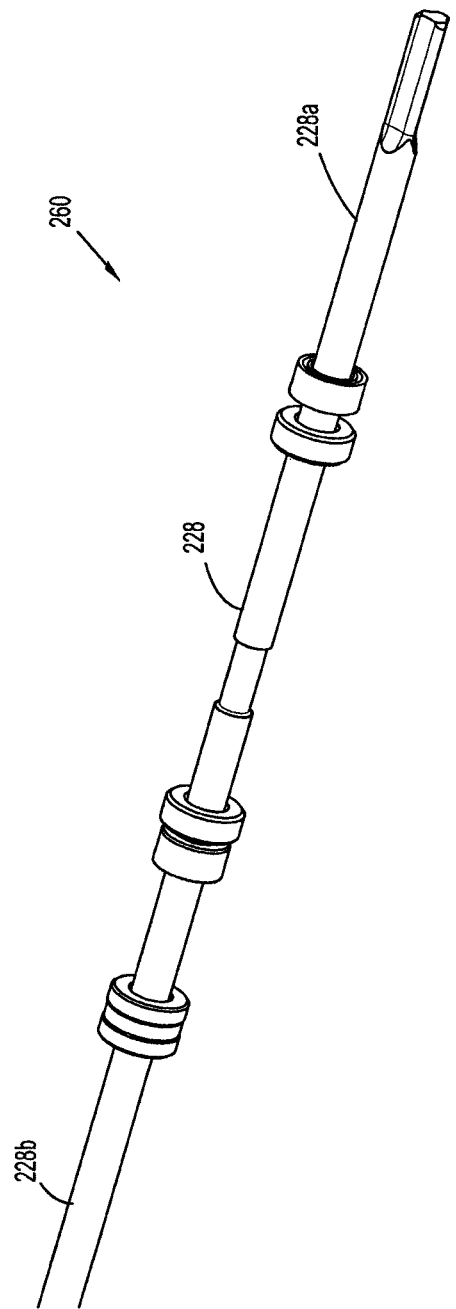
FIG. 8 is a perspective view of a third drive shaft that is supported in the transmission housing.
Figure 11:
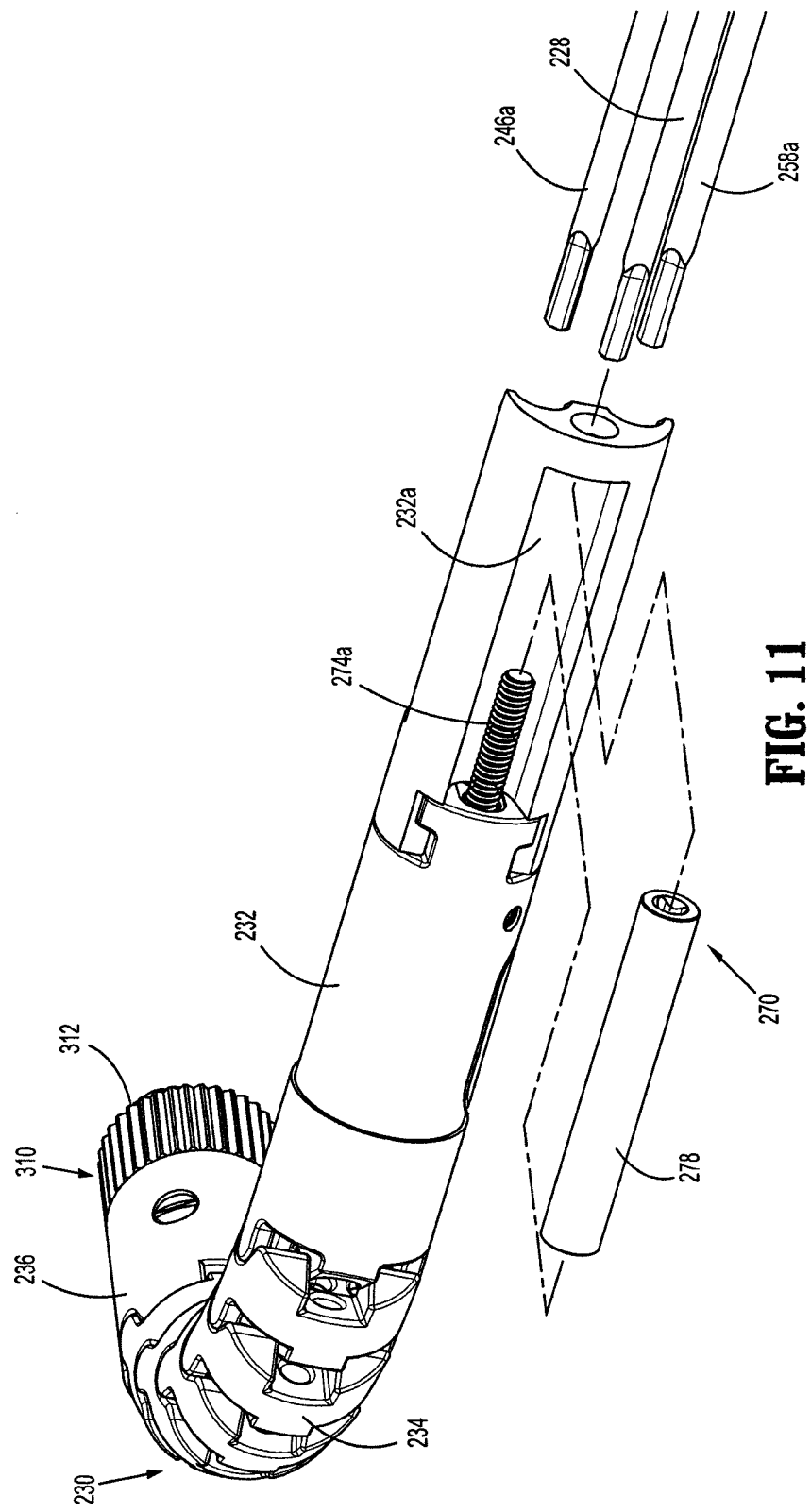
FIG. 11 is a perspective view of the neck assembly of FIGS. 9 and 10, with a threaded nut separated therefrom.

As seen in FIGS. 5 and 7, second gear train system 250 includes second input drive shaft 226a, and a second input drive shaft spur gear 252a keyed to second input drive shaft 226a. Second gear train system 250 also includes a first transmission shaft 254 rotatably supported in transmission housing 212, a first input transmission spur gear 254a keyed to first transmission shaft 254 and engaged with second input drive shaft spur gear 252a, and a first output transmission spur gear 254b keyed to first transmission shaft 254.

Second gear train system 250 further includes a second transmission shaft 256 rotatably supported in transmission housing 212, a second input transmission spur gear 256a keyed to second transmission shaft 256 and engaged with first output transmission spur gear 254b that is keyed to first transmission shaft 254, and a second output transmission spur gear 256b keyed to second transmission shaft 256.

Second gear train system 250 additionally includes a second output drive shaft 258a rotatably supported in transmission housing 212 and tubular body 210, and a second output drive shaft spur gear 258b keyed to second output drive shaft 258a and engaged with second output transmission spur gear 256b.

In accordance with the present disclosure, second input drive shaft spur gear 252a includes 10 teeth; first input transmission spur gear 254a includes 20 teeth; first output transmission spur gear 254b includes 10 teeth; second input transmission spur gear 256a includes 20 teeth; second output transmission spur gear 256b includes 10 teeth; and second output drive shaft spur gear 258b includes 15 teeth. As so configured, an input rotation of second input drive shaft 226a is converted to an output rotation of second output drive shaft 258a by a ratio of 1:6.

As mentioned above, a proximal end of second input drive shaft 226a is configured to support second connector sleeve 220.

In operation, as second input drive shaft spur gear 252a is rotated, due to a rotation of second connector sleeve 260 and second input drive shaft 226a, as a result of the rotation of the second respective drive connector 120 of surgical instrument 100, second input drive shaft spur gear 252a engages first input transmission spur gear 254a causing first input transmission spur gear 254a to rotate. As first input transmission spur gear 254a rotates, first transmission shaft 254 is rotated and thus causes first output transmission spur gear 254b, that is keyed to first transmission shaft 254, to rotate. As first output transmission spur gear 254b rotates, since second input transmission spur gear 256a is engaged therewith, second input transmission spur gear 256a is also rotated. As second input transmission spur gear 256a rotates, second transmission shaft 256 is rotated and thus causes second output transmission spur gear 256b, that is keyed to second transmission shaft 256, to rotate. As second output transmission spur gear 256b rotates, since second output drive shaft spur gear 258b is engaged therewith, second output drive shaft spur gear 258b is rotated. As second output drive shaft spur gear 258b rotates, since second output drive shaft spur gear 258b is keyed to second output drive shaft 258a, second output drive shaft 258a is rotated.

As will be discussed in greater detail below, shaft assembly 200, including second gear train system 250, functions to transmit operative forces from surgical instrument 100 to end effector 400 in order rotate shaft assembly 200 and/or end effector 400 relative to surgical instrument 100.

As mentioned above and as seen in FIGS. 5 and 8, transmission housing 212 and shaft coupling assembly 214 rotatably support a third drive shaft 228. Third drive shaft 228 includes a proximal end 228a configured to support third connector sleeve 222, and a distal end 228b extending to and operatively connected to an articulation assembly 270 as will be discussed in greater detail below.

As seen in FIG. 4, elongate, outer tubular body 210 of shaft assembly 200 includes a first half section 211a and a second half section 211b defining at least three longitudinally extending channels through outer tubular body 210 when half sections 211a, 211b are mated with one another. The channels are configured and dimensioned to rotatably receive and support first output drive shaft 246a, second output drive shaft 258a, and third drive shaft 228 as first output drive shaft 246a, second output drive shaft 258a, and third drive shaft 228 extend from transmission housing 212 to articulating neck assembly 230. Each of first output drive shaft 246a, second output drive shaft 258a, and third drive shaft 228 are elongate and sufficiently rigid to transmit rotational forces from transmission housing 220 to articulating neck assembly 230.

Turning now to FIGS. 4 and 9-16, articulating neck assembly 230 is shown and described. Articulating neck assembly 230 includes a proximal neck housing 232, a plurality of links 234 connected to and extending in series from proximal neck housing 232; and a distal neck housing 236 connected to and extending from a distal-most link of the plurality of links 234.

Each link 234 includes cooperating knuckles and clevises formed on each of a proximal surface 234a and a distal surface 234b thereof. Proximal neck housing 232 includes knuckles and/or clevises that operatively engage with the knuckles and/or clevises of a proximal-most link. Distal neck housing 236 includes knuckles and/or clevises that operatively engage with the knuckles and/or clevises of a distal-most link. The knuckles and clevises of adjacent neck housings 232, 236 and links 234 operatively engage with one another to define a direction and a degree of articulation of neck assembly 230.

Neck assembly 230 is configured to enable end effector 400 to move between a substantially linear configuration and a substantially angled, off-axis or articulated configuration. In accordance with the present disclosure, it is contemplated that neck assembly 230 is capable of articulating in a single plane and is capable of articulating approximately 90°, and even greater than 90°.

Figure 12:
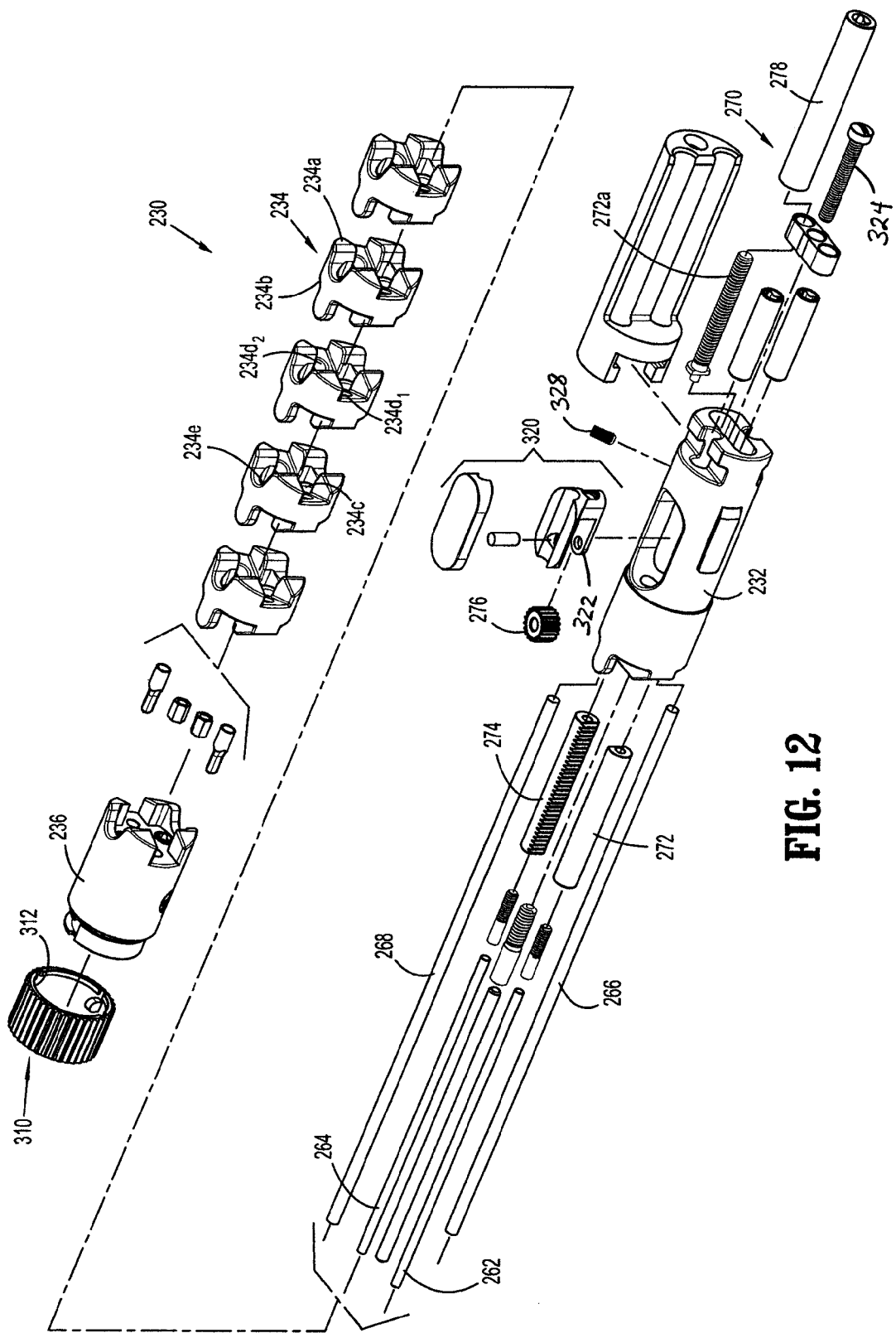
FIG. 12 is a perspective view, with parts separated, of the neck assembly of FIGS. 9-11.

Each link 234 defines a first lumen 234c (see FIG. 12) therein for passage of a first drive cable 266 therethrough; a first pair of opposed lumens 234$d_1$, 234$d_2$, for passage of a pair of articulation cables 262, 264 therethrough; and a second lumen 234e for passage of a second drive cable 268 therethrough. As seen in FIG. 12, first and second lumens 234c, 234e are diametrically opposed to one another and offset 90° relative to lumens 234$d_1$, 234$d_2$. Each of first drive cable 266 and second drive cable 268 includes a proximal end keyed to a distal end of respective first output drive shaft 246a and second output drive shaft 258a. Each of first and second drive cables 266, 268 is fabricated from a material that is both flexible and torsionally stiff (capable of transmitting rotational forces or torque), such as, for example, stainless steel and the like.

As seen in FIGS. 13-16, proximal neck housing 232 of neck assembly 230 supports an articulation assembly 270 configured and adapted to impart articulation to neck assembly 230 and/or end effector 400. Articulation assembly 270 includes a pair of opposed gear racks 272, 274 engaged with and on opposed sides of a pinion gear 276. Racks 272, 274 are axially slidably supported in proximal neck housing 232 and pinion gear 276 is rotatably supported in proximal neck housing 232.

Figure 13:
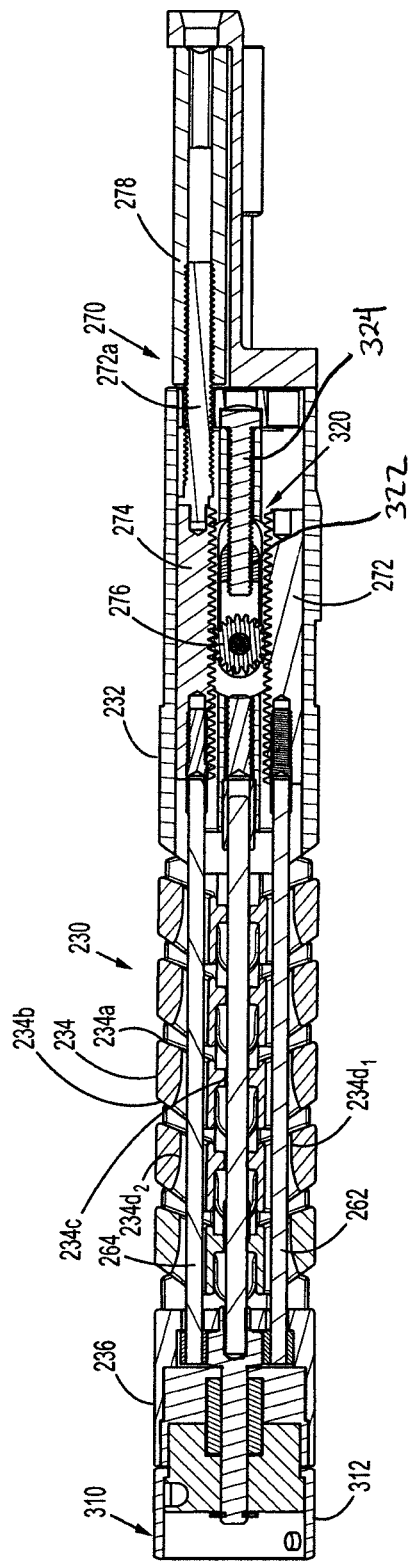
FIG. 13 is a cross-sectional view of the neck assembly of FIGS. 9-12, as taken through 13-13 of FIG. 9.
Figure 17:
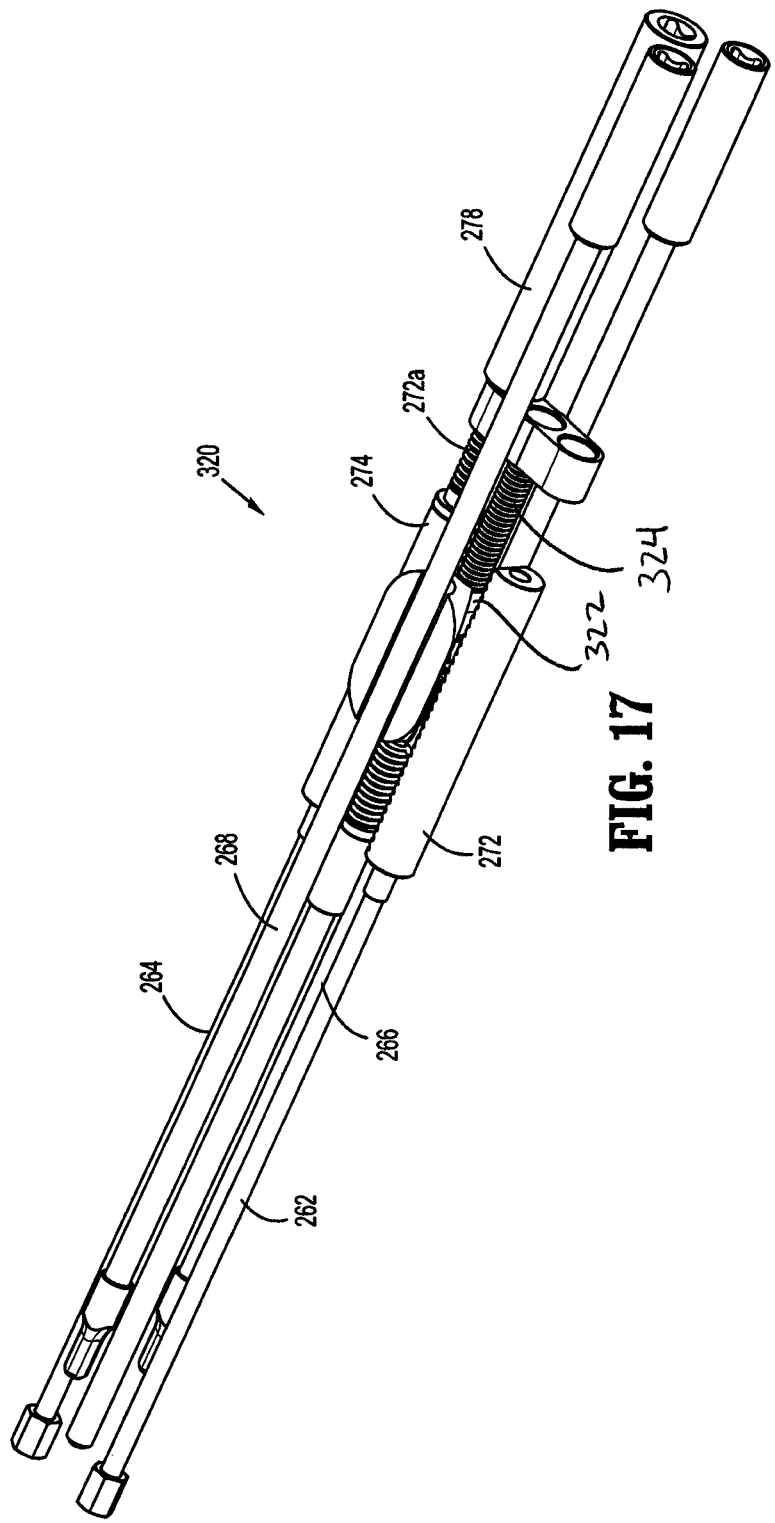
FIG. 17 is a perspective view of an articulation assembly.
Figure 18:
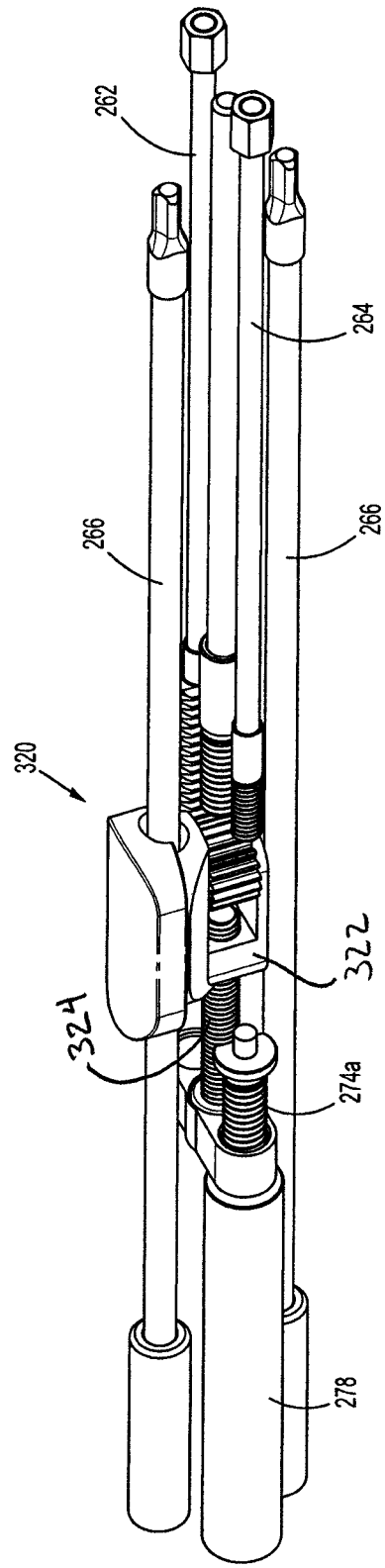
FIG. 18 is a further perspective view of the articulation assembly of FIG. 17.
Figure 19:
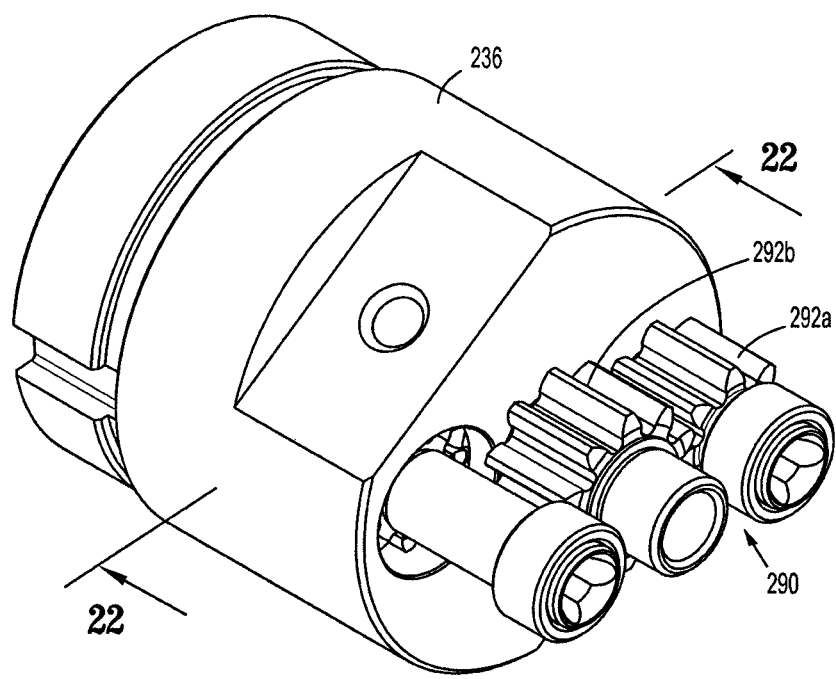
FIG. 19 is a perspective view of a second gear train that is supported in a distal neck housing of the neck assembly.
Figure 20:
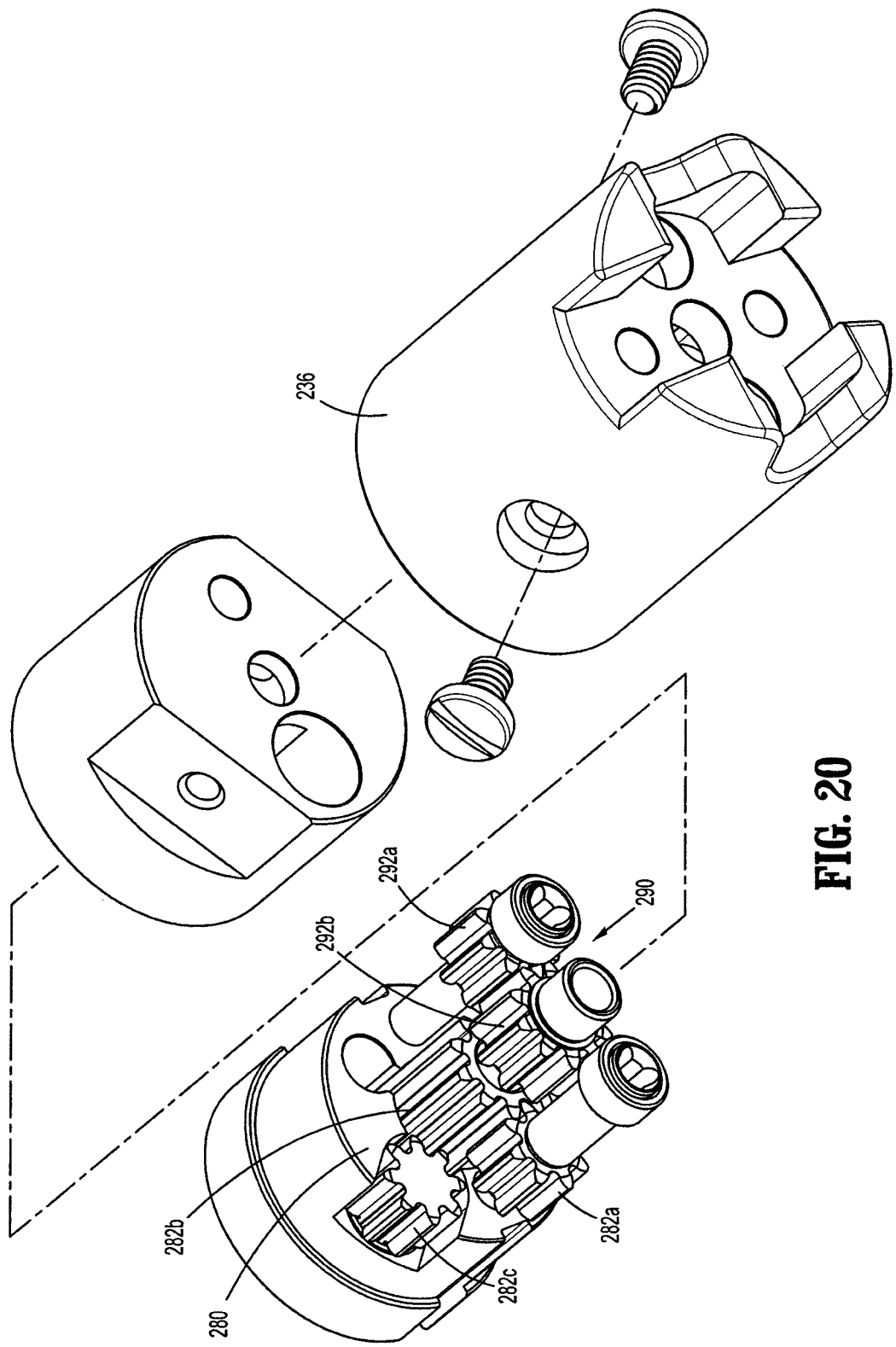
FIG. 20 is a perspective view, with parts partially separated, of a first gear train and the second gear train that are supported in a distal neck housing of the neck assembly.
Figure 21:
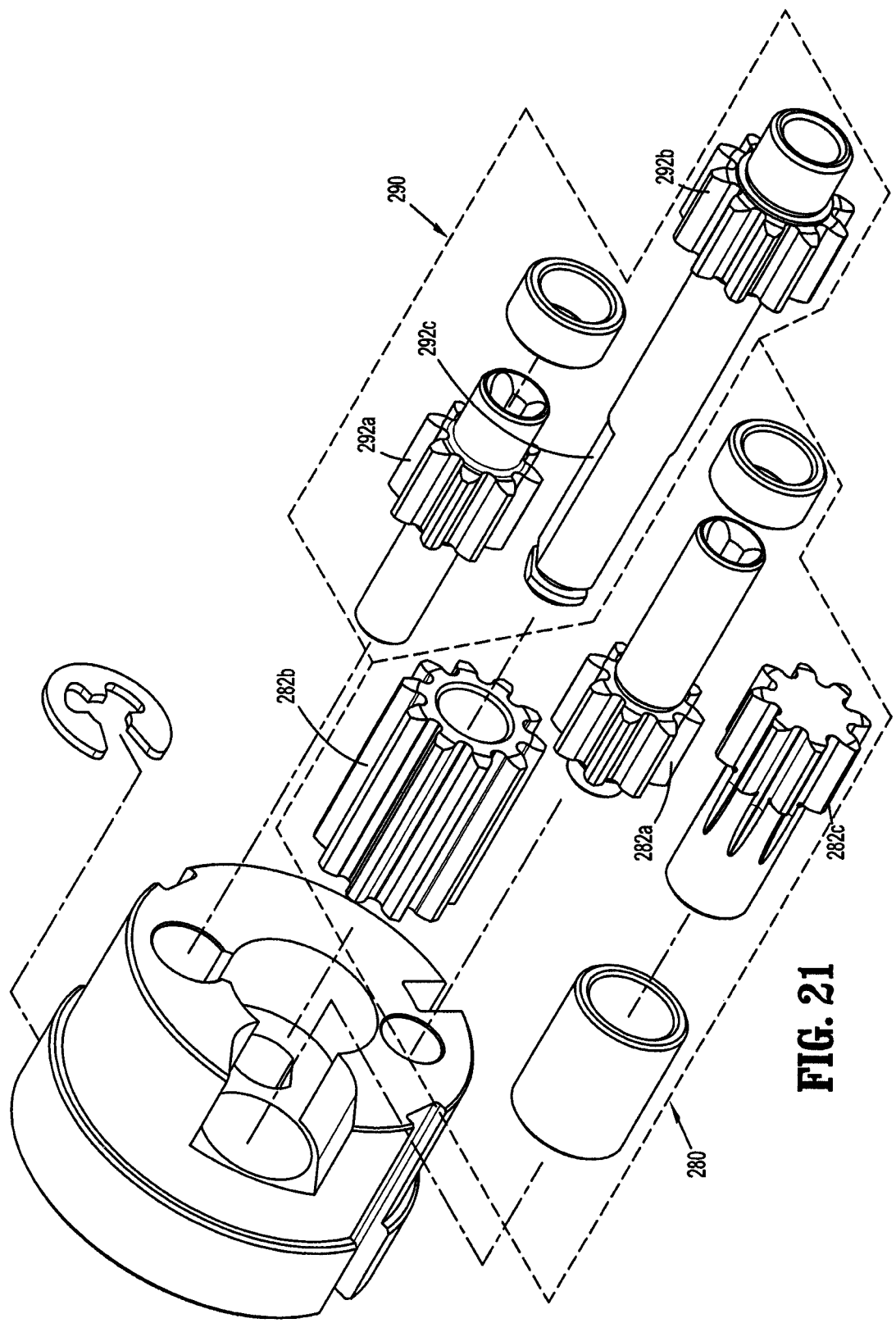
FIG. 21 is a perspective view, with parts partially separated, of the first gear train and the second gear train that are supported in a distal neck housing of the neck assembly.
Figure 24:
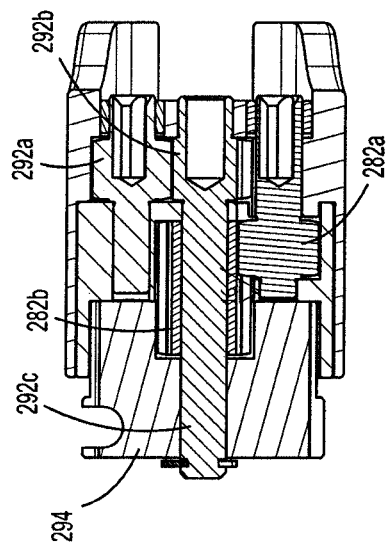
FIG. 24 is a cross-sectional view of the distal neck housing, as taken through 24-24 of FIG. 22.
Figure 25:
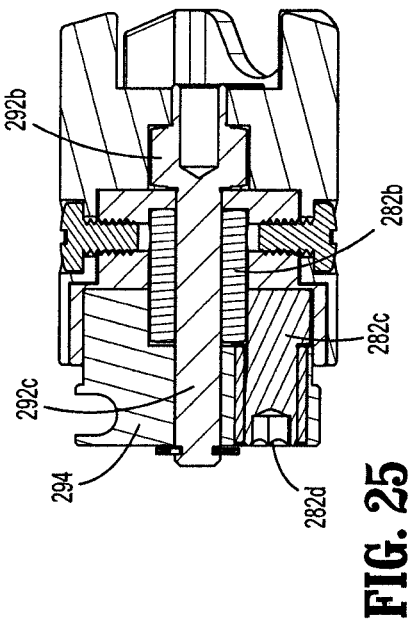
FIG. 25 is a cross-sectional view of the distal neck housing, as taken through 25-25 of FIG. 22.
Figure 23:
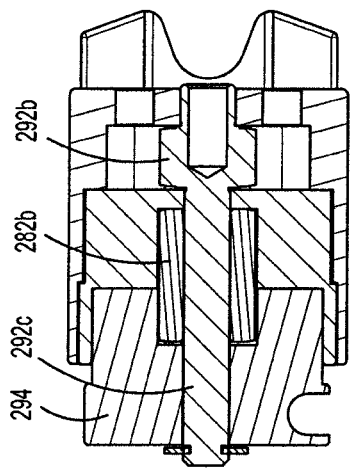
FIG. 23 is a cross-sectional view of the distal neck housing, as taken through 23-23 of FIG. 22.
Figure 22:
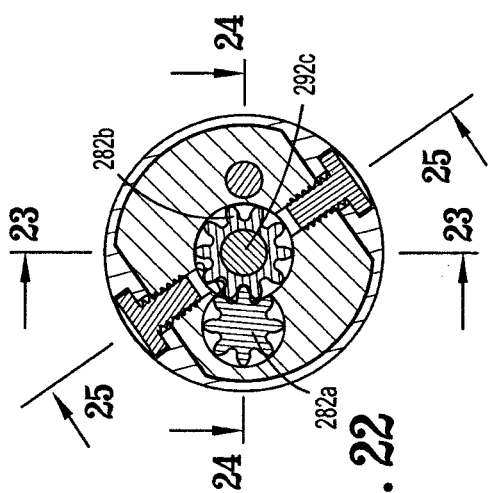
FIG. 22 is a cross-sectional view of the distal neck housing, as taken through 22-22 of FIG. 19.

As seen in FIGS. 12, 13 and 17, rack 274 is attached to a threaded shaft 272a extending proximally therefrom and that is in threaded engagement with a distal end of an internally threaded nut 278. Threaded nut 278 is rotatably supported and axially fixed within a pocket 232a formed in proximal neck housing 232. A proximal end of threaded nut 278 is keyed to a distal end of third drive shaft 228. While threaded shaft 272a is shown extending from rack 274, it is understood, and within the scope of the present disclosure, that the threaded shaft may extend from rack 272 without departing from the principles of the present disclosure.

Articulation cables 262, 264 include proximal ends that are secured to and extend from a respective distal end of racks 272, 274. Each articulation cable 262, 264 includes a distal end that extends through respective opposed lumens $234d_1$, $234d_2$ of links 234 and that is secured to or anchored in distal neck housing 234.

Figure 16:
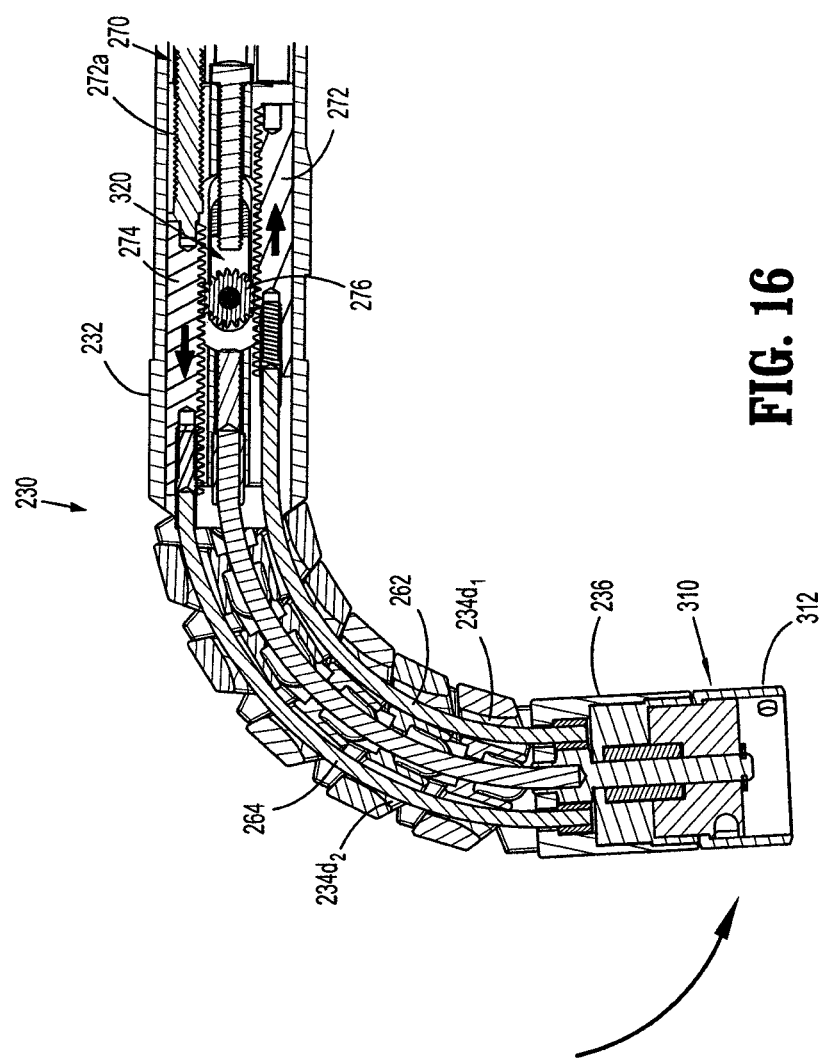
FIG. 16 is an illustration of the neck assembly of FIG. 13, shown in an articulated condition.

In operation, to articulate neck assembly 230 in a first direction, third drive shaft 228 is rotated in a first direction, as described above, to rotate threaded nut 278 and axially displace threaded shaft 272a distally to axially displace rack 274 distally (see FIG. 16). As rack 274 is displaced axially, in a distal direction, rack 274 causes pinion gear 276 to be rotated and to thus act on rack 272, to axially displace rack 272 in a proximal direction. As rack 272 is axially displaced in a proximal direction, rack 272 causes articulation cable 262 to be drawn in a proximal direction and thereby articulate neck assembly 230, as illustrated in FIG. 16. Neck assembly 230 is permitted to articulate since axially displacement of rack 274, in a distal direction, results in axial, distal displacement of articulation cable 264.

Distal neck housing 236 supports a first gear train 280 and a second gear train 290. First gear train 280 functions to transmit a rotation of first drive cable 266 to end effector 400. Second gear train 290 functions to transmit a rotation of second drive cable 268 to end effector 400.

As seen in FIGS. 20-25, first gear train 280 of distal neck housing 236 includes a first spur gear 282a rotatably supported in distal neck housing 236 and keyed to a distal end of first drive cable 266 of shaft assembly 200. First gear train 280 of distal neck housing 236 further includes a second spur gear 282b rotatably supported in distal neck housing 236 and engaged with first spur gear 282a. First gear train 280 of distal neck housing 236 also includes a third spur gear 282c rotatably supported in distal neck housing 236 and engaged with second spur gear 282b.

Figure 26:
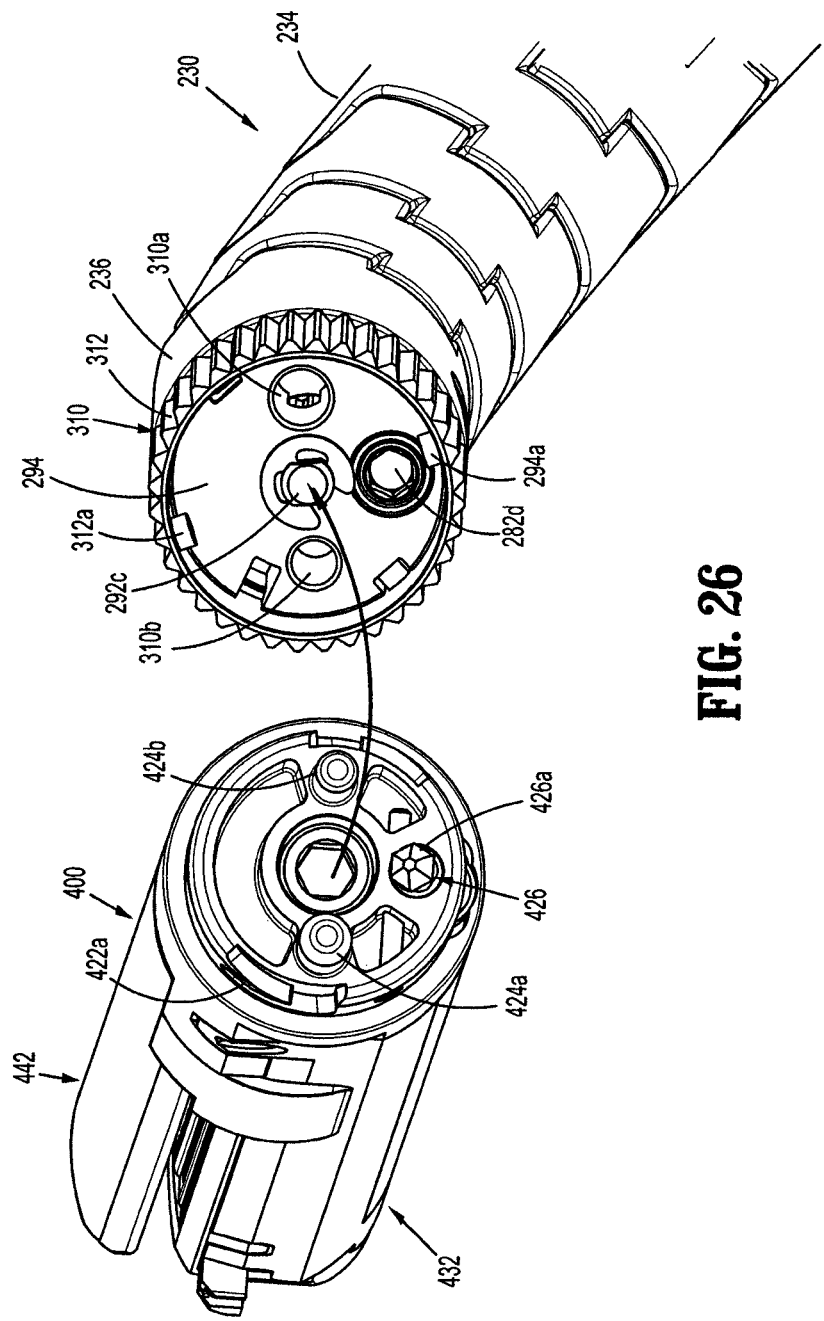
FIG. 26 is a rear, perspective view of the shaft assembly and an end effector, of the electromechanical surgical system of FIGS. 1 and 2, illustrating a connection therebetween.

Third spur gear 282c includes a bore 282d formed along a central axis thereof that is configured for mating receipt of a drive axle 426 of end effector 400 (see FIG. 26).

In accordance with the present disclosure, first spur gear 282a includes 8 teeth; second spur gear 282b includes 10 teeth; and third spur gear 282c includes 8 teeth. As so configured, an input rotation of first drive cable 266 is converted to an output rotation of third spur gear 282c of distal neck housing 236 by a ratio of 1:1. Additionally, first gear train 280 is provided to rotatably and mechanically connect first drive cable 266 to drive axle 426 of end effector 400.

In operation, as first drive cable 266 is rotated, due to a rotation of first output drive shaft 246a (as described above), said rotation is transmitted to first spur gear 282a of first gear train 280. As first spur gear 282a is rotated, third spur gear 282c, which has 8 teeth, is rotated due to the inter-engagement of first spur gear 282a (which functions as the input) and third spur gear 282c (which functions as the output) by second spur gear 282b (which functions as an idler gear). The second spur gear has 10 teeth. The gear ratio for this is 1:1. As third spur gear 282c is rotated, when end effector 400 is connected to shaft assembly 200, and specifically, third spur gear 282c is connected to drive axle 426 of end effector 400, a rotation of third spur gear 282c results in rotation of drive axle 426 of end effector 400 and actuation of end effector 400.

As seen in FIGS. 20-25, second gear train 290 of distal neck housing 236 includes a first spur gear 292a rotatably supported in distal neck housing 236 and keyed to a distal end of second drive cable 268 of shaft assembly 200. Second gear train 290 of distal neck housing 236 further includes a second spur gear 292b rotatably supported in distal neck housing 236 and engaged with first spur gear 292a. Second gear train 290 of distal neck housing 236 also includes a non-circular shaft 292c extending from second spur gear 292b (see FIG. 21). Non-circular shaft 292c is keyed to a rotation hub 294 such that rotation of non-circular shaft 292c results in rotation of rotation hub 294.

Rotation hub 294 is provided between a shaft of third spur gear 282c, of first gear train 280, that defines the bore 282d thereof and rotation hub 294 transmitting relative rotation of third spur gear 282c of first gear train 280 to rotation hub 294 of second gear train 290.

In accordance with the present disclosure, first spur gear 292a includes 8 teeth (which functions as the input); and second spur gear 292b includes 10 teeth. As so configured, an input rotation of second drive cable 268 is converted to an output rotation of rotation hub 294. The gear ratio for this is 1:0.8. Additionally, second gear train 290 is provided to rotatably and mechanically connect second drive axle 268 to rotation hub 294 of distal neck housing 236 of neck assembly 230.

In operation, as second drive cable 268 of shaft assembly 200 is rotated, due to a rotation of second output drive shaft 258a (as described above), said rotation is transmitted to first spur gear 292a of first gear train 290. As first spur gear 292a is rotated, non-circular shaft 292c is rotated due to its connection with second spur gear 292b. As non-circular shaft 292c is rotated, when end effector 400 is connected to shaft assembly 200, and specifically, rotation hub 294 is connected to alignment stems 424a, 424b of end effector 400, a rotation of rotation hub 294 results in rotation of end effector 400.

Shaft assembly 200 further includes an end effector coupling assembly 310 supported at a distal end of distal neck housing 236 of articulating neck assembly 230. End effector coupling assembly 310 includes a collar 312 rotatably supported on and extending distally from distal neck housing 236 and being biased to a first radial portion. Collar 312 is rotatable from a first radial position to a second radial position, wherein end effector 400 is matable to end effector coupling assembly 310, and returns, by way of the bias, to the first radial position, to lock end effector 400 to shaft assembly 200.

It is contemplated that collar 312 includes at least one nub 312a extending radially inward from inner surface thereof for receipt in a respective complementary structure 422a formed in an outer surface of end effector 400 to connect end effector 400 to shaft assembly 200 in the manner of a bayonet-type connection. Other forms of connection are contemplated, such as, detents, threaded connections, etc.

As seen in FIGS. 12-14, 17 and 18, shaft assembly 200 includes a cable tensioning assembly 320. Cable tensioning assembly 320 includes a clevis 322 slidably supported in proximal neck housing 232, for axial displacement therewithin. Clevis 322 rotatably supports pinion gear 276 of articulation assembly 270. Cable tensioning assembly 320 includes an adjustment screw 324, rotatably supported in proximal neck housing 232 and retained against axial displacement. Adjustment screw 324 is threadably connected to clevis 322 such that rotation of adjustment screw 324 results in axial displacement of clevis 322.

In operation, during an assembly of shaft assembly 200, an operator rotates adjustment screw 324 in a direction so as to axially displace clevis 322 in a proximal direction. As clevis 322 is axially displaced, in a proximal direction, clevis 322 pulls on pinion gear 276 of articulation assembly 270. As pinion gear 276 is axially displaced, in a proximal direction, pinion gear 276 acts on racks 272, 274 to draw racks 272, 274 in a proximal direction. As racks 272, 274 are drawn in a proximal direction, with articulation cables 262, 264 respectively connected thereto, and with distal ends of articulation cables 262, 264 fixed or anchored in place, articulation cables 262, 264 are caused to be tensioned. It is contemplated that a set screw 328, clip or other device, (see FIG. 12) is be provided to fix the position of adjustment screw 324 and help to maintain articulation cables 262, 264 tensioned.

It is contemplated that over time and/or following a predetermined number of uses, that an end user of shaft assembly 200 may be able to access adjustment screw 324 and retension articulation cables 262, 264 as needed or necessary.

Turning now to FIGS. 26-49, end effector 400 is shown and described. End effector 400 is configured and adapted to apply a plurality of linear rows of fasteners 433. In certain embodiments, the fasteners are of various sizes, and, in certain embodiments, the fasteners have various lengths or rows, e.g., about 30, 45 and 60 mm in length.

Figure 27:
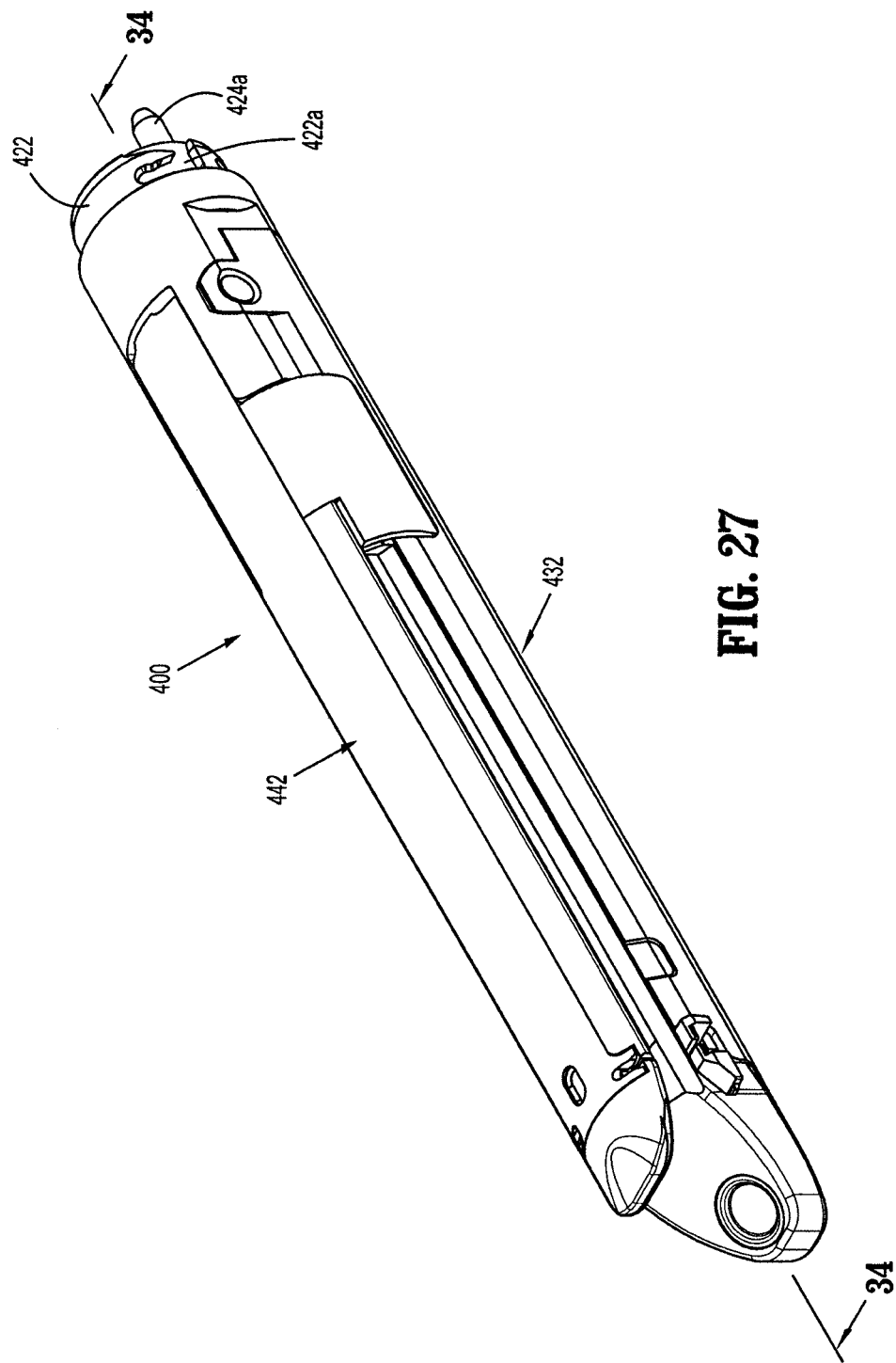
FIG. 27 is a perspective view of the end effector, shown in a closed condition.
Figure 28:
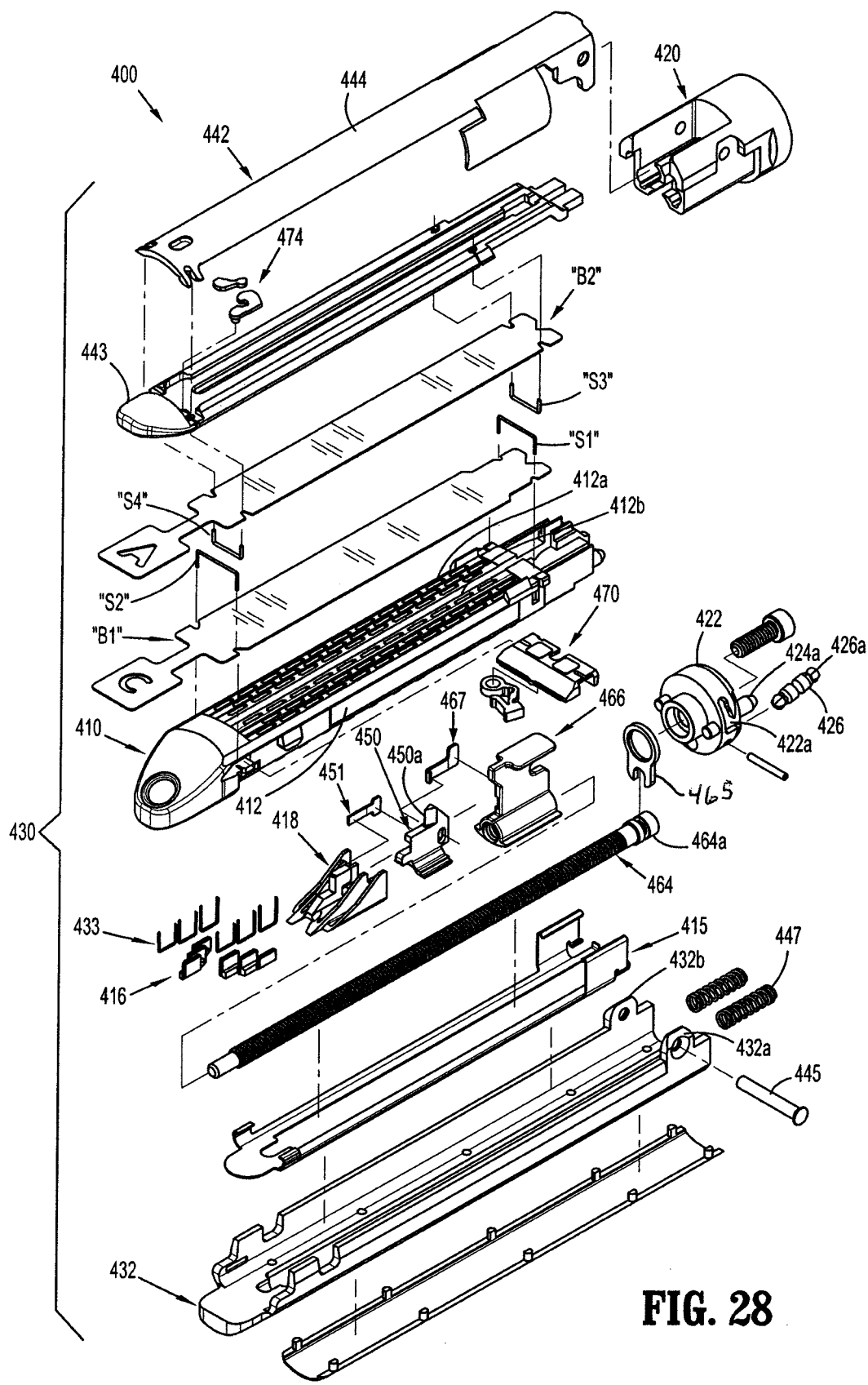
FIG. 28 is a perspective view, with parts separated, of the end effector of FIG. 27.
Figure 29:
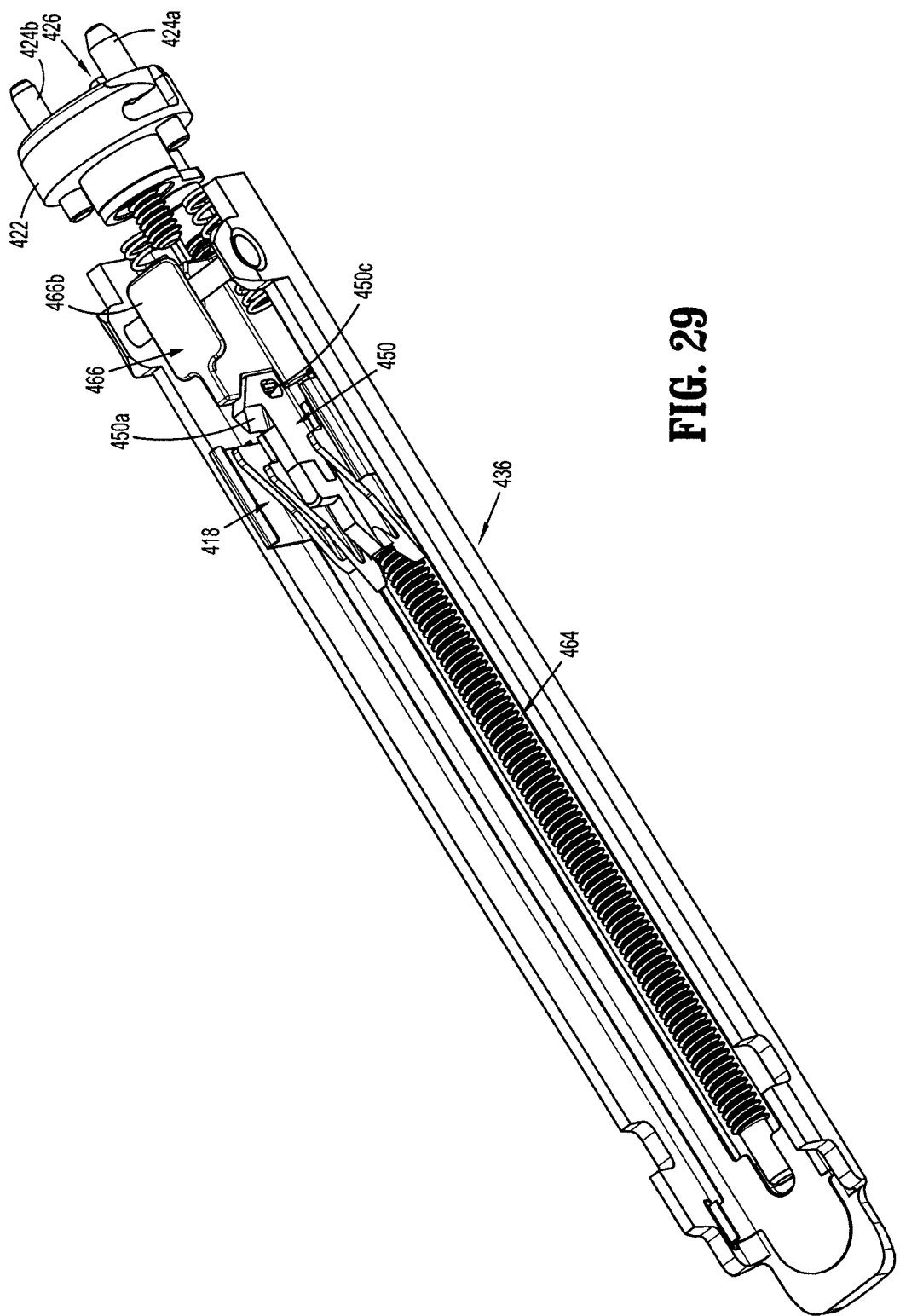
FIG. 29 is a perspective view of a lower jaw of the end effector of FIGS. 27 and 28.
Figure 30:
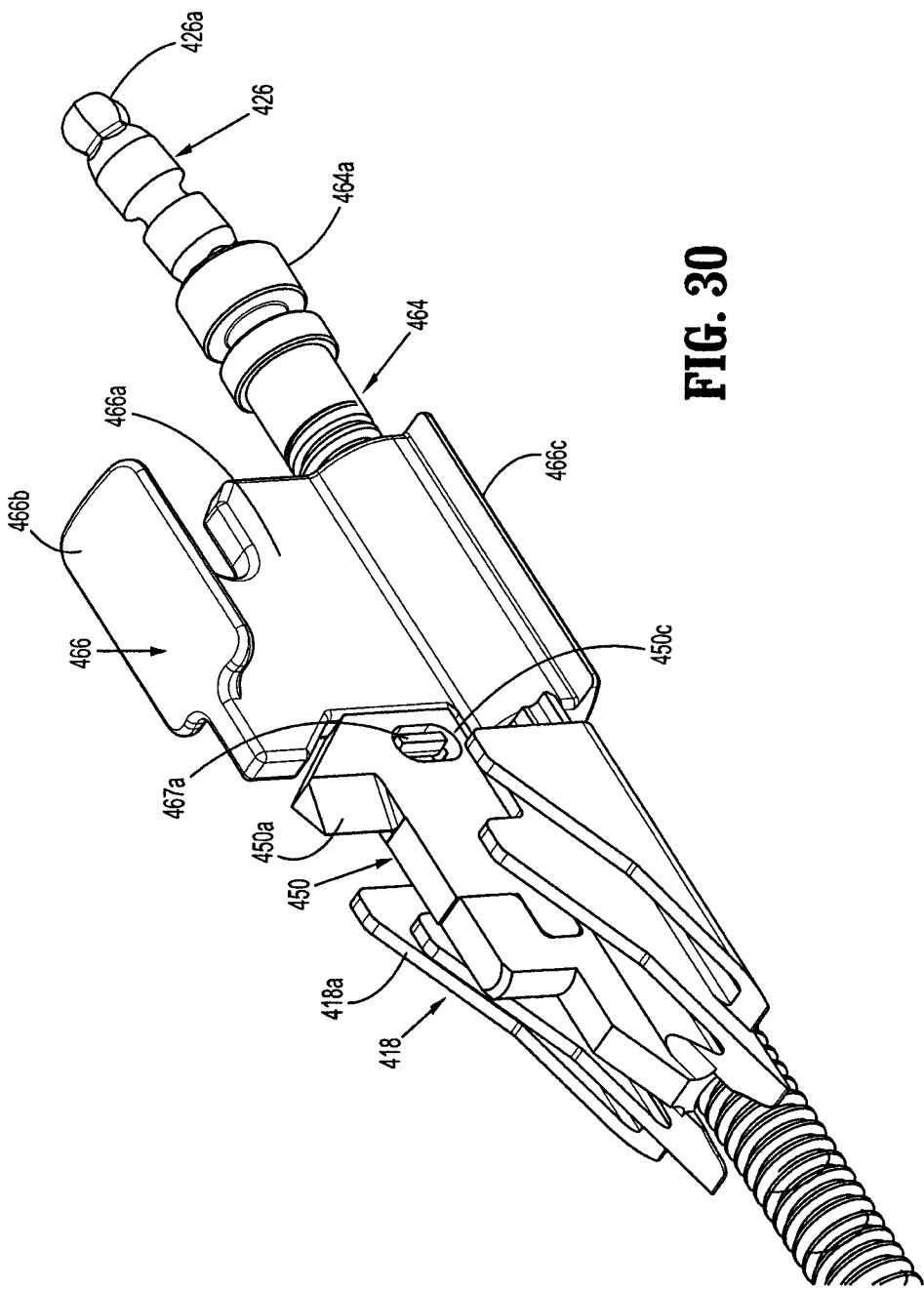
FIG. 30 is a perspective view of a drive beam, a knife sled and an actuation sled of the end effector of FIGS. 27-29.

As seen in FIGS. 26-28, end effector 400 includes a mounting portion 420 (FIG. 28) configured for selective connection to end effector coupling assembly 310 of shaft assembly 200. End effector 400 further includes a jaw assembly 430 connected to and extending distally from mounting portion 420. Jaw assembly 430, as will be discussed in greater detail below, includes a lower jaw 432 pivotally connected to mounting portion 420 and being configured to selectively support a cartridge assembly 410 therein, and an upper jaw 442 secured to mounting portion 420 and being movable, relative to lower jaw 432, between approximated and spaced apart positions.

As seen in FIGS. 26-28, mounting portion 420 includes a coupling member 422 secured to a proximal end thereof. Coupling member 422 defines a substantially J-shaped channel 422a (see FIGS. 26-28) formed in a radial outer surface thereof that is configured and dimensioned for selective connection with complementary structure formed on or extending radially inward from collar 312 of end effector coupling assembly 310, as described above. Coupling member 422 further includes a pair of spaced apart alignment stems 424a, 424b projecting proximally therefrom, for receipt in respective alignment bores 310a, 310b formed in a distal surface of end effector coupling assembly 310.

The alignment stems 424a, 424b along with the alignment bores 310a, 310b are used to align and couple end effector 400 to end effector coupling assembly 310 of shaft assembly 200. The nub 312a of collar 312 and the J-shaped channel 422a of coupling member 422 may define a conventional bayonet-type coupling which facilitates quick and easy engagement and removal of end effector 400 from shaft assembly 200 before, during or after a surgical procedure.

Mounting portion 420 further includes, as seen in FIGS. 26, 28-31, 34 and 35 a drive axle 426 rotatably supported therein. Drive axle 426 includes a multi-faceted, proximal head 426a projecting proximally from coupling member 422 and being configured for mating engagement with third spur gear 282c of first gear train 280 of distal neck housing 236 and first gear train system 240 of shaft assembly 200, when end effector 400 is coupled to shaft assembly 200. Drive axle 426 further includes multi-faceted, a distal head 426b projecting distally from coupling member 422 and being configured for mating engagement with a threaded drive shaft 464 supported in lower jaw 432 of jaw assembly 430. Drive axle 426 functions to transmit rotational drive forces from third spur gear 282c of first gear train 280 of distal neck housing 236 and of first gear train system 240 of shaft assembly 200, which defines an axis of rotation, to drive screw 464 of lower jaw 432 of jaw assembly 430, which defines an axis of rotation that is different than the axis of rotation of third spur gear 282c.

As seen in FIGS. 28-31, 34-36 and 39-43, lower jaw 432 of jaw assembly 430 includes a drive screw 464 rotatably supported therein and extending substantially an entire length thereof. Drive screw 464 includes a female coupling member 464a supported on a proximal end thereof and being configured for receipt of multi-faceted, distal head 426b of drive axle 426. Drive screw 464 is axially and laterally fixed within lower jaw 432 of jaw assembly 430 by a thrust plate 465, or the like, which is secured to jaw assembly 430 and at least partially extends into an annular channel 464a formed in drive screw 464. In operation, rotation of drive axle 426 results in concomitant rotation of drive screw 464.

Figure 33:
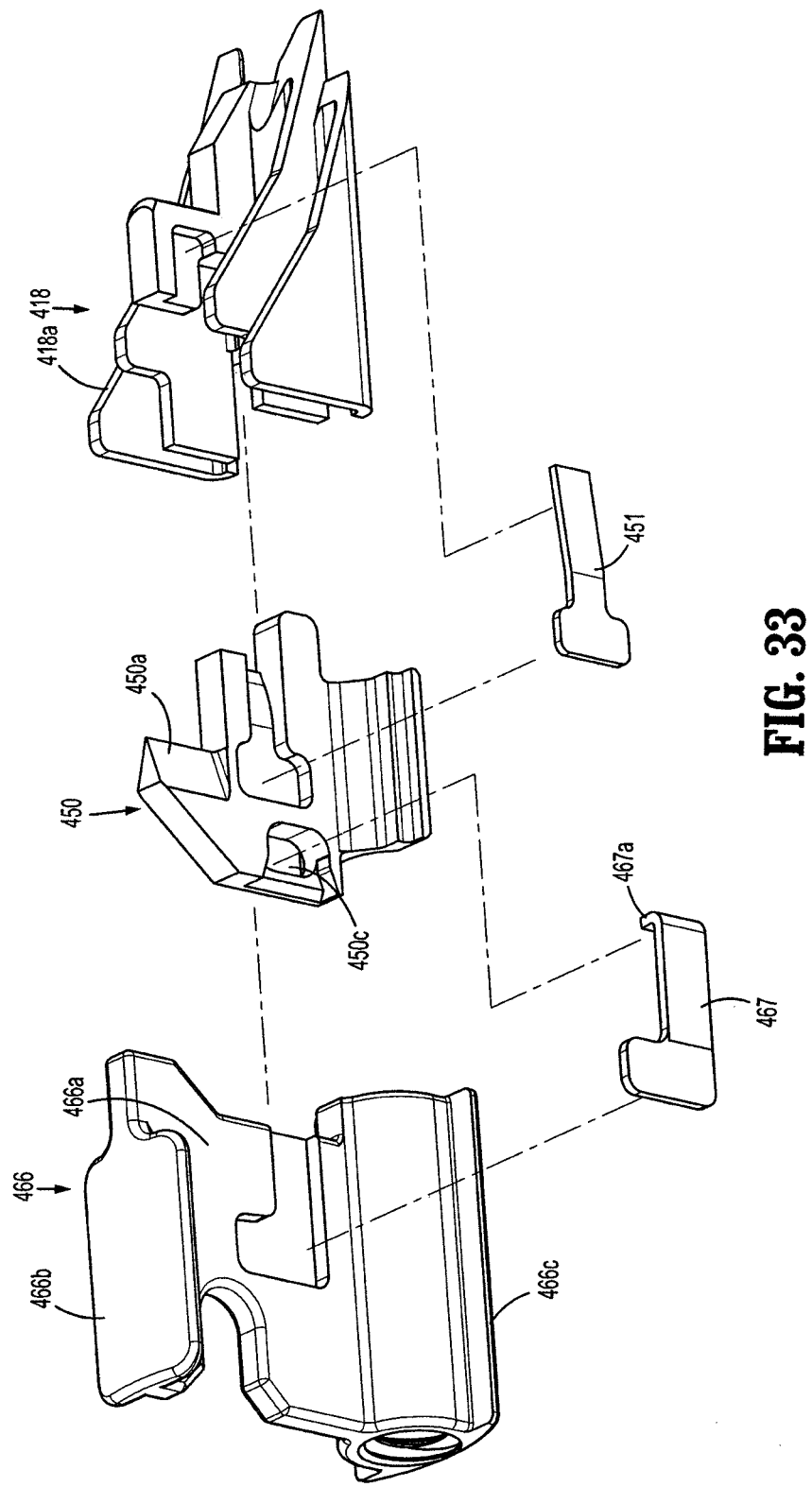
FIG. 33 is a perspective view, with parts separated, of the drive beam, the knife sled and the actuation sled of the end effector of FIGS. 27-29.

As seen in FIGS. 28-43, end effector 400 includes a drive beam 466 slidably supported in lower jaw 432 of jaw assembly 430. Drive beam 466 includes a substantially I-shaped cross-sectional profile and is configured to approximate lower jaw 432 and upper jaw 442, and to axially displace an actuation sled 418 through lower jaw 432. As seen in FIG. 33, drive beam 466 includes a vertically oriented support strut 466a; a lateral projecting member 466b formed atop support strut 466a and being configured to engage and translate with respect to an exterior camming surface of upper jaw 442 to progressively close jaw assembly 430; and a retention foot 466c having an internally threaded bore for threadable connection to threaded drive shaft 464. Since drive beam 466 is prevented from rotation by the engagement of strut 466a and/or cam member 466b with upper jaw 442, as drive screw 464 is rotated, retention foot 466c, and in turn, drive beam 466 is axially translated relative to lower jaw 432.

Drive beam 466 includes a lock clip 467 extending distally from strut 466a. Lock clip 467 defines a hook 467a configured to engage a window 450c formed in a knife sled 450, as will be discussed in greater detail below. Hook 467a of lock clip 467 is biased to extend away from knife sled 450. Prior to firing the cartridge assembly 410, the drive beam 466 is at a proximal-most position in lower jaw 432 and actuation sled 418 and knife sled 450 are at a proximal-most position in cartridge body 412, as seen in FIGS. 36 and 37. Lock clip 467, prior to firing, is disengaged from window 450c of knife sled 450 and extends into a relief 412e defined in a wall of knife slot 412b.

Lower jaw 432 is in the form of a channel and is configured and adapted to selectively receive a disposable staple cartridge assembly 410 therein. Staple cartridge assembly 410 includes a cartridge body 412 defining a plurality of rows of staple retaining slots 412a and a longitudinally extending knife slot 412b disposed between pairs of rows of staple retaining slots 412a. Staple cartridge assembly 410 also includes a plurality of staples 433 disposed, one each, in the plurality of retaining slots 412a. Staple cartridge assembly 410 further includes a plurality of staple pushers 416 supported therein, wherein the staple pushers 416 are aligned one each within retaining slots 412a such that a single staple pusher 416 is positioned under a respective staple 433 which is retained within slot 412a. Staple pushers 416 may be formed such that they are attached to each other in a pusher member having groups of two or three or four pushers, wherein the pusher member may have offset oriented pushers. One or more actuating surfaces is provided on a lower surface of the pusher member (not shown).

Staple cartridge assembly 410 includes an actuation sled 418 slidably supported against a lower surface of cartridge body 412 and being engageable by drive beam 466. Actuation sled 418 includes upstanding cam wedges 418a configured to exert a driving force on staple pushers 416, by contacting the actuating surfaces, which drives staples 414 from staple cartridge assembly 410, as described in greater detail below.

Cartridge body 412 defines a plurality of spaced apart longitudinal channels 412c (see FIG. 36) extending therethrough to accommodate the upstanding cam wedges 418a of actuation sled 418. Channels 412c communicate with the plurality of retaining slots 412a within which the plurality of staples 433 and pushers 416 are respectively supported.

As seen in FIGS. 28-43, staple cartridge assembly 410 further includes a knife sled 450 slidably supported within knife slot 412b of cartridge body 412 and being interposed between drive beam 466 and actuation sled 468. As seen in FIG. 33, knife sled 450 defines a knife blade 450a extending from an upper surface thereof and oriented distally, wherein knife blade 450a extends through knife slot 412b of cartridge body 412. Knife sled 450 includes a lock-out spring 451 extending distally therefrom for engaging a lock-out notch 412d formed in a surface of cartridge body 412 (see FIG. 37), as will be discussed in greater detail below. Lock-out spring 451 is biased toward lock-out notch 412d. Prior to firing of cartridge assembly 410, with actuation sled 418 and knife sled 450 at a proximal-most position in cartridge body 412, as seen in FIG. 34-37, lock-out spring 451 is blocked by actuation sled 418 from entering lock-out notch 412d of cartridge body 412.

Staple cartridge assembly 410 includes a bottom cover or retainer 415 configured to maintain the plurality of staple pushers 416, actuation sled 418 and knife sled 450 within cartridge body 412. Retainer 415 supports and aligns the plurality of pushers 416 prior to engagement thereof by the actuation sled 418. During operation, as actuation sled 418 translates through staple cartridge assembly 410, the angled leading edges of cam wedges 418a of actuation sled 418 sequentially contact pushers 416, causing the pushers 416 to translate vertically within retaining slots 412a, urging the staples 433 therefrom. Also, as knife sled 450 translates through knife slot 412b of cartridge body 412, knife blade 450a severs tissue and retaining sutures that extend across knife slot 412b of cartridge body 412.

In operation, as drive screw 464 is rotated, in a first direction, to advance drive beam 466, as described above, drive beam 466 is advanced into contact with knife sled 450 and actuation sled 418 to distally advance or push knife sled 450 and actuation sled 418 through cartridge body 412 and lower jaw 432. As drive beam 466 is continually driven in the distal direction, drive beam 466 maintains contact with knife sled 450 and actuation sled 418, thereby pushing knife sled 450 and actuation sled 418 in the distal direction and to approximate lower jaw 430 and upper jaw 440, as laterally projecting member 466b of drive beam 466 pushes down on the exterior camming surface of upper jaw 440, to eject the staples 414 and fasten tissue, and to simultaneously dissect tissue with knife blade 450a. Knife sled 450, actuation sled 418 and drive beam 466 travel through cartridge body 412 thereby fastening and severing tissue.

Figure 38:
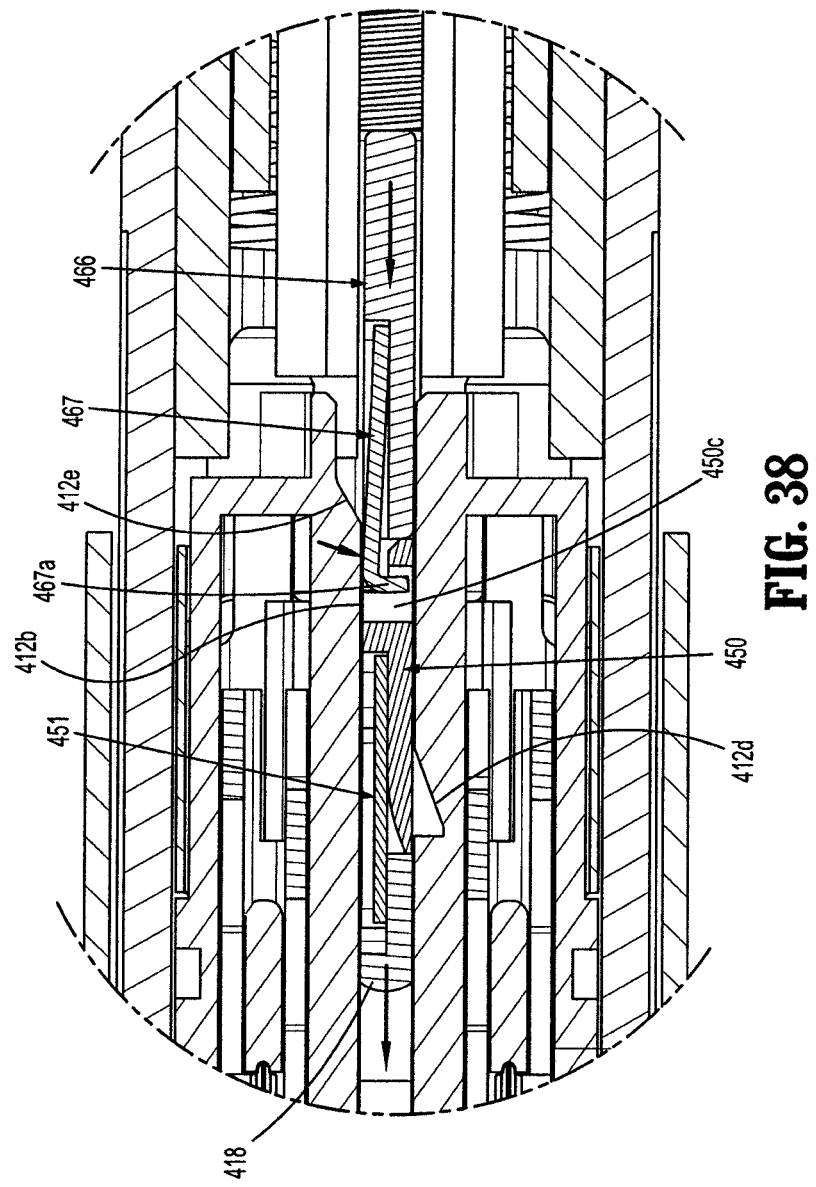
FIG. 38 is a further enlarged view illustrating the drive beam, the knife sled and the actuation sled in a distally advanced position.
Figure 39:
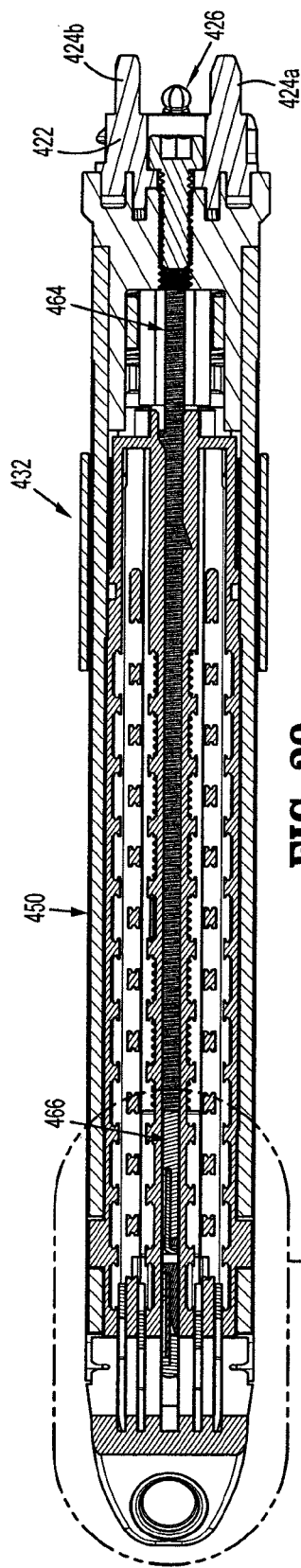
FIG. 39 is a cross-sectional view of the end effector of FIG. 27, as taken through 34-34 of FIG. 27, illustrating the drive beam, the knife sled and the actuation sled in a distal-most position.
Figure 40:
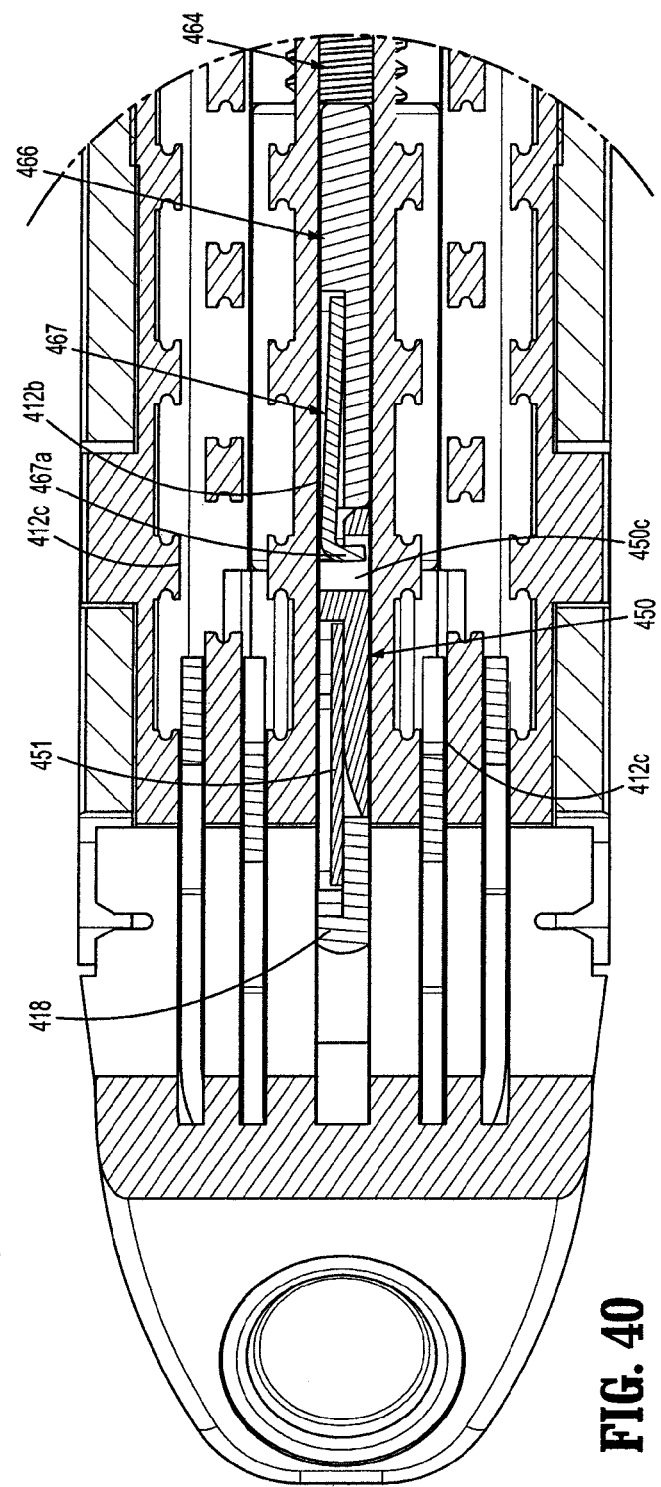
FIG. 40 is an enlarged view of the indicated area of detail of FIG. 39.

As seen in FIGS. 37 and 38, as drive beam 466 is advanced distally, hook 467a of lock clip 467 exits relief 412e and is cammed into window 450c of knife sled 450 as hook 467a enters knife slot 412b of cartridge body 412. Drive screw 464 is rotated until actuation sled 418, knife sled 450 and drive beam 466 reach a distal-most end of cartridge body 412 and/or lower jaw 432, for a complete firing.

Following a complete or partial firing, drive screw 464 is rotated in an opposite direction to retract drive beam 466. Since the knife sled 450 is connected to drive beam 466 by lock clip 467, as described above, as drive beam 466 is retracted, knife sled 450 is also retracted. Actuation sled 418 will tend to remain at a distal or distal-most position due to its frictional engagement in channels 412c of cartridge body 412 (see FIG. 40). Drive screw 464 is rotated until drive beam 466 and knife sled 450 are returned to the proximal-most position. Once drive beam 466 and knife sled 450 are returned to the proximal-most position, hook 467a of lock clip 467 is permitted to re-enter relief 412e, due to its own resiliency, and disengage from window 450c of knife sled 450. As such, drive beam 466 is disengaged from knife sled 450, and staple cartridge assembly 410 is free to be removed from lower jaw 432. With the knife sled in its proximal most position, the knife edge is sheltered between the two protrusions on the cartridge (visible in FIG. 28). This prevents injury when replacing the cartridge. This also protects the knife edge prior to use.

Figure 43:
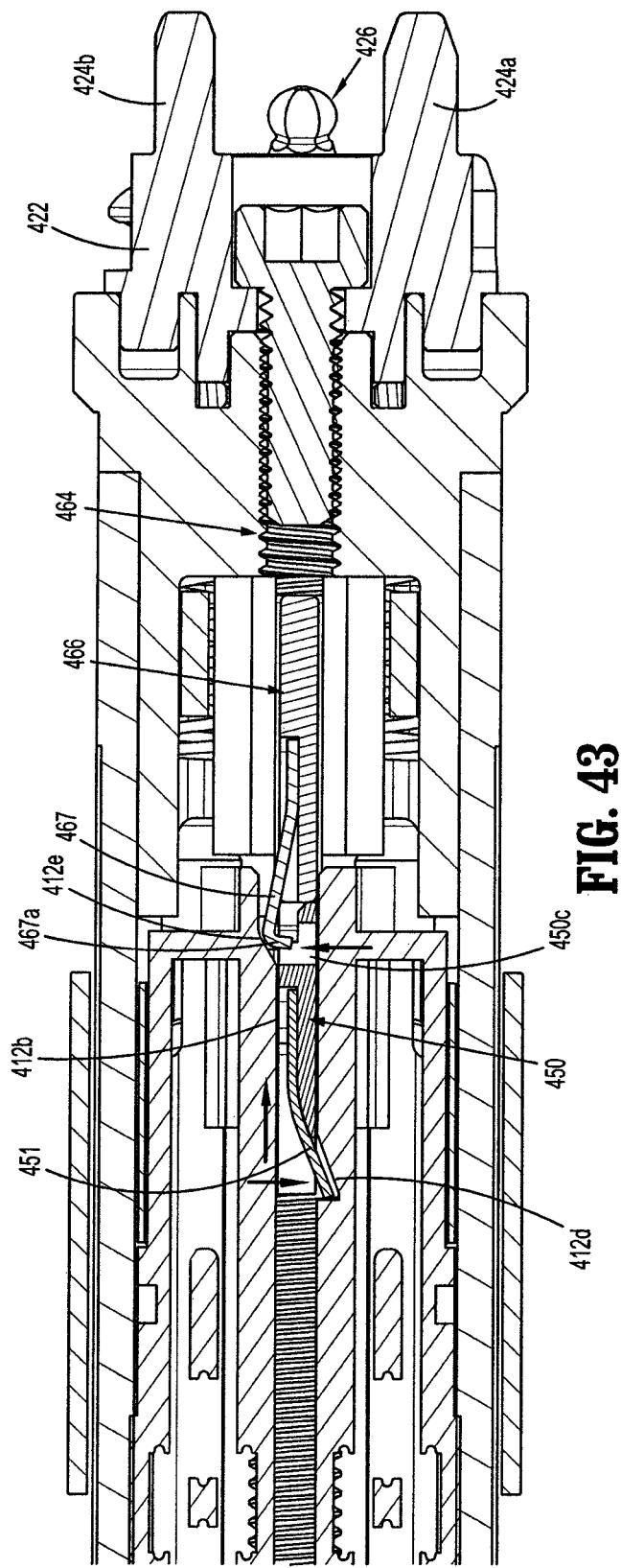
FIG. 43 is a cross-sectional view of a proximal end of the end effector of FIG. 27, as taken through 34-34 of FIG. 27, illustrating the drive beam and the knife sled in a proximal-most position.
Figures 44, 45:
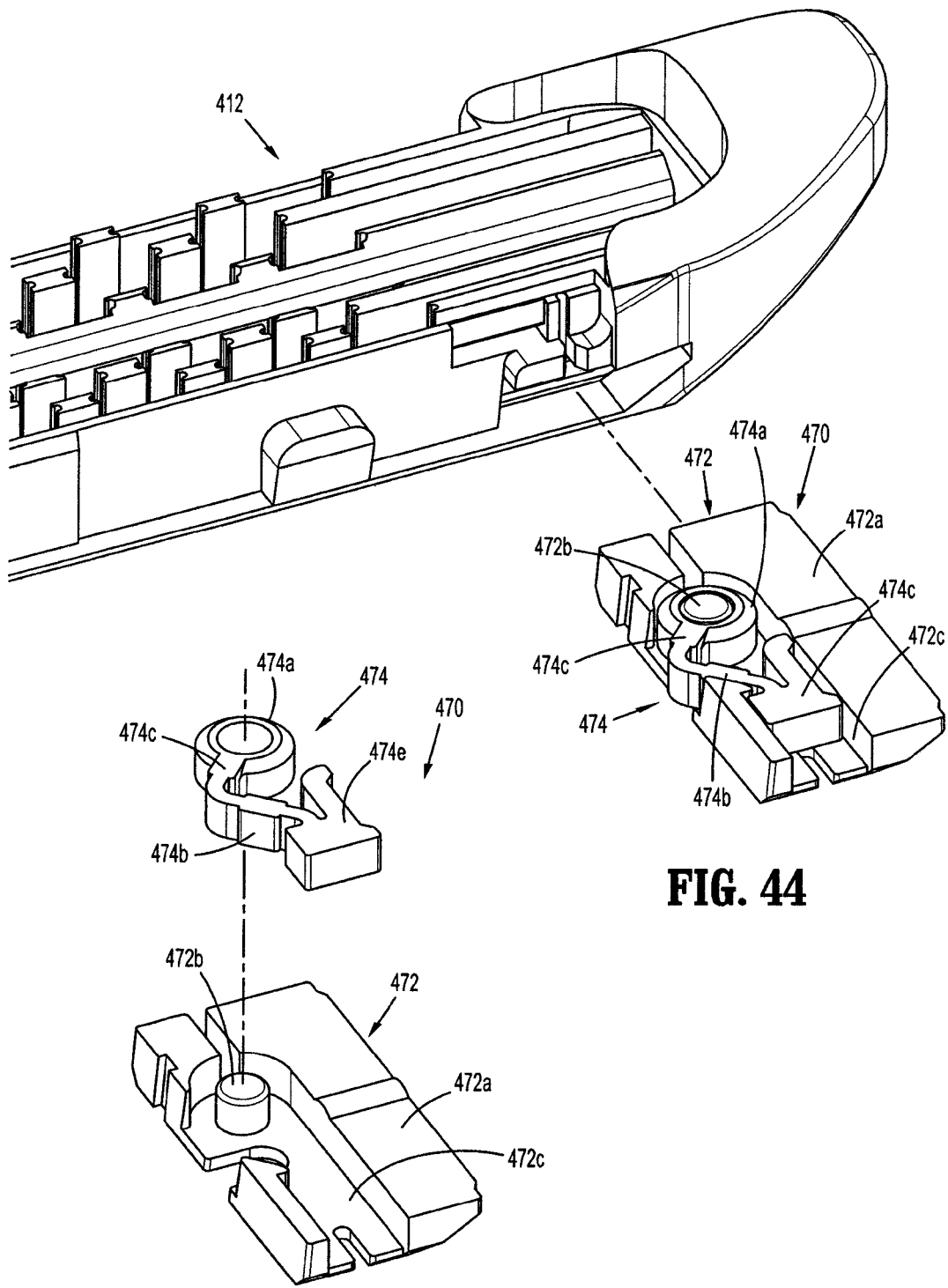
FIG. 44 is a perspective view, with parts partially separated, of a release assembly supported in a distal end of a cartridge assembly of the end effector.
FIG. 45 is a perspective view, with parts separated, of the release assembly of FIG. 44.

Also, when drive beam 466 and knife sled 450 are returned to the proximal-most position, with actuation sled 418 now separated from knife sled 450, since lock-out spring 451 is biased toward lock-out notch 412d, as seen in FIG. 43, lock-out spring 451, which is attached to knife sled 450, is now free to enter lock-out notch 412d and prevent knife sled 450 and/or drive beam 466 being re-advanced, thereby locking-out staple cartridge assembly 410.

In order for drive beam 466 to be re-advanced, a new, un-fired staple cartridge assembly 410 needs to be loaded into lower jaw 432.

Upper jaw 442 of jaw assembly 430 functions as an anvil against which the staples 433 form when actuation sled 418 is advanced during a firing of surgical instrument 100. In particular, upper jaw 442 includes an anvil plate 443, secured to a cover housing 444, in juxtaposed relation to staple cartridge assembly 410. Anvil plate 443 defines a plurality of staple forming pockets (not shown), arranged in longitudinally extending rows that cooperate with the rows of staple retaining slots 412a of staple cartridge assembly 410, when staple cartridge assembly 410 is disposed in lower jaw 432.

Lower jaw 432 is pivotably connected to mounting portion 420 by way of appropriate pivot pins 445 or the like extending through a pair of spaced apart shoulders 432a, 432b disposed near a proximal end thereof. Shoulders 432a, 432b of lower jaw 432 extend into reliefs or the like formed in mounting portion 420.

As seen in FIG. 28, jaw assembly 430 includes at least one biasing member 447, in the form of a compression spring or the like, disposed between each shoulder 432a, 432b of lover jaw 432 and a bearing surface of mounting portion 420 such that lower jaw 432 is spaced from upper jaw 442, until closed, to maintain jaw assembly 430 in an open position. In use, as jaw assembly 430 is closed, by approximating upper jaw 442 and lower jaw 432, biasing members 447 are biased (i.e., compressed) between shoulders 432a, 432b of lower jaw 432 and the bearing surface of mounting portion 420.

Following firing of staple cartridge assembly 410, drive screw 464 is rotated, in a second direction that is opposite the first direction, to withdraw drive beam 466 and knife sled 450, as described above. As drive beam 466 is withdrawn in a proximal direction, biasing members 447 begin to expand to press apart shoulders 432a, 432b of lower jaw 432 from the bearing surface of mounting portion 420 to separate the upper jaw 442 from the lower jaw 432 to open jaw assembly 430.

In accordance with the present disclosure, cartridge body 412 of staple cartridge assembly 410 may be configured and adapted to selectively support a surgical buttress on a tissue contact surface thereof. With reference to FIG. 28, cartridge body 412 of staple cartridge assembly 410 defines a proximal pair of recesses formed near a proximal end thereof and disposed, one each, on opposed sides of longitudinally extending knife slot 412b. Cartridge body 412 further defines a distal pair of recesses 412e formed near a distal end thereof and disposed, one each, on opposed sides of longitudinally extending knife slot 412b. In one embodiment, the distal pair of recesses 412e is preferably non-circular and constricting or otherwise arranged so as to frictionally engage and/or pinch an anchor "S".

As seen in FIG. 28, cartridge body 412 further includes a surgical cartridge buttress "B1", pledget or the like operatively secured to an upper surface or tissue contacting surface thereof, by suture anchors "S1" and "S2", to overlie at least some of the plurality of staple retaining slots 412a and/or at least a portion of a length of longitudinally extending knife slot 412b. In particular, an anchor "S1" is cinched around a proximal portion of surgical cartridge buttress "B1" and each of the proximal pair of recesses and an anchor "S2" is cinched around a distal portion of the surgical cartridge buttress "B1" and each of the distal pair of recesses 412e. The anchors may comprise a surgical suture.

In one particular embodiment, a first end of suture anchor "S1" includes a knot, stop or the like (not shown) sized so as to not pass through one recess of the proximal pair of recesses and a second end of suture anchor "S1" passes over, and transversely across, surgical cartridge buttress "B1", at least once, and back through the other recess of the proximal pair of recesses. For example, the second end of suture anchor "S1" may be pinched or cinched in the other recess of the proximal pair of recesses so as to anchor the second end of the suture anchor "S1" and secure the surgical cartridge buttress "B1" against the tissue contacting surface of cartridge body 412. Similarly, a suture anchor "S2" is used to extend transversely across surgical cartridge buttress "B1" and into engagement with the distal pair of recesses 412e.

Surgical cartridge buttress "B1" includes a proximal pair of notches formed in side edges aligned with the proximal pair of recesses of cartridge body 412, a distal pair of notches formed in side edges thereof aligned with the distal pair of recesses 412e of cartridge body 412, and a proximal notch formed in a proximal edge thereof aligned with longitudinally extending knife slot 412b when cartridge buttress "B1" is secured to cartridge body 412. Cartridge buttress "B1" further includes a tongue or tab extending from a distal edge thereof to facilitate with the attachment of cartridge buttress "B1" to cartridge body 412 during the assembly process. It is contemplated that a width of cartridge buttress "B1" may be reduced in a proximal portion thereof. It is further contemplated that the tongue is removed from cartridge buttress "B1" following securement of cartridge buttress "B1" to cartridge body 412 and prior to packaging or shipment.

As seen in FIGS. 28 and 44-47, cartridge body 412 of staple cartridge assembly 410 includes a cartridge buttress release assembly 470 supported in and near a distal end of cartridge body 412. Release assembly 470 includes a retainer 472 supported in a distal end of cartridge body 412 at a location near a distal end of longitudinally extending knife slot 412b and at least partially extending thereacross. Retainer 472 includes a body portion 472a, a boss 472b extending from a surface thereof, and defines a channel or recess 427c formed in a surface thereof and extending through a side thereof. When supported in cartridge body 412, recess 472c of retainer 472 is in registration with one of the pair of distal recesses 412e of cartridge body 412.

Release assembly 470 further includes a pusher member 474 having a head portion 474a pivotally connected to boss 472b of retainer 472. Pusher member 474 further includes a first leg member 474b extending from head portion 474a and a second leg member 474c connected to a free end of first leg member 474b via a living hinge connection. Pusher member 474 further includes piston 474e connected to a free end of second leg member 474c via a living hinge connection. Piston 474e is slidably disposed and translatable within recess 472c of retainer 472. In certain other embodiments, the pusher is a linkage assembly having a first link pivotally connected to the cartridge body at one end. The other end of the first link is pivotally connected to a first end of a second link. The opposite, second, end of the second link is confined in the recess of the retainer.

Figure 46:
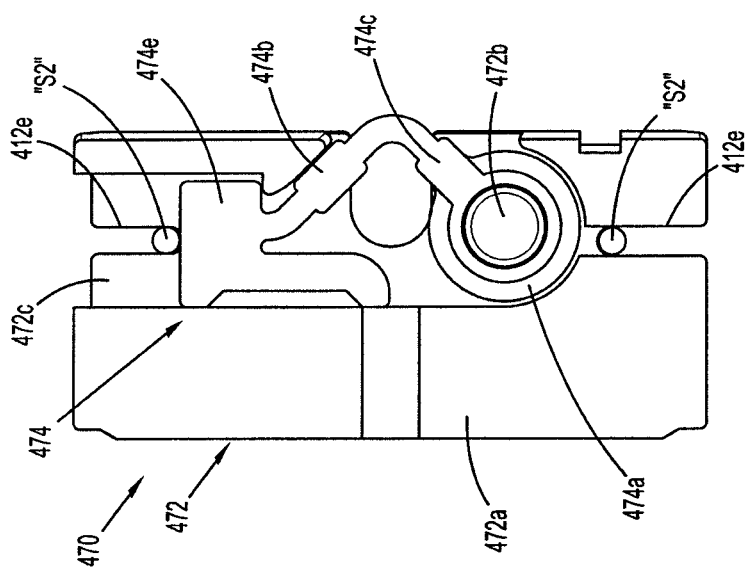
FIG. 46 is a plan view of the release assembly of FIGS. 44 and 45, shown in an unactuated condition.

As seen in FIG. 46, release assembly 470 includes an unactuated configuration wherein piston 474e does not extend into or overlie the respective one of the pair of distal recesses 412e of cartridge body 412, and first leg member 474b and second leg member 474c are angled with respect to one another and project proximally along longitudinally extending knife slot 412b of cartridge body 412. It is contemplated that release assembly 470 may include a friction fit or snap fit feature for maintaining and/or retaining release assembly 470 in the locking or anchoring configuration at all times following the manufacturing/assembly process and prior to a complete firing of surgical instrument 100.

Figure 47:
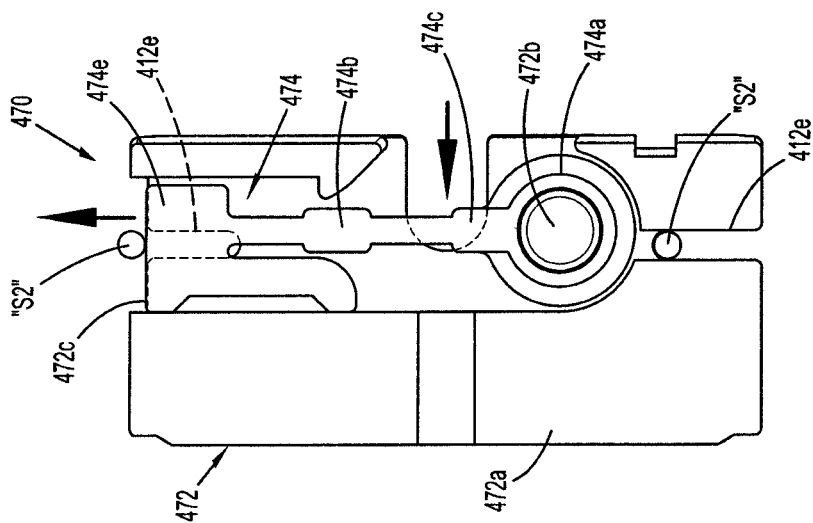
FIG. 47 is a plan view of the release assembly of FIGS. 44 and 45, shown in an actuated condition.

As seen in FIG. 47, release assembly 470 includes an actuated configuration wherein piston 474e extends into or overlies the respective one of the pair of distal recesses 412d of cartridge body 412 in operative registration therewith, and first leg member 474b and second leg member 474c are extended substantially along a common axis.

In operation, with surgical cartridge buttress "B1" secured against the tissue contacting surface of cartridge body 412, during firing of surgical instrument 100, as drive beam 466 is advanced (i.e., moved from a proximal-most position to a distal-most position), knife blade 450a of knife sled 450 slices through a central section of proximal suture anchor "S1", thereby freeing the proximal end of the surgical cartridge buttress "B1" from cartridge body 412. During use, as the firing stroke of surgical instrument 100 is nearing completion and as actuation sled 418 approaches a distal end of longitudinally extending knife slot 412bc of cartridge body 412, actuation sled 418 contacts the living hinge connection between first leg member 474b and second leg member 474c. As actuation sled 418 is further advanced distally, actuation sled 418 presses against the living hinge connection, causing first leg member 474b and second leg member 474c to extend. As first leg member 474b and second leg member 474c extend, piston 474e is translated through recess 472c of retainer 472. As piston 474e is translated through recess 472c of retainer 472, piston 474e engages the second end of suture anchor "S2" and urges the second end of suture anchor "S2" out of the distal recess 412d of cartridge body 412 that is in registration therewith to release the second end of suture anchor "S2" therefrom. With the second end of suture anchor "S2" released or free from distal recess 412d of cartridge body 412, the distal end of the surgical cartridge buttress "B1" is free to separate from the tissue contacting surface of cartridge body 412.

As seen in FIG. 28, upper jaw 442 further includes a surgical anvil buttress "B2", pledget or the like operatively secured to an upper surface or tissue contacting surface thereof, by anchors "S3" and "S4", to overlie at least some of the plurality of staple forming pockets and/or at least a portion of a length of a longitudinally extending knife slot of anvil plate 443. The anchors may comprise surgical sutures. In particular, a suture anchor "S3" is cinched around a proximal portion of surgical anvil buttress "B2" and each of the proximal pair of recesses and a suture anchor "S4" is cinched around a distal portion of the surgical anvil buttress "B2" and each of a distal pair of recesses 443a formed in opposed side edges of anvil plate 443.

In one particular embodiment, a first end of suture anchor "S3" includes a knot, stop or the like (not shown) sized so as to not pass through one recess of the proximal pair of recesses and a second end of suture anchor "S3" passes over, and transversely across, surgical anvil buttress "B2", at least once, and back through the other recess of the proximal pair of recesses. For example, the second end of suture anchor "S3" may be pinched or cinched in the other recess of the proximal pair of recesses so as to anchor the second end of the suture anchor "S3" and secure the surgical anvil buttress "B2" against the tissue contacting surface of anvil plate 443. Similarly, a suture anchor "S4" is used to extend transversely across surgical anvil buttress "B2" and into engagement with the distal pair of recesses 443a.

Surgical anvil buttress "B2" includes a proximal pair of notches formed in side edges aligned with the proximal pair of recesses of anvil plate 443, a distal pair of notches formed in side edges thereof aligned with the distal pair of recesses 443a of anvil plate 443, and a proximal notch formed in a proximal edge thereof aligned with longitudinally extending knife slot when anvil buttress "B2" is secured to anvil plate 443. Anvil buttress "B2" further includes a tongue or tab extending from a distal edge thereof to facilitate with the attachment of anvil buttress "B2" to anvil plate 443 during the assembly process. It is contemplated that the tongue is removed from anvil buttress "B2" following securement of anvil buttress "B2" to anvil plate 443 and prior to packaging or shipment.

Figure 48:
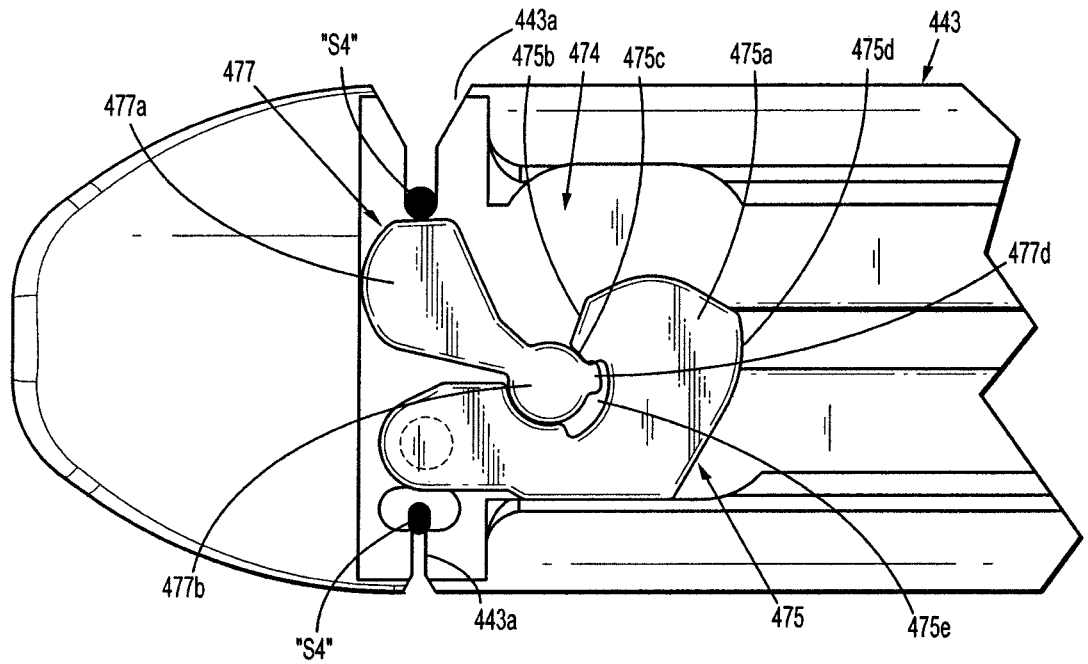
FIG. 48 is a plan view of a release assembly supported in a distal end of an upper jaw of the end effector, illustrated in an unactuated condition.
Figure 49:
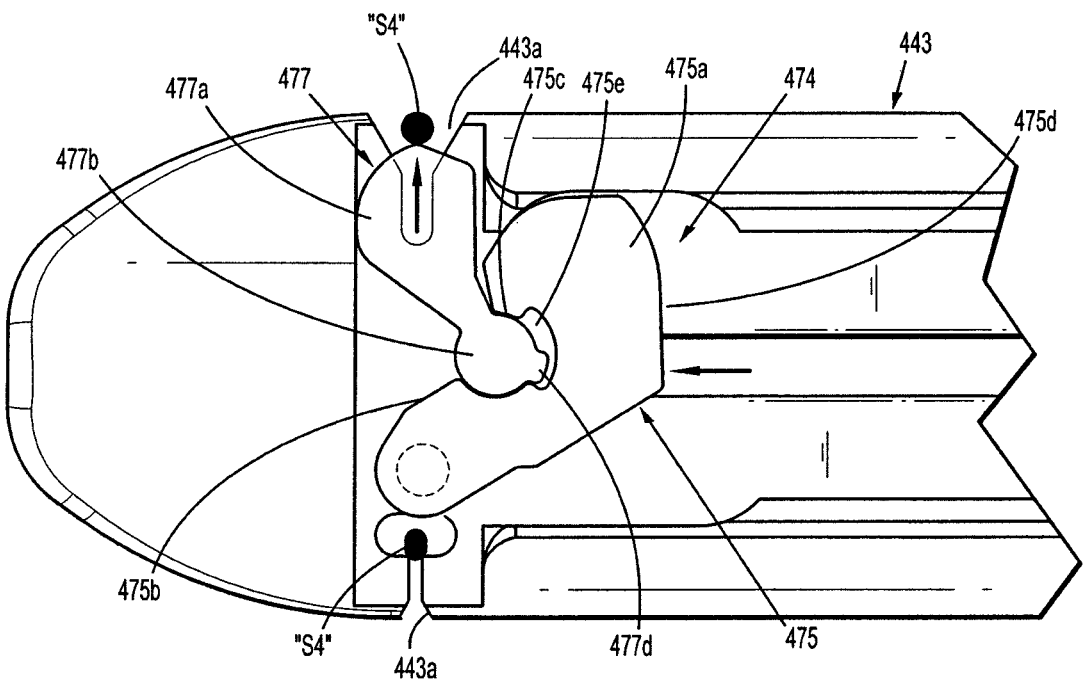
FIG. 49 is a plan view of the release assembly of FIG. 48, illustrated in an actuated condition.

As seen in FIGS. 28 and 48-49, upper jaw 442 of jaw assembly 430 includes a suture release assembly 474 disposed between anvil plate 443 and cover housing 444 at a location in operative registration with a distal pair of side recesses 443a. Suture release assembly 474 includes a link arm 475 pivotally connected to anvil plate 443 and/or optionally cover housing 444. Link arm 475 includes a body portion 475a defining a pocket or recess 475c formed in a first side edge 475b thereof and a camming surface 475d defined substantially along an adjacent side or proximal edge thereof. Pocket 475c has a substantially arcuate, circular or rounded profile and defines an arcuate relief 475e in a side wall thereof. Link arm 475 includes a pivot pin extending from body portion 475a for pivotally connecting link arm 475 to upper jaw 442.

Release assembly 474 further includes a pusher bar 477 pivotally connected to link arm 475 and slidably disposed between anvil plate 443 and cover housing 444. Pusher bar 477 includes a body portion 477a having a substantially rectangular configuration and a head 477b, extending from a corner of body portion 477a, and having a substantially circular or rounded configuration. Head 477b of pusher bar 477 is configured and dimensioned for pivotable and/or rotatable connection in pocket 475c of link arm 475. Head 477b of pusher bar 477 includes a stop member 477d projecting from a side edge thereof and into arcuate relief 475e of pocket 475c of link arm 475. A relative distance of rotation of pusher bar 477 relative to link arm 475 is determined by a relative length of arcuate relief 475e and a relative width of stop member 477d.

As seen in FIG. 48, suture release assembly 474 includes an unactuated configuration wherein pusher bar 477 does not extend into or overlie the respective one of the pair of distal recesses 443a in operative registration therewith, and a longitudinal axis of link arm 475 is oriented substantially parallel with a longitudinal axis of upper jaw 442. It is contemplated that suture release assembly 474 may include a friction fit or snap fit feature for maintaining and/or retaining suture release assembly 474 in the locking or anchoring configuration at all times following the manufacturing/assembly process and prior to a complete firing of the surgical stapling apparatus.

As seen in FIG. 49, suture release assembly 474 includes an actuated configuration wherein pusher bar 477 extends into or overlies the respective one of the pair of distal recesses 443a in operative registration therewith, and a longitudinal axis of link arm 475 is oriented substantially transverse to the longitudinal axis of upper jaw 442.

With reference to FIGS. 28 and 34-43, in operation, with a surgical anvil buttress (not shown) secured against the lower surface of anvil plate 443, during firing of the surgical stapling apparatus, as drive beam 466 is advanced (i.e., moved from a proximal-most position to a distal-most position), knife blade 450a slices through a central section of the proximal suture (not shown), thereby freeing the proximal end of the surgical anvil buttress (not shown) from upper jaw 442. During use, as the firing stroke of the surgical instrument is nearing completion and as drive beam 466 approaches a distal-most end of the knife slot of anvil plate 443, as seen in FIG. 49, actuation sled 418 contacts camming surface 475d of link arm 475, thus urging link arm 475 to rotate or pivot around the pivot pin and, in turn, urging pusher bar 477 to translate in the direction of the slot. As pusher bar 477 is translated, pusher bar 477 comes into contact with and urges the second end of suture "S4" out of the distal recess 443a that is registration therewith to release the second end of suture "S4" therefrom. With the second end of surgical suture "S4" released or free from distal recess 443a, the distal end of the surgical anvil buttress "B2" is free to separate from the tissue contacting surface of anvil plate 443.

Exemplary surgical buttresses "B" for use with the staple cartridge assembly 410 and/or anvil plate 443 disclosed herein are shown and described in commonly assigned U.S. Pat. Nos. 5,542,594, 5,908,427, 5,964,774, 6,045,560, and 7,823,592; commonly assigned U.S. application Ser. No. 12/579,605, filed on Oct. 15, 2009 (now U.S. Patent Publication No. 20110089220); commonly assigned U.S. application Ser. No. 11/241,267, filed on Sep. 30, 2005 (now U.S. Patent Publication No. 2006/0085034); and U.S. application Ser. No. 13/097,194, filed on Apr. 29, 2011, entitled "Surgical Stapling Apparatus;" the entire contents of each of which being incorporated herein by reference.

Surgical buttresses "B" may be fabricated from a suitable biocompatible and bioabsorbable material. Surgical buttresses "B" may be fabricated from a non-absorbent material which does not retain fluid. Surgical buttresses "B" may be fabricated from "BIOSYN" made from GLYCOMER 631 (a block copolymer), a synthetic polyester composed of glycolide, dioxanone and trimethylene carbonate.

One block of the resulting copolymer contains randomly combined units derived from p-dioxanone (1,4-dioxan-2- one) and trimethylene carbonate (1,3-dioxan-2-one). The second block of the copolymer contains randomly combined units derived from glycolide and p-dioxanone. The resulting polyester is an ABA triblock terpolymer possessing about 60% glycolide, about 14% dioxanone, and about 26% trimethylene carbonate.

The surgical buttress may comprise polymers or copolymers of glycolide, lactide, poly caprolactone, trimethylene carbonate, dioxanone, caprolactone, and may be molded, extruded, etc. into a desired shape, or formed into a knitted, woven, braided, non-woven or felted material.

It will be understood that various modifications may be made to the embodiments disclosed herein. For example, surgical instrument 100 and/or cartridge assembly 410 need not apply staples but rather may apply two part fasteners as is known in the art. Further, the length of the linear row of staples or fasteners may be modified to meet the requirements of a particular surgical procedure. Thus, the length of the linear row of staples and/or fasteners within a staple cartridge assembly may be varied accordingly. Therefore, the above description should not be construed as limiting, but merely as exemplifications of preferred embodiments. Those skilled in the art will envision other modifications within the scope and spirit of the claims appended thereto.

What is claimed is:

1. An electromechanical surgical system, comprising:
 a hand-held surgical instrument including an instrument housing defining a connecting portion for selectively connecting with a shaft assembly, the surgical instrument having at least one rotatable drive member;
 an end effector configured to perform at least one function and including:
  an upper jaw,
  lower jaw;
  a drive beam translatable through at least one of the upper jaw or the lower jaw to move the lower jaw relative to the upper jaw; and
  a cartridge assembly selectively receivable in the lower jaw and including:
   a cartridge body defining a longitudinally extending knife slot;
   a plurality of staples disposed in individual staple retaining slots formed in the cartridge body, wherein the staple retaining slots are arranged in multiple longitudinally extending rows disposed on opposed lateral sides of the knife slot;
   an actuation sled slidably supported in the cartridge body and being configured to expel at least a portion of the plurality of staples from the cartridge body upon a distal movement of the actuation sled from a proximal-most position., wherein the actuation sled of the cartridge assembly remains in a distally advanced position following any retraction of the drive beam; and
   a knife sled slidably supported in the cartridge body at a location proximal of the actuation sled, wherein the knife sled includes a knife blade extending into the knife slot, wherein the drive beam engages the knife sled and the actuation sled when the cartridge assembly is disposed in the lower jaw and when the drive beam is advanced; and
 the shaft assembly being arranged for selectively interconnecting the end effector and the surgical instrument, the shaft assembly including:
  a transmission housing configured and adapted for selective connection to the connecting portion of the surgical instrument and to be in operative communication with each of the at least one rotatable drive member of the surgical instrument;
  an outer tubular body having a proximal end supported by the transmission housing and a distal end configured and adapted for operative connection with the end effector; and
  a force transmitting assembly for interconnecting a respective one of the at least one rotatable drive member of the surgical instrument and at least one rotation receiving member supported in the end effector, wherein the force transmitting assembly includes a first end that is connectable to the at least one rotatable drive member of the surgical instrument and a second end that is connectable to the at least one rotation receiving member of the end effector, wherein the force transmitting assembly transmits a rotation of the at least one rotatable drive member of the surgical instrument to the at least one rotation receiving member of the end effector.

2. The electromechanical surgical system according to claim 1, wherein the handheld surgical instrument further includes:
 at least one drive motor supported in the instrument housing and being configured to rotate the at least one rotatable drive member;
 a battery disposed within the instrument housing for powering the at least one drive motor; and
 a circuit board disposed within the instrument housing for controlling power delivered from the battery to the at least one drive motor.

3. The electromechanical surgical system according to claim 1, further comprising:
 at least one surgical buttress releasably secured to a tissue contacting surface of at least one of the upper jaw or the lower jaw.

4. The electromechanical surgical system according to claim 1, wherein the
 at least one surgical buttress is secured to the at least one of the upper jaw or the lower jaw by at least one suture, the at least one of the upper jaw or the lower jaw being configured to receive a portion of the at least one suture.

5. The electromechanical surgical system according to claim 1, wherein the knife sled of the cartridge assembly includes a lock-out spring extending therefrom, wherein the lockout spring of the knife sled engages a lock-out notch defined in the cartridge body to inhibit advancement of the knife sled.

6. The electromechanical surgical system according to claim 5, wherein, when the actuation sled and the knife sled are in a proximal-most position, the actuation sled blocks engagement of the lock-out spring of the knife sled with the lock-out notch of the cartridge body.

7. The electromechanical surgical system according to claim 6, wherein the knife sled of the cartridge assembly is retracted upon any retraction of the drive beam.

8. The electromechanical surgical system according to claim 7, wherein the drive beam includes a lock clip extending therefrom, wherein the lock clip of the drive beam engages the knife sled upon any distal advancement of the drive beam such that the knife sled retracts upon a retraction of the drive beam.

9. The electromechanical surgical system according to claim 8, wherein the at least one rotation receiving member of the end effector includes a drive screw rotatably supported in the lower jaw, wherein the drive beam is threadably supported on the drive screw, whereby rotation of the drive screw results in axial translation of the drive beam.

10. The electromechanical surgical system according to claim 1, wherein the at least one rotation receiving member of the end effector includes a drive screw rotatably supported in the lower jaw, wherein the drive beam is threadably supported on the drive screw, whereby rotation of the drive screw results in axial translation of the drive beam.

11. The electromechanical surgical system according to claim 1, wherein the at least one force transmitting assembly of the shaft assembly includes a first gear train system interconnecting the at least one rotatable drive member of the surgical instrument and the at least one rotation receiving member of the end effector, wherein the first gear train system varies at least one of:
 a rate of rotation between the at least one rotatable drive member of the surgical instrument and the at least one rotation receiving member of the end effector; or
 an axis of rotation between the at least one rotatable drive member of the surgical instrument and the at least one rotation receiving member of the end effector.

12. The electromechanical surgical system according to claim 11, wherein the shaft assembly includes an articulating neck assembly, and wherein the first gear train system is disposed proximal of the articulating neck assembly.

13. The electromechanical surgical system according to claim 12, wherein the shaft assembly includes a neck housing disposed distal of the articulating neck assembly, wherein the neck housing supports a neck first gear train of the at least one force transmitting assembly, wherein the neck first gear train interconnects an output of the first gear train system with the at least one rotation receiving member of the end effector, wherein the neck first gear train varies at least one of:
 a rate of rotation between the output of the first gear train system and the at least one rotation receiving member of the end effector; or
 an axis of rotation between the output of the first gear train system and the at least one rotation receiving member of the end effector.

14. The electromechanical surgical system according to claim 13, wherein the at least one rotation receiving member of the end effector includes a drive screw rotatably supported in the lower jaw, wherein the drive beam is threadably supported on the drive screw, whereby rotation of the drive screw results in axial translation of the drive beam.

15. The electromechanical surgical system according to claim 13, wherein the at least one force transmitting assembly of the shaft assembly includes a second gear train system interconnecting another of the at least one rotatable drive member of the surgical instrument and a rotation hub rotatably supported at a distal end of the neck housing, wherein the second gear train system varies at least one of:
 a rate of rotation between the another at least one rotatable drive member of the surgical instrument and the rotation hub of the shaft assembly; or
 an axis of rotation between the another at least one rotatable drive member of the surgical instrument and the rotation hub of the shaft assembly.

16. The electromechanical surgical system according to claim 11, wherein the at least one rotation receiving member of the end effector includes a drive screw rotatably supported in the lower jaw, wherein the drive beam is threadably supported on the drive screw, whereby rotation of the drive screw results in axial translation of the drive beam.

17. The electromechanical surgical system according to claim 1, wherein the shaft assembly further includes:
 an articulating neck assembly supported at the distal end of the outer tubular body;
 a distal neck housing supported at a distal end of the articulating neck assembly, and first and second diametrically opposed articulation cables extending at least partially along the neck assembly, wherein each articulation cable includes a distal end anchored to the distal neck housing, and a proximal end extending into the outer tubular body, the proximal end of each articulation cable being secured to a respective first and second rack, each rack being operatively connected to one another by a spur gear, wherein axial displacement of the first rack in a first direction results in:
 axial displacement of the respective first articulation cable in the first direction;
 articulation of the neck assembly in a first off-axis direction; and
 axial displacement of the second articulation cable in a direction opposite to the first direction.

18. The electromechanical surgical system according to claim 17, wherein the shaft assembly further includes:
 a threaded rod extending proximally from the first rack; and
 a threaded shaft threadably connected to the threaded rod extending from the first rack, the threaded shaft being connected to another at least one rotatable drive member of the surgical instrument, wherein rotation of the another at least one rotatable drive member of the surgical instrument imparts rotation to the threaded shaft and, in turn, axial displacement of the threaded rod and first rack.

19. The electromechanical surgical system according to claim 1, wherein the shaft assembly further includes:
 an articulating neck assembly supported at the distal end of the outer tubular body, the neck assembly defining a central axis and being articulatable in a first plane;
 a distal neck housing supported at a distal end of the articulating neck assembly,
 first and second diametrically opposed articulation cables extending at least partially along the neck assembly;
 a first drive cable extending at least partially along the neck assembly and defining a first drive axis spaced a radial distance from the central axis, the first drive axis being defined by a first drive plane extending orthogonal to the first plane; and
 a second drive cable extending at least partially along the neck assembly and defining a second drive axis spaced a radial distance from the central axis, the second drive axis being defined by a second drive plane extending orthogonal to the first plane;
 wherein the first drive cable and the second drive cable are diametrically opposed to one another.

20. An electromechanical surgical system, comprising:
 a hand-held surgical instrument including an instrument housing defining a connecting portion for selectively connecting with a shaft assembly, the surgical instrument having at least one rotatable drive member;
 an end effector configured to perform at least one function and including:
 an upper jaw;
 a lower jaw;
 a drive beam translatable through at least one of the upper jaw or the lower jaw to move the lower jaw relative to the upper jaw; and
 a cartridge assembly selectively receivable in the lower jaw and including:
 a cartridge body defining a longitudinally extending knife slot;

a plurality of staples disposed in individual staple retaining slots formed in the cartridge body, wherein the staple retaining slots are arranged in multiple longitudinally extending rows disposed on opposed lateral sides of the knife slot;

an actuation sled slidably supported in the cartridge body and being configured to expel at least a portion of the plurality of staples from the cartridge body upon a distal movement of the actuation sled from a proximal-most position; and a knife sled slidably supported in the cartridge body at a location proximal of the actuation sled, the knife sled including a knife blade extending into the knife slot, the drive beam engaging the knife sled and the actuation sled when the cartridge assembly is disposed in the lower jaw and when the drive beam is advanced, the knife sled of the cartridge assembly including a lock-out spring extending therefrom, wherein the lockout spring of the knife sled engages a lock-out notch defined in the cartridge body to inhibit advancement of the knife sled; and the shaft assembly being arranged for selectively interconnecting the end effector and the surgical instrument, the shaft assembly including:

a transmission housing configured and adapted for selective connection to the connecting portion of the surgical instrument and to be in operative communication with each of the at least one rotatable drive member of the surgical instrument;

an outer tubular body having a proximal end supported by the transmission housing and a distal end configured and adapted for operative connection with the end effector; and a force transmitting assembly for interconnecting a respective one of the at least one rotatable drive member of the surgical instrument and at least one rotation receiving member supported in the end effector, wherein the force transmitting assembly includes a first end that is connectable to the at least one rotatable drive member of the surgical instrument and a second end that is connectable to the at least one rotation receiving member of the end effector, wherein the force transmitting assembly transmits a rotation of the at least one rotatable drive member of the surgical instrument to the at least one rotation receiving member of the end effector.

21. An electromechanical surgical system, comprising:

a hand-held surgical instrument including an instrument housing defining a connecting portion for selectively connecting with a shaft assembly, the surgical instrument having at least one rotatable drive member;

an end effector configured to perform at least one function; and the shaft assembly being arranged for selectively interconnecting the end effector and the surgical instrument, the shaft assembly including:

a transmission housing configured and adapted for selective connection to the connecting portion of the surgical instrument and to be in operative communication with each of the at least one rotatable drive member of the surgical instrument;

an outer tubular body having a proximal end supported by the transmission housing and a distal end configured and adapted for operative connection with the end effector;

a force transmitting assembly including a first gear train system interconnecting the at least one rotatable drive member of the surgical instrument and at least one rotation receiving member of the end effector, wherein the first gear train system varies at least one of:

a rate of rotation between the at least one rotatable drive member of the surgical instrument and the at least one rotation receiving member of the end effector; or an axis of rotation between the at least one rotatable drive member of the surgical instrument and the at least one rotation receiving member of the end effector;

an articulating neck assembly, the first gear train system being disposed proximal of the articulating neck assembly;

a neck housing disposed distal of the articulating neck assembly, the neck housing supporting a neck first gear train of the at least one force transmitting assembly, wherein the neck first gear train interconnects an output of the first gear train system with the at least one rotation receiving member of the end effector, wherein the neck first gear train varies at least one of:

a rate of rotation between the output of the first gear train system and the at least one rotation receiving member of the end effector; or an axis of rotation between the output of the first gear train system and the at least one rotation receiving member of the end effector.

22. An electromechanical surgical system, comprising:

a hand-held surgical instrument including an instrument housing defining a connecting portion for selectively connecting with a shaft assembly, the surgical instrument having at least one rotatable drive member;

an end effector configured to perform at least one function; and the shaft assembly being arranged for selectively interconnecting the end effector and the surgical instrument, the shaft assembly including:

a transmission housing configured and adapted for selective connection to the connecting portion of the surgical instrument and to be in operative communication with each of the at least one rotatable drive member of the surgical instrument;

an outer tubular body having a proximal end supported by the transmission housing and a distal end configured and adapted for operative connection with the end effector;

a force transmitting assembly for interconnecting a respective one of the at least one rotatable drive member of the surgical instrument and at least one rotation receiving member supported in the end effector, wherein the force transmitting assembly includes a first end that is connectable to the at least one rotatable drive member of the surgical instrument and a second end that is connectable to the at least one rotation receiving member of the end effector, wherein the force transmitting assembly transmits a rotation of the at least one rotatable drive member of the surgical instrument to the at least one rotation receiving member of the end effector;

an articulating neck assembly supported at the distal end of the outer tubular body;

a distal neck housing supported at a distal end of the articulating neck assembly; and first and second diametrically opposed articulation cables extending at least partially along the neck assembly, wherein each articulation cable includes a distal end anchored to the distal neck housing, and a proximal end extending into the outer tubular body, the proximal end of each articulation cable being secured to a respective first and second rack, each rack being operatively connected to one another by a spur gear, wherein axial displacement of the first rack in a first direction results in:
  axial displacement of the respective first articulation cable in the first direction;
  articulation of the neck assembly in a first off-axis direction; and
  axial displacement of the second articulation cable in a direction opposite to the first direction.

23. An electromechanical surgical system, comprising:
a hand-held surgical instrument including an instrument housing defining a connecting portion for selectively connecting with a shaft assembly, the surgical instrument having at least one rotatable drive member;
an end effector configured to perform at least one function; and
the shaft assembly being arranged for selectively interconnecting the end effector and the surgical instrument, the shaft assembly including:
  a transmission housing configured and adapted for selective connection to the connecting portion of the surgical instrument and to be in operative communication with each of the at least one rotatable drive member of the surgical instrument;
  an outer tubular body having a proximal end supported by the transmission housing and a distal end configured and adapted for operative connection with the end effector;
  a force transmitting assembly for interconnecting a respective one of the at least one rotatable drive member of the surgical instrument and at least one rotation receiving member supported in the end effector, wherein the force transmitting assembly includes a first end that is connectable to the at least one rotatable drive member of the surgical instrument and a second end that is connectable to the at least one rotation receiving member of the end effector, wherein the force transmitting assembly transmits a rotation of the at least one rotatable drive member of the surgical instrument to the at least one rotation receiving member of the end effector;
  an articulating neck assembly supported at the distal end of the outer tubular body, the neck assembly defining a central axis and being articulatable in a first plane;
  a distal neck housing supported at a distal end of the articulating neck assembly;
  first and second diametrically opposed articulation cables extending at least partially along the neck assembly;
  a first drive cable extending at least partially along the neck assembly and defining a first drive axis spaced a radial distance from the central axis, the first drive axis being defined by a first drive plane extending orthogonal to the first plane; and
  a second drive cable extending at least partially along the neck assembly and defining a second drive axis spaced a radial distance from the central axis, the second drive axis being defined by a second drive plane extending orthogonal to the first plane;
wherein the first drive cable and the second drive cable are diametrically opposed to one another.

* * * * *